US008497365B2

(12) United States Patent
Davis et al.

(10) Patent No.: US 8,497,365 B2
(45) Date of Patent: Jul. 30, 2013

(54) CYCLODEXTRIN-BASED POLYMERS FOR THERAPEUTICS DELIVERY

(76) Inventors: Mark E. Davis, Pasadena, CA (US); Jungyeon Hwang, Lexington, MA (US); Tianyi Ke, Arcadia, CA (US); Ching-Jou Lim, San Diego, CA (US); Thomas Schluep, La Crescenta, CA (US)

(*) Notice: Subject to any disclaimer, the term of this patent is extended or adjusted under 35 U.S.C. 154(b) by 0 days.

(21) Appl. No.: 13/198,403

(22) Filed: Aug. 4, 2011

(65) Prior Publication Data

US 2011/0294998 A1 Dec. 1, 2011

Related U.S. Application Data

(63) Continuation of application No. 12/002,305, filed on Dec. 14, 2007, now abandoned.

(60) Provisional application No. 60/897,096, filed on Jan. 24, 2007, provisional application No. 61/002,752, filed on Nov. 9, 2007.

(51) Int. Cl.
*B82Y 5/00* (2011.01)

(52) U.S. Cl.
USPC .......................................................... 536/53

(58) Field of Classification Search
None
See application file for complete search history.

(56) References Cited

U.S. PATENT DOCUMENTS

| | | | |
|---|---|---|---|
| 3,426,011 A | 2/1969 | Parmerter et al. |
| 3,453,257 A | 7/1969 | Parmerter |
| 3,472,835 A | 10/1969 | Buckler et al. |
| 3,502,601 A | 3/1970 | Case et al. |
| 3,654,261 A | 4/1972 | Johnson |
| 4,291,013 A | 9/1981 | Wahlig et al. |
| 4,347,234 A | 8/1982 | Wahlig et al. |
| 4,367,072 A | 1/1983 | Vogtle et al. |
| 4,438,253 A | 3/1984 | Casey et al. |
| 4,525,495 A | 6/1985 | Dorman et al. |
| 4,526,938 A | 7/1985 | Churchill et al. |
| 4,535,152 A | 8/1985 | Szejtli et al. |
| 4,570,629 A | 2/1986 | Widra |
| 4,572,832 A | 2/1986 | Kigasawa et al. |
| 4,582,865 A | 4/1986 | Balazs et al. |
| 4,587,268 A | 5/1986 | Pfirrmann |
| RE32,268 E | 10/1986 | Gordon |
| 4,625,014 A | 11/1986 | Senter et al. |
| 4,638,045 A | 1/1987 | Kohn et al. |
| 4,652,441 A | 3/1987 | Okada et al. |
| 4,675,381 A | 6/1987 | Bichon |
| 4,727,064 A | 2/1988 | Pitha |
| 4,745,160 A | 5/1988 | Churchill et al. |
| 4,746,734 A | 5/1988 | Tsuchiyama et al. |
| 4,764,604 A | 8/1988 | Muller |
| 4,774,329 A | 9/1988 | Friedman |
| 4,776,984 A | 10/1988 | Traitler et al. |
| 4,814,470 A | 3/1989 | Colin et al. |
| 4,818,542 A | 4/1989 | DeLuca et al. |
| 4,841,081 A | 6/1989 | Toda et al. |
| 4,877,778 A | 10/1989 | Carpenter et al. |
| 4,887,778 A | 12/1989 | Soth et al. |
| 4,898,654 A | 2/1990 | Toda et al. |
| 4,902,788 A | 2/1990 | Zemel et al. |
| 4,941,996 A | 7/1990 | Trend et al. |
| 5,098,793 A | 3/1992 | Rohrbach et al. |
| 5,100,669 A | 3/1992 | Hyon et al. |
| 5,143,854 A | 9/1992 | Pirrung et al. |
| 5,148,854 A | 9/1992 | Nakamoto |
| 5,183,883 A | 2/1993 | Tanaka et al. |
| 5,208,316 A | 5/1993 | Yoshinaga |
| 5,219,980 A | 6/1993 | Swidler |
| 5,275,824 A | 1/1994 | Carli et al. |
| 5,276,088 A | 1/1994 | Yoshinaga |
| 5,330,768 A | 7/1994 | Park et al. |
| 5,357,012 A | 10/1994 | Nussstein et al. |
| 5,376,509 A | 12/1994 | Yoshimoto et al. |
| 5,405,783 A | 4/1995 | Pirrung et al. |
| 5,424,186 A | 6/1995 | Fodor et al. |
| 5,438,072 A | 8/1995 | Bobee et al. |
| 5,439,686 A | 8/1995 | Desai et al. |
| 5,482,719 A | 1/1996 | Guillet et al. |
| 5,488,102 A | 1/1996 | Vetter |
| 5,498,421 A | 3/1996 | Grinstaff et al. |
| 5,510,240 A | 4/1996 | Lam et al. |
| 5,529,915 A | 6/1996 | Phillips et al. |
| 5,547,932 A | 8/1996 | Curiel et al. |

(Continued)

FOREIGN PATENT DOCUMENTS

| | | |
|---|---|---|
| EP | 0258780 A2 | 3/1988 |
| EP | 0502194 A1 | 9/1992 |

(Continued)

OTHER PUBLICATIONS de Groot et al ("Elongated Multiple Electronic Cascade and Cyclization Spacer Systems in Activatible Anticancer Prodrugs for Enhanced Drug Release," J. Org. Chem. 2001,66, 8815-8830).

Wingard et al ("Immobilization of a primary amine-containing drug, adriamycin," Applied Biochemistry and Biotechnology 19:117-127) (1988).

Shabat D et al., Chemical adaptor systems. Chemistry A European Journal. vol. 10, pp. 2626-2634. 2004.

De Groot, Franciscus M. H. et al. Elongated multiple electronic cascade and cyclization spacer systems in activatible anticancer prodrugs for enhanced drug release. Journal Of Organic Chemistry. vol. 66, pp. 8815-8830. 2001.

Gopin et al., New Chemical Adaptor Unit Designed to Release a Drug From A Tumor Targeting Devices by Enzymatic Triggering. Bioorganic & Medicinal Chemistry, Elsevier Science LTD. vol. 12 pp. 1853-1858. 2004.

(Continued)

*Primary Examiner* — Suzanne Ziska
(74) *Attorney, Agent, or Firm* — Lando & Anastasi LLP

(57) ABSTRACT

The present invention relates to novel compositions comprising polymeric moieties covalently attached to therapeutic agents, wherein the therapeutic agent is attached to the polymeric moiety through a tether. By selecting from a variety of tether groups and targeting ligands the polymers present methods for controlled delivery of the therapeutic agents. The invention also relates to methods of treating subjects with the therapeutic compositions described herein.

1 Claim, 6 Drawing Sheets

U.S. PATENT DOCUMENTS

| | | | |
|---|---|---|---|
| 5,549,974 | A | 8/1996 | Holmes |
| 5,571,882 | A | 11/1996 | Vetter |
| 5,608,015 | A | 3/1997 | Yoshinaga |
| 5,612,389 | A | 3/1997 | Chabrecek et al. |
| 5,635,383 | A | 6/1997 | Wu et al. |
| 5,652,347 | A | 7/1997 | Pouyani et al. |
| 5,656,611 | A | 8/1997 | Kabanov et al. |
| 5,679,773 | A | 10/1997 | Holmes |
| 5,688,488 | A | 11/1997 | Low et al. |
| 5,691,316 | A | 11/1997 | Agrawal et al. |
| 5,693,768 | A | 12/1997 | Bachmann et al. |
| 5,698,535 | A | 12/1997 | Geczy et al. |
| 5,698,582 | A | 12/1997 | Bastart et al. |
| 5,700,848 | A | 12/1997 | Soon-Shiong et al. |
| 5,714,512 | A | 2/1998 | Bastart et al. |
| 5,716,594 | A | 2/1998 | Elmaleh et al. |
| 5,728,804 | A | 3/1998 | Sharma et al. |
| 5,750,561 | A | 5/1998 | Bastart et al. |
| 5,820,847 | A | 10/1998 | Low et al. |
| 5,840,485 | A | 11/1998 | Lebl et al. |
| 5,847,170 | A | 12/1998 | Bouchard et al. |
| 5,855,900 | A | 1/1999 | Nobuhiko |
| 5,880,154 | A | 3/1999 | Boukrinskaia et al. |
| 5,917,016 | A | 6/1999 | Holmes |
| 5,985,916 | A | 11/1999 | Duncan et al. |
| 5,990,237 | A | 11/1999 | Bentley et al. |
| 6,033,486 | A | 3/2000 | Andros |
| 6,048,736 | A | 4/2000 | Kosak |
| 6,060,597 | A | 5/2000 | Tobe et al. |
| 6,068,831 | A | 5/2000 | Platzek et al. |
| 6,096,331 | A | 8/2000 | Desai et al. |
| 6,132,734 | A | 10/2000 | Thomas et al. |
| 6,207,195 | B1 | 3/2001 | Walsh et al. |
| 6,309,633 | B1 | 10/2001 | Ekwuribe et al. |
| 6,331,635 | B1 | 12/2001 | Bouchard et al. |
| 6,353,055 | B1 | 3/2002 | Kabanov et al. |
| 6,372,780 | B2 | 4/2002 | Bouchard et al. |
| 6,387,946 | B1 | 5/2002 | Bouchard et al. |
| 6,410,342 | B1 | 6/2002 | Affleck et al. |
| 6,420,176 | B1 | 7/2002 | Lisziewicz et al. |
| 6,426,184 | B1 | 7/2002 | Gao et al. |
| 6,506,405 | B1 | 1/2003 | Desai et al. |
| 6,509,323 | B1 | 1/2003 | Davis et al. |
| 6,515,017 | B1 | 2/2003 | Li et al. |
| 6,527,887 | B1 | 3/2003 | Ruebner et al. |
| 6,537,579 | B1 | 3/2003 | Desai et al. |
| 6,548,476 | B1 | 4/2003 | Wu et al. |
| 6,589,736 | B1 | 7/2003 | Rothschild et al. |
| 6,602,707 | B2 | 8/2003 | Hefeneider et al. |
| 6,630,124 | B1 | 10/2003 | Gozes et al. |
| 6,660,804 | B1 | 12/2003 | Weltrowski et al. |
| 6,667,293 | B1 | 12/2003 | Zhao et al. |
| 6,730,699 | B2 | 5/2004 | Li et al. |
| 6,740,643 | B2 | 5/2004 | Wolff et al. |
| 6,749,868 | B1 | 6/2004 | Desai et al. |
| 6,753,006 | B1 | 6/2004 | Desai et al. |
| 6,828,392 | B2 | 12/2004 | Meldal et al. |
| 6,849,462 | B1 | 2/2005 | Winkler et al. |
| 6,884,789 | B2 | 4/2005 | Davis et al. |
| 7,018,609 | B2 | 3/2006 | Hwang Pun et al. |
| 7,091,192 | B1 | 8/2006 | Davis et al. |
| 7,132,399 | B2 | 11/2006 | Hefeneider et al. |
| 7,141,540 | B2 | 11/2006 | Wang et al. |
| 7,166,302 | B2 | 1/2007 | Hwang Pun et al. |
| 7,241,907 | B2 | 7/2007 | Didier et al. |
| 7,427,605 | B2 | 9/2008 | Davis et al. |
| 7,776,814 | B2 * | 8/2010 | Domling et al. ............. 514/19.3 |
| 2001/0024829 | A1 | 9/2001 | Wolff et al. |
| 2001/0034333 | A1 | 10/2001 | Kosak |
| 2001/0044412 | A1 | 11/2001 | Wolff et al. |
| 2002/0032161 | A1 | 3/2002 | Ringshaw et al. |
| 2002/0107372 | A1 | 8/2002 | Hefeneider et al. |
| 2002/0111362 | A1 | 8/2002 | Rubinfeld |
| 2002/0151523 | A1 | 10/2002 | Davis et al. |
| 2003/0008818 | A1 | 1/2003 | Pun et al. |
| 2003/0017972 | A1 | 1/2003 | Pun et al. |
| 2003/0049203 | A1 | 3/2003 | Elmaleh et al. |
| 2003/0129262 | A1 | 7/2003 | Epner et al. |
| 2003/0144222 | A1 | 7/2003 | Wang et al. |
| 2003/0157030 | A1 | 8/2003 | Davis et al. |
| 2004/0024032 | A1 | 2/2004 | Voi et al. |
| 2004/0063654 | A1 | 4/2004 | Davis et al. |
| 2004/0072799 | A1 | 4/2004 | Li et al. |
| 2004/0077595 | A1 | 4/2004 | Cheng et al. |
| 2004/0087024 | A1 | 5/2004 | Bellocq et al. |
| 2004/0109888 | A1 | 6/2004 | Pun et al. |
| 2004/0248842 | A1 | 12/2004 | Wagner et al. |
| 2005/0272083 | A1 | 12/2005 | Seshagiri |
| 2006/0182795 | A1 | 8/2006 | Pun et al. |
| 2006/0210527 | A1 | 9/2006 | Davis |
| 2006/0263435 | A1 | 11/2006 | Davis et al. |
| 2007/0031844 | A1 | 2/2007 | Khvorova et al. |
| 2007/0128167 | A1 | 6/2007 | Pun et al. |
| 2008/0058427 | A1 | 3/2008 | Cheng et al. |
| 2008/0113031 | A1 | 5/2008 | Moodley et al. |
| 2008/0176958 | A1 | 7/2008 | Davis et al. |
| 2009/0163574 | A1 | 6/2009 | Kim et al. |
| 2009/0202989 | A1 | 8/2009 | Hillan |

FOREIGN PATENT DOCUMENTS

| | | |
|---|---|---|
| EP | 0587106 A2 | 3/1994 |
| EP | 0730869 A1 | 9/1996 |
| EP | WO 99/30727 | 6/1999 |
| EP | 1243276 | 9/2002 |
| EP | 1525890 | 4/2005 |
| EP | 1534340 A2 | 6/2005 |
| FR | 2665169 A1 | 1/1992 |
| GB | 1390479 A | 4/1975 |
| GB | 2197720 A | 5/1988 |
| HU | 200193B B | 9/1990 |
| JP | 58113198 A | 7/1983 |
| JP | 58167613 A | 10/1983 |
| JP | 02149513 A | 6/1990 |
| JP | 3221505 A | 9/1991 |
| JP | 4106101 A | 4/1992 |
| JP | 05331074 A | 12/1993 |
| JP | 7048451 A | 2/1995 |
| JP | 07316205 A | 12/1995 |
| JP | 9263535 A | 10/1997 |
| JP | 10158195 A | 6/1998 |
| RU | 2094059 C1 | 10/1997 |
| WO | 90/02141 A1 | 3/1990 |
| WO | 90/15070 A1 | 12/1990 |
| WO | 91/13100 A1 | 9/1991 |
| WO | 91/17300 A1 | 11/1991 |
| WO | 92/10092 A1 | 6/1992 |
| WO | 93/05084 A1 | 3/1993 |
| WO | 93/24150 A1 | 12/1993 |
| WO | 94/02518 A1 | 2/1994 |
| WO | 94/09826 A2 | 5/1994 |
| WO | 94/28031 A1 | 12/1994 |
| WO | 95/24221 A1 | 9/1995 |
| WO | 95/32739 A1 | 12/1995 |
| WO | 96/09073 A1 | 3/1996 |
| WO | 96/31220 A1 | 10/1996 |
| WO | 97/33044 A1 | 9/1997 |
| WO | 97/36948 A1 | 10/1997 |
| WO | 98/05689 A1 | 2/1998 |
| WO | 98/20967 A1 | 5/1998 |
| WO | 98/42382 A1 | 10/1998 |
| WO | 98/47496 A2 | 10/1998 |
| WO | 98/47536 A1 | 10/1998 |
| WO | 98/49350 A1 | 11/1998 |
| WO | 99/47172 A2 | 9/1999 |
| WO | 99/61062 A1 | 12/1999 |
| WO | WO-00/01734 | 1/2000 |
| WO | 00/06117 A1 | 2/2000 |
| WO | 00/09073 A2 | 2/2000 |
| WO | 00/33885 A1 | 6/2000 |
| WO | 00/40962 A1 | 7/2000 |
| WO | 00/66635 A1 | 11/2000 |
| WO | 00/75162 A1 | 12/2000 |
| WO | 00/75164 A1 | 12/2000 |
| WO | 01/37665 A1 | 5/2001 |
| WO | 01/66601 A1 | 9/2001 |
| WO | 02/49676 A2 | 6/2002 |
| WO | 02/057424 A2 | 7/2002 |

| | | |
|---|---|---|
| WO | 02/083180 A1 | 10/2002 |
| WO | 03/047518 A2 | 6/2003 |
| WO | 03/052060 A2 | 6/2003 |
| WO | WO-03/079972 | 10/2003 |
| WO | 2004022099 | 3/2004 |
| WO | WO-2004/019993 | 3/2004 |
| WO | WO-2004/022099 | 3/2004 |
| WO | 2004/032862 A2 | 4/2004 |
| WO | 2004/033620 A2 | 4/2004 |
| WO | 2004/039869 A1 | 5/2004 |
| WO | 2004069159 A2 | 8/2004 |
| WO | 2006012527 A1 | 2/2006 |
| WO | 2006/089007 A2 | 8/2006 |
| WO | 2006/105361 A2 | 10/2006 |

OTHER PUBLICATIONS

Shabat et al., In vivo activity in a catalytic antibody-prodrug system: Antibody catalyzed etoposide prodrug activation for selective chemotherapy. PNAS vol. 98, No. 13 7528-7533 (Jun. 19, 2001).

Tijerina Monical et al., Mechanisms of cytotoxcity in human ovarian carcinoma cells exposed to free Mce6 or HPMA copolymer-Mce6 conjugates. Photochemistry and Photobiology. vol. 77, No. 6. pp. 645-652. 2003.

Vrueh De R L A et al., Synthesis of a Lipophilic Prodrug of 9-(2-Phosphonylmethoxyethyl ) Ade Nine (PMEA) and its Incorporation into a Hepatocyte-Specific Lipidic Carrier. Pharmaceutical Research. vol. 16, No. 8. pp. 1179-1185. 1999.

de Groot et al., Elongated Multiple Electronic Cascade and Cyclization Spacer Systems in Activatible Anticancer Prodrugs for Enhanced Drug Release., J. Org. Chem. 2001, 66, 8815-8830.

Ebright et al., Incorporation of an EDTA-Metal Complex at a Rationally Selected Site within a Protein: Application to EDTA-Iron DNA Affinity Cleaving with Catabolite Gene Activator Protein (CAP) and CRO. Biochemestry 1992, 31, 10664-10670.

Jeong et al., Novel Intracellular Delivery System of ANtisense Oligonucleotide by Self-Assembled Hybrid Micelles Composed of DNA/PEG Conjugate and Cationic Fusogenic Peptide., Bioconjugate Chem. 2003, 14, 473-479.

Jones et al., Releasable Luciferin-Transporter Conjugates: Tools for the Real-Time Analysis of Cellular Uptake and Release. J. Am. Chem. Soc. 2006, 128, 6526-6527.

Kamruzzahan et al., Antibody Linking to Atomic Force Microscope Tips via Disulfide Bond Formation. Bloconjugate Chem. 2006, 17, 1473-1481.

Karathanasis et al., Preparation of in vivo cleavable agglomerated liposomes suitable for modulated pulmonary drug delivery. Journal of Controlled Release 103 (2005) 159-175.

Rejmanova et al., Polymers Containing Enzymatically Degradeable Bonds. Makromol. Chem. 184, 2009-2020 (1983).

U.S. Appl. No. 10/656,838, Cheng et al.

U.S. Appl. No. 11/881,325, Cheng et al.

U.S. Appl. No. 11/358,976, Davis et al.

Iser et al., "Chenodeoxycholic acid treatment of gallstones: A follow-up report and analysis of factors influencing response to therapy," N. Engl. J. Med., 1975 , vol. 293, No. 8, pp. 378-383 (abstract only).

Jicsinszky et al., "Comprehensive supramolecular chemistry," 1996, vol. 3, No. 4, pp. 138-188, Szeitli et al., Eds., Pergamon.

Kang et al., "Cyclodextrin complexation: influence on the solubility, stability, and cytotoxicity of camptothecin, an antineoplastic agent," European Journal of Pharmaceutical Sciences, 2002, vol. 15, pp. 163-170.

Karunaratne et al., "Synthesis of bulky b-lactams for inhibition of cell surface b-lactamase activity," Bioconjugate Chem., 1993 , vol. 4, pp. 434-439.

Keohavong et al. "Detection of K-ras mutations in lung carcinomas . . . " Clinical Cancer Research (1996) vol. 2, pp. 411-418.

Khan et al., "Methods for selective modifications of cyclodextrins", Chem. Rev. vol. 98, pp. 1977-1996 (1998).

Kneib-Cordonier et al., "Orthogonal solid-phase synthesis of human gastrin-I under mild conditions," Chem. Struc. and Biol., 1990, pp. 895-897, Rivier and Marshall, eds.

Kosmas et al "A phase I-II study of biweekly gemcitabine and irinotecan . . . " Cancer Chemother. Pharmacol. (2007) vol. 59, pp. 51-59.

La Mendola et al., "Copper(II) assisted self-assembly of functionalized beta-cyclodextrins with beta-alanyl-L-histidine" Journal of Supramolecular Chemistry, vol. 1, pp. 147-151 (2001).

Lam et al., "The one-bead-one compound combinatorial library method," Chem. Rev., 1997, vol. 97, pp. 411-448.

Lee et al., "Cucurbituril homologues and derivatives: new opportunities in supramolecular chemistry," Acc. Chem. Res., 2003, vol. 36, pp. 621-630.

Lewis, Hawley's Condensed Chemical Dictionary, John Wiley & Sons, Inc., 1987, pp. 311-312, New York, NY.

Li et al., "Molecular recognition by cyclodextrins (II) Inclusion of poly(ethylene glycol) by a-cyclodextrin," Polymer Preprints, 1991, vol. 40, No. 5-11, Abstract 4L 11 at p. E 1173, Japan (English Edition).

Li et al., "The complex formation between a-cyclodextrin and poly-(ethylene glycol) and its stoichiometric discussion," Polymer Preprints, 1991, vol. 40, No. 1-4, Abstract 11-12-26 at p. E 400, Japan (English Edition).

Lin et al. "Phase II study of CT-2103 as first-or second-line chemotherapy in patients with metastatic breast cancer: unexpected incidence of hypersensitivity reactions". Invest. New Drugs (2007) 25:369-375.

Liu et al., "Sugar containing polyamines prepared using galactose oxidase coupled with chemical reduction," J. Am. Chem. Soc., 1999, vol. 121, pp. 466-467.

Lowry O.H. et al., "Protein measurement with the folin phenol reagent," The Journal of Biological Chemistry, 1951, vol. 193, pp. 265-275.

Massarelli et al "KRAS mutation is an important predictor of resistance . . . " Clincial Cancer Research (2007) vol. 13, No. 10, pp. 2890-2896.

May et al., "Development of toxin-binding agent as a treatment for tunicaminyluracil toxicity: protection against tunicamycin poisoning of sheep," Australian Veterinary Journal, 1998, vol. 76, No. 11, pp. 752-756; chemical abstracts vol. 131, No. 3, pp. 193; Abstract No. 28805p (1999).

McCray et al., "Properties and uses of photoreactive caged compounds," Annu. Rev. Biophys. Chem., 1989, vol. 18, pp. 239-270.

McGall et al., "Light-directed synthesis of high-density oligonucleotide arrays using semiconductor photoresists," Proc. Natl. Acad. Sci., 1996, vol. 93, pp. 13555-13560.

McGall et al., "The efficiency of light-directed synthesis of DNA arrays on glass substrates," J. Am. Chem. Soc., 1997, vol. 119, pp. 5081-5090.

Melton, L.D. et al., "Synthesis of monosubstituted cyclohexaamyloses," Carbohydrate Research, 1971, vol. 18, pp. 29-37.

Middleton et al., "Synthetic biodegradable polymers as orthopedic devices," Biomaterials, 2000, vol. 21, pp. 2335-2346.

Minani et al, "Colon-specific drug delivery based on a cyclodextrin pro-drug: release behavior of biphenylylacetic acid from its cyclodextrin conjugates in rat intestinal tracts after oral administration," J. Pharm. Sci, 1998, vol. 87, No. 6, pp. 715-720.

Morii et al. "Cooperative Oligomerization Enhances Sequence-Selective DNA Binding by a Short Peptide" Journal of the American Chemical Society, vol. 118, No. 42, Oct. 23, 1996.

Mungall et al., "Use of the azido group in the synthesis of 5' terminal aminodeoxythymidine oligonucleotides," J. Org. Chem., 1975, vol. 40, No. 11, pp. 1659-1662.

Nande et al., "In vitro and in vivo toxicity testing for the prolonged local delivery of a cyclosert-camptothecin polymer conjugate in a model of intracranial glioma," 74th Annual American Association of Neurological Surgeons (Apr. 22-27, 2006) San Francisco, CA.

Numbenjajpon et al., "Preclinical efficacy of camptothecin polymer conjugate (IT-101) in human burkitt lymphoma bearing mice," Dec. 2006, 2006 ASH Annual Meeting (Dec. 9-12, 2006) Washington, DC.

Numbenjapon, T MD et al., "Preclinical results of the camptothecin-polymer conjugate IT-101 in multiple human lymphoma xenografts," Blood (Ash Annual Meeting Abstracts), Dec. 2007, 110:Abstract 1376.

4O'Shaughnessy et al., "Randomized, open-label, phase II trail of oral capecitabine (Xeloda®) vs. a reference arm of intravenous CMF (cyclophosphamide, methotrexate and 5-fluorouracil) as first-line thearpy for advanced/metastatic breat cancer" Annals of Oncology, vol. 12, pp. 1247-1254 (2001).

Oliver, J.C. et al., "A dose finding pharmacokinetic study of IT-101, the first de novo designed nanoparticle therapeutic, in refractory solid tumors," American Society of Clinical Oncology, 2008 Annual Meeting (May 30-Jun. 3, 2008) Chicago, IL.

Ooya et al., "Synthesis and characterization of an oligopeptide-terminated polyrotaxane as a drug carrier," Polym. Adv. Technol., 2000, vol. 11, pp. 642-651.

Ortega-Caballero et al., "Binding affinity properties of dendritic glycosides based on a b-cyclodextrin core toward guest molecules and concanavalin A," Journal of Organic Chemistry, 2001, vol. 66, No. 23, pp. 7786-7795.

Patchornik et al., "Photosensitive protecting groups," J. Am. Chem. Soc., 1970, vol. 92, pp. 6333-6335.

Pierce, 1989 Handbook and General Catalog, 1989, pp. 288-293, Rockford, IL.

Pillai et al., "Photoremovable protecting groups in organic synthesis," Synthesis, 1980, pp. 1-26.

Pirrung et al., "Comparison of methods for photochemical phosphoramidite-based DNA synthesis," J. Org. Chem., 1995, vol. 60, pp. 6270-6276.

Pizzolato et al. "The camptothecins" The Lancet (2003) vol. 361 pp. 2235-2242.

Pulfer et al., "Incorporation of nitric oxide-releasing crosslinked polyethyleneimine microspheres into vascular grafts," J. Biomed. Mat. Res., 1997, vol. 37, No. 2, pp. 182-189.

Pun et al., "Cyclodextrin-modified polyethylenimine polymers for gene delivery," Bioconjugate Chem., 2004, vol. 15, pp. 831-840 (available online Jun. 29, 2004).

Pun et al., "Development of a nonviral gene delivery vehicle for systemic application," Bioconjugate Chemistry, vol. 13, pp. 630-639.

Putnam et al., "Tissue engineering using synthetic extracellular matrices," Nature Med., 1996, vol. 2, pp. 824-826.

Ramaswamy et al., "Phase II Trail of Bevacizumab in Combination with Weekly Docetaxel in Metastatic Breast Cancer Patients" Clin. Cancer Research, vol. 12, No. 10, pp. 3124-3129 (2006).

Redenti et al., "Cyclodextrins in Oligonucleotide Delivery", Advanced Drug Delivery Reviews, vol. 53, No. 2 pp. 235-244 (2001).

Reineke et al., "Structural effects of carbohydrate-containing polycations on gene delivery. 1. Carbohydrate size and its distance from charge centers," Bioconjugate Chemistry, 2003, vol. 14, No. 1, pp. 247-254.

Reineke et al., "Structural effects of carbohydrate-containing polycations on gene delivery. 2. Charge center type," Bioconjugate Chemistry, 2003, vol. 14, No. 1, pp. 255-261.

Rich et al., "Preparation of a new o-nitrobenzyl resin for solid-phase synthesis of tert-butyloxycarbonyl-protected peptide acids," J. Am. Chem. Soc., 1975, vol. 97, pp. 1575-1579.

Saenger, "Structural aspects of cyclodextrins and their inclusion complexes," Inclusion Compounds, J. L. Atwood (ed.), 1984, vol. 2, No. 8, pp. 231-259, Academic Press, New York, NY.

Saijo et al. "Irinotecan combined with radition therapy . . . " Clinical Cancer Research (2002) vol. 4, suppl 1 pp. S21-S25.

Sandier et al., "Interaction between an adamantane end-capped poly-(ethylene oxide) and a b-cyclodextrin polymer," American Cancer Society, 2000, vol. 16, pp. 1634-1642.

Schluep et al., "Pharmacokinetics and biodistribution of the camptothecin-polymer conjugate IT-101 in rats and tumor bearing mice," Cancer Chemotherapy and Pharmacology, 2006, vol. 57, pp. 654-662 (available online Aug. 26, 2005).

Schluep et al., "Preclinical efficacy of the camptothecin-polymer conjugate IT-101 in multiple cancer models", Clin. Cancer Res., 2006, vol. 12, pp. 1606-1614.

Schluep, "Insert Therapeutics-product development update NSTI nanotech," Nanotech for Investors, May 21, 2007, Santa Clara, CA.

Schluep, et al., "Camptothecin-polymer conjugate shows improved biodistribution and preclinical efficacy in vivo," 2005 AACR Annual Meeting, (Apr. 16-20, 2005) Anaheim, CA.

Schluep, "Nanoparticulate chemotherapy with linear, cyclodextrin-containing polymers," May 15, 2006, XIII International Cyclodextrin Symposium, (May 14-17, 2006) Torino, Italy.

Sessa et al., "Phase 1 clinical study of the novel epothilone B analogue BMS-310705 given on a weekly schedule", Annals of Oncology, vol. 18: 1548-1553, 2007.

Smith et al., "Spectral characterization of β-cyclodextrin: triton X-100 complexes," J. Include. Phen. and Mol. Rec. Chem., 1991, vol. 10, pp. 471-484.

Smith, "Sweet revenge," Engineering & Science Caltech monthly newsletter, Mar. 2007, LXX, 1.

Song et al., "Catalyzed hydrolysis of RNA by metallic complexes of β-cyclodextrin derivative," Journal of Molecular Catalysis (China), 2001, vol. 15, No. 2, pp. 139-142.

Suh et al., "A new backbone of artificial enzymes obtained by cross-linkage of Poly(ethylenimine)," Bioorg. Med. Chem. Lett., 1998, vol. 8, pp. 1327-1330.

Szente et al., "Highly soluble cyclodextrin derivatives: chemistry, properties, and trends in development," Adv. Drug. Deliv. Rev., 1999, pp. 3617-3628.

Tabushi et al., "Artificial receptor recognizing hydrophobic carbonyl compounds," Journal of Organic Chemistry, 1986, vol. 51, No. 10, pp. 1918-1921.

Tabushi et al., "Bis(histamino)cyclodextrin-Zn-imidazole complex as an artificial carbonic anhydrase," J. Am. Chem. Soc., 1984, vol. 106, pp. 4580-4584.

Tabushi et al., "Characterization of regiospecific A,C- and A,D-disulfonate capping of β-cyclodextrin. Capping as an efficient production technique," J. Am. Chem. Soc., 1984, vol. 106, pp. 5267-5270.

Tabushi et al., "Specific bifunctionalization on cyclodextrin," Tetrahedron Lett., 1977, vol. 18, pp. 1527-1530.

Tamura et al. "Energy Transfer and Guest Responsive Fluorescence Spectra of Polyrotaxane Consisting of a-Cyclodextrins Bearing Naphthyl Moieties" The Chemical Society of Japan (2000), 73, pp. 147-154.

Tanaka et al., "Synthesis of doxorubicin-cyclodextrin conjugates," Journal of Antibiotics, 1994, vol. 47, No. 9, pp. 1025-7029.

Teague, S.J., "Facile synthesis of a o-nitrobenzyl photolabile linker for combinatorial chemistry," Tetrahedron Lett., 1996, vol. 37, pp. 5751-5754.

Tenjarla, S. et al., "Preparation, characterization, and evaluation of miconazole-cyclodextrin complexes for improved oral and topical delivery," Journal of Pharmaceutical Sciences, 1998, vol. 87, pp. 425-429.

Tojima et al., "Preparation of an a-cyclodextrin-linked chitosan derivative via reductive amination strategy," J. Polym. Sci., Part A: Polym. Chem., 1998, vol. 36, pp. 1965-1968.

Torchilin et al., "TAT peptide on the surface of liposomes affords their efficient intracellular delivery even at low temperature and in the presence of a metabolic inhibitors," PNAS, 2001, vol. 98, No. 15, pp. 8786-8791.

Trubetskoy, V. S., et al., "Self assembly of DNA-polymer complexes using template polymerization," Nucleic Acids Research, 1998, vol. 26, No. 18, pp. 4178-4185.

Uekama et al., "Cyclodextrin drug carrier systems," Chem. Rev., 1998, vol. 98, pp. 2045-2076.

Uekama et al., "Improvement of dissolution and absorption characteristics on phenytoin by a water-soluble b-cyclodextrin-epichlorohydrin polymer," Int. J. Pharm., 1985, vol. 23, pp. 35-42.

Warmuth, R. et al., "Recent highlights in hemicarcerand chemistry," Acc. Chem. Res., 2001, vol. 34, pp. 95-105.

Weickenmeier et al., "Cyclodextrin sidechain polyesters—synthesis and inclusion of adamantane derivatives," Macromol. Rapid Commun., 1996, vol. 17, pp. 731-736.

Wenz et al., "Threading cyclodextrin rings on polymer chains," Angewandte Chemie, International Edition, 1992, vol. 31, No. 2, pp. 197-199.

Williams D.F., "Biodegradation of surgical polymers," J. Mater. Sci., 1982, pp. 1233-1246.

Yano et al., "Colon-specific delivery of prednisolone-appended a-cyclodextrin conjugate; alleviation of systemic side effect after oral administration," Journal of Controlled Release, 2002, vol. 79, No. 1-3, pp. 103-112, Elsevier Science Publishers B.V., Amsterdam, NL.

Yano et al., "Prednisolone-appended a-cyclodextrin: alleviation of systemic adverse effect of prednisolone after intracolonic administration in 2,4,6-trinitrobenzenesulfonic acid-induced colitis rats," Journal of Pharmaceutical Sciences, 2001, vol. 90, No. 12, pp. 2103-2112.

Yano et al., "Preparation of prednisolone-appended a-, b-, and g-cyclodextrins: substitution at secondary hydroxyl groups and in vitro hydrolysis behavior," J. Pharm. Sci., 2001, vol. 4, pp. 493-503.

Yen et al., "First-in-human phase I trial of a cyclodextrin-containing polymer-camptothecin nanoparticle in patients with solid tumors", American Society of Clinical Oncology, 2007 annual meeting (Jun. 1-5, 2007) Chicago, IL.

Yoo et al., "Synthesis of oligonucleotides containing 3'-alkyl carboxylic acids using universal, photolabile solid phase synthesis supports," J. Org. Chem., 1995, vol. 60, pp. 3358-3364.

Zanta et al., "In vitro gene delivery to hepatocytes with galactosylated polyethylenimine," Bioconjugate Chem., 1997, vol. 8, pp. 839-844.

Zeidan et al., "A solvent-free method for isotopically or radioactively labeling cyclodextrins and cyclodextrin-containing polymers," Bioconjugate Chemistry, vol. 17, pp. 1624-1626 (available online Oct. 31, 2006).

Zhang et al., "Enthalpic domination of the chelate effect in cyclodextrin dimers," J. Am. Chem. Soc., 1993, vol. 115, pp. 9353-9354.

Zhang et al., "Ester hydrolysis by a catalytic cyclodextrin dimer enzyme mimic with a metallobipyridyl linking group," J. Am. Chem. Soc., 1997, vol. 119, pp. 1676-1681.

Zughul, M.B. et al., "Thermodynamics of propylparaben/β-cyclodextrin inclusion complexes," Pharm. Dev. Technol., 1998, vol. 3, pp. 43-53.

Davis et al., "Cyclodextrin-containing polymers for drug delivery," PharmTech, 2001, vol. 2-5, pp. 185-188.

Davis et al., "Linear, water-soluble, cyclodextrin-containing polymers for the delivery of broad ranging therapeutics," Jul. 1, 2003, 30th Annual Meeting of the CRS (Jul. 19-23, 2003), Glasgow, Scotland.

Deratani et al. "Linear cyclodextrin-containing polyelectrolytes 1. Synthesis of poly(1-vinylimidazole)-supported b-cyclodextrin. Effect of pH and ionic strength on the solution behaviour," Macromol. Chem. Phys., 1995, vol. 196, pp. 343-352.

Doukas et al. "Matrix immobilization enhances the tissue repair activity of growth factor gene therapy vectors" Human Gene Therapy, vol. 12, No. 7, pp. 783-798 (2001).

Du et al., "Steric considerations in supramolecular inclusion of modified β-cyclodextrins with triton X-100 and a-bromonaphthalene," Supramolecular Chem., 2005, vol. 7, pp. 209-214.

Epa et al., "Downregulation of the p75 neurotrophin receptor in tissue culture and in vivo, using β-cyclodextrin-adamantane-oligonucleotide conjugates," Antisense & Nucleic Acid Drug Development, 2000, vol. 10, pp. 469-478.

Esteva et al., "Phase II study of Weekly Docetaxel and Trastuzumab for Patients with HER-2-Overexpressing Metastatic Breast Cancer" Journal of Clinical Oncology, vol. 20., No. 7, pp. 1800-1808 (2002).

European Search Report from European Application Serial No. 03770286.7 dated Feb. 12, 2007.

Fang et al., "Recent Progress in Structure Activity Relationship and Mechanistic Studies of Taxol Analogues" Mini-Reviews in Medicinal Chemistry, vol. 5, pp. 1-12 (2005).

Ferrari et al., "ExGen 500 is an efficient vector for gene delivery to lung epithelial cells in vitro and in vivo," Gene Therapy, 1997, vol. 4, pp. 1100-1106.

Fieser et al., "Reagents for organic synthesis," Wiley New York, 1967, vol. 3, pp. 265-266.

Finsinger et al., "Protective copolymers for nonviral gene vectors: synthesis, vector characterization and application in gene delivery," Gene Delivery, 2000, vol. 7, pp. 1183-1192.

Fisher, "A versatile system for receptor-mediated gene delivery permits increased entry of DNA into target cells, enhanced delivery to the nucleus and elevated rates of transgene expression," Gene Therapy, 2000, vol. 7, pp. 1337-1343.

Fodor et al., "Light-directed, spatially addressable parallel chemical synthesis," Science, 1991, vol. 251, pp. 767-773.

Forgacs et al., "Interactions of some steroid drugs with b-cyclodextrin polymers," Journal of Chromatography A, 1999, vol. 845, No. 1 & 2, pp. 447-453.

Francis et al., "Polyethylene glycol modification: relevance of improved methodology to tumour targeting", J. Drug Targeting 3:321-340 (1996).

Fujita et al., "Guest-induced conformational change of b-cyclodextrin capped with an environmentally sensitive chromophore," Bioorganic Chemistry, 1982, vol. 11, pp. 72-84.

Fujita et al., "Selective recognition of alkanoates by a b-cyclodextrin flexibly capped with a chromophore," Bioorganic Chemistry, 1982, vol. 11, pp. 108-114.

Gao et al., "Potentiation of cationic liposome-mediated gene delivery by polycations," Biochemistry, 1996, vol. 35, pp. 1027-1036.

Gonzalez et al., "New Class of Polymers for the Delivery of Macromolecular Therapeutics" Bioconjugate Chemistry, vol. 10, No. 6 pp. 1068-1074 (1999).

Gosselet et al., "Association of hydrophobically modified poly (N,N-dimethylacrylamide hydroxyethylmethacrylate) with water soluble β-cyclodextrin polymers," Colloids and Surfaces: A: Physicochemical and Engineering Aspects, 1999, vol. 155, pp. 177-188.

Greenwald, R. "PEG drugs: and overview" Journal of Controlled Release (2001) vol. 74, pp. 159-171.

Guéritte et al., "General and Recent Aspects of the Chemistry and Structure-Activity Relationships of Tazoids", Current Pharmaceutical Design, vol. 7, pp. 1229-1249 (2001).

Habus et al., "Synthesis, hybridization properties, nuclease stability, and cellular uptake of the oligonucleotide-amino-b-cyclodextrins and adamantane conjugates," Bioconjugate Chem., 1995, vol. 6, No. 4, pp. 327-331.

Hammer et al., "Practical approach to solid-phase synthesis of C-terminal peptide amides under mild conditions based on a photolysable anchoring linkage," Int. J. Peptide Protein Res., 1990, vol. 36, pp. 31-45.

Harada et al., "Macromolecular recognition by cyclodextrins (I) Inclusion of water-soluble polymers by cyclodextrins," Polymer Preprints, 1991, vol. 40, pp. 5-11, Abstract 4L 10 at p. E 1172, Japan (English Edition).

Harada et al., "Synthesis of a tubular polymer from threaded cyclodextrins," Nature, 1993, vol. 364, pp. 516-518.

Harada et al., "The molecular necklace: a rotaxane containing many threaded a-cyclodextrins," Nature, 1992, vol. 356, pp. 325-327.

Hazum et al., "A photocleavable protecting group for the thiol function of cysteine," Proc. 16th Sup. European Peptide Sym., 1980, pp. 105-110.

Heidel, "Linear cyclodextrin-containing polymers and their use as delivery agents," Expert Opinion on Drug Delivery, 2006, vol. 3, No. 5, pp. 641-646.

Henry, "Synthetic chemistry at biotech firms," Chemical & Engineering News, Apr. 2, 2001, vol. 79, No. 14, American Chemical Society.

Hisamatsu et al., "Study on specific modification of glucosyl cyclodextrins," Starch, 1992, vol. 44, pp. 188-191.

Hoffman, "Chromatography of nucleic acids on cross-linked cyclodextrin gels having inclusion-forming capacity," J. Macromol. Sci.-Chem., 1973, vol. A7, No. 5, pp. 1147-1157.

Holmes et al., "Reagents for combinatorial organic synthesis: development of a new o-nitrobenzyl photolabile linker for solid phase synthesis," J. Org. Chem., 1995, vol. 60, pp. 2318-2319.

Homsi et al., "Phase I trial of poly-L-glutamate camptothecin (CT-2106) administered weekly in patients with advanced solid malignancies", Clin. Cancer Res., 2007, vol. 13, pp. 5855-5861.

Hristova-Kazmierski et al., "A new approach to enhanced bioavailability of biologically active peptides: conjugation of a d-opioid agonist to b-cyclodextrin," Bioorganic and Medicinal Chemistry Letters, 1993, vol. 3, No. 5, pp. 831-834.

Huh et al., "Synthesis of a-cyclodextrin-conjugated poly (e-lysine)s and their inclusion complexation behavior," Macromol. Rapid Commun., 2002, vol. 23, pp. 179-182.

Husain et al., "Complexation of doxorubicin with β- and g-cyclodextrins," Applied Spectroscopy, 1992, vol. 46, pp. 652-658.

Hwang et al., "Effects of structure of β-cyclodextrin-containing polymers on gene delivery," Bioconjugate Chem., 2001, vol. 12, No. 2, pp. 280-290.

Hwang et al., "Preclinical efficacy of the comptothecin-polymer conjugate IT-101 in multiple cancer models", Clinical Cancer Research, Mar. 1, 2006, vol. 12, No. 5.

Ikeda et al., "Supramolecular netwrok formation through inclusion complexation of an a-cyclodextrin-based molecular tube", Macromol. Rapid Comm. 21:1257-1262 (2000).

International Preliminary Report on Patentability including Written Opinion from International Application Serial No. PCT/US2010/048279 dated Nov. 8, 2010.

International Search Report dated Jan. 26, 2011 from International Application No. PCT/US2010/57913.

International Search Report dated Jul. 24, 2012 from International Application No. PCT/US 12/23308.

International Search Report dated Nov. 2, 2011 from International Application no. PCT/US11/37025.

International Search Report dated Nov. 8, 2010 from International Application no. PCT/US10/48973.

International Search Report dated Nov. 8, 2010 from International Application No. PCT/US2010/048279.

International Search Report for related Application No. PCT/US03/027588 dated Sep. 16, 2004.

International Search Report for related Application No. PCT/US03/31991 dated May 17, 2004.

International Search Report including Written Opinion for related Application No. PCT/US11/54025 dated Feb. 14, 2012.

"Adamantane," in the Merck Index, 11th ed., 1989, No. 140, pp. 24, Merck Research Laboratories.

"Amantadine," in the Merck Index, 11th ed., 1989, No. 380, pp. 60, Merck Research Laboratories.

"Arrowhead announces issuance of patent on subsidiary's key technology," Aug. 16, 2006, Press release.

"Arrowhead announces issuance of patent on subsidiary's key technology," May 8, 2007, Press Release.

"Arrowhead Research Subsidiary, Insert Therapeutics, receives FDA Approval for IT-101 Phase I Clinical," Mar. 14, 2006, Press release.

"Arrowhead Research Subsidiary, Insert Therapeutics, Treats first patient with nano-engineered anti-cancer therapeutic," Jul. 19, 2006, Business Wire.

"Arrowhead Subsidiaries, Insert and Calando, present data on Cyclosert(TM) drug delivery system at AACR meeting," Apr. 16, 2007, Press Release.

"Arrowhead Subsidiary, Insert Therapeutics, signs collaboration and option agreement for potent anticancer compound, tubulysin," Jan. 17, 2007, Press release.

"Arrowhead Subsidiary, Insert, publishes interim phase I data from human clinical trials for new cancer drug," Jun. 1, 2007, Press Release.

"Insert Therapeutics describes in vivo performance and versatility of Drug Delivery platform," Jul. 22, 2003, Insert Therapeutics News Release.

"Insert Therapeutics describes in vivo performance and versatility of lead anticancer compound," Apr. 17, 2005, News Release.

"Insert Therapeutics files investigational new drug application for lead anti-cancer compound IT-101," Feb. 9, 2006, News Release.

"Insert Therapeutics presents capabilities and versatility of drug delivery platform," Sep. 9, 2003, Insert Therapeutics News Release.

"Insert Therapeutics signs new partnership with R&D Biopharmaceuticals for epothilones," Mar. 1, 2007, Press Release.

"Insert Therapeutics, Inc. receives first patent on its Cyclosert(TM) polymer Technology," Feb. 4, 2003, Insert Therapeutics News Release.

"Insert Therapeutics, Inc. reports in vivo performance of Cyclosert(TM)—Camptothecin Anti-Cancer Formulation," Apr. 1, 2003, Insert Therapeutics News Release.

"Mark Davis Q&A—making it personal: finding a new way to treat cancer," Oct. 2007, Press release WNET (New York).

"Mark Davis to moderate 'novel approaches to drug delivery in cancer,'" Apr. 12, 2007, Press Release.

Albers et al., "Cyclodextrin derivatives in pharmaceutics," Crit. Rev. Ther. Drug Carrier Syst., 1995, vol. 12, pp. 311-337.

Aldrich Catalog/Handbook of Fine Chemicals, 1994-1995, pp. 399, Aldrich Chemical Company, Inc., Milwaukee, WI.

Amiel et al., "Association between amphiphilic poly(ethylene oxide) and β-cyclodextrin polymers: aggregation and phase separation," Advances in Colloid and Interface Science, 1999, vol. 79, pp. 105-122.

Amiel et al., "New associating polymer systems involving water soluble β-cyclodextrin polymers," Journal of Inclusion Phenomena and Molecular Recognition in Chemistry, 1996, vol. 25, pp. 61-67.

Amiel et al., "Associations between hydrophibically end-caped poly-ethylene oxide and water soluble b cyclodextrin polymers", Int. J. Polymer Analiysis & Characterization, 1:289-300 (1995).

Amit et al., "Photosensitive protecting groups of amino sugars and their use in glycoside synthesis. 2-nitrobenzyloxycarbonylamino and 6-nitroveratryloxycarbonylamino derivatives," J. Org. Chem., 1974, vol. 39, pp. 192-196.

Ashton et al., "Amino acid derivatives of b-cyclodextrin," Journal of Organic Chemistry, 1996, vol. 61, pp. 903-908.

Baldwin et al., "New photolabile phosphate protecting groups," Tetrahedron, 1990, vol. 46, pp. 6879-6884.

Barany et al., "A three-dimensional orthogonal protection scheme for solid-phase peptide synthesis under mild conditions," J. Am. Chem. Soc., 1985, vol. 107, pp. 4936-4942.

Bellocq et al. "Transferrin-containing, cyclodextrin polymer-based particles for tumor-targeted gene delivery," Bioconjugate Chem., 2003, vol. 14, pp. 1122-1132 (available online Nov. 4, 2003).

Bellocq et al. "Transferrin-targeted, cyclodextrin polycation-based gene vector for systemic delivery," Molecular Therapy, May, 2003, vol. 7, pp. S290.

Bellocq et al., "Synthetic biocompatible cyclodextrin-based constructs for local gene delivery to improve cutaneous wound healing," Bioconjugate Chem., 2004, vol. 15, pp. 1201-1211 (available online Oct. 26, 2004).

Bellof et al., "A new phenacyl-type handle for polymer supported peptide synthesis," Chimia, 1985, pp. 39317-39320.

Boussif et al., "A versatile vector for gene and oligonucleotide transfer into cells in culture and in vivo: polyethylenimine," Proceedings of the National Academy of Sciences, 1995, vol. 92, No. 16, pp. 7297-7301.

Breslow et al., "Cholesterol Recognition and binding by cyclodextrin dimers," J. Am. Chem. Soc., 1996, vol. 118, pp. 8495-8496.

Breslow et al., "Biomimetic reactions catalyzed by cyclodextrins and their derivatives," Chemical Reviews, 1998, vol. 98, No. 5, pp. 1997-2011.

Breslow et al., "Molecular recognition by cyclodextrin dimers," Tetrahedron, 1995, vol. 51, No. 2, pp. 377-388.

Breslow, "Biomimetic chemistry and artificial enzymes: catalysis by design," Accounts of Chemical Research, 1995, vol. 28, No. 3, pp. 146-153.

Breslow, "Studies in biomimetic chemistry," Pure & Applied Chemistry, 1988, vol. 70, No. 2, pp. 267-270.

Ceccato et al., "Molecular dynamics of novel a-cyclodextrin adducts studied by 13C-NMR relaxation," J. Phys. Chem., 1997, vol. 101, No. 26, pp. 5094-5099.

Cheng et al., "Antitumor activity of linear-cyclodextrin polymer conjugates of camptothecin," Nov. 1, 2003, AIChE Annual Meeting, (Nov. 16-21, 2003) San Francisco, CA.

Cheng et al., "Antitumor activity of systemic delivered camptothecin conjugates of linear, cyclodextrin-based polymers," 11th International Symposium on Recent Advances in Drug Delivery Systems (Mar. 3-6, 2003), Salt Lake City, UT.

Cheng et al., "Antitumor activity of β-cyclodextrin polymer-camptothecin conjugates," Molecular Pharmaceutics, vol. 1, pp. 183-193 (available online Apr. 3, 2004).

Cheng et al., "Linear, cyclodextrin-based polymers for the delivery of broad ranging therapeutics," Sep. 7, 2003, 2003 ACS Meeting (Sep. 7-11, 2003) New York, NY.

Cheng et al., "Synthesis of linear, β-cyclodextrin-based polymers and their camptothecin conjugates," Bioconjugate Chem, vol. 14, pp. 1007-1017 (available online Aug. 27, 2003).

Cram, "Cavitands: organic hosts with enforced cavities," Science, 1983, vol. 219, pp. 1177-1183.

Cram, "The design of molecular hosts, guests, and their complexes," Science, 1988, vol. 240, pp. 760-767.

Crini et al., "Linear cyclodextrin-poly (vinylamine): synthesis and NMR characterization," Euro. Polm. J., 1997, vol. 33, No. 7, pp. 1143-1151.

Cserhati, "Charge-transfer chromatographic study of the complex formation of some anticancer drugs with g-cyclodextrin," Analytical Biochemistry, 1995, vol. 225, pp. 328-332.

Danysz et al., "Aminoadamantanes as NMDA receptor antagonists and antiparkinsonian agents—preclinical studies," Neurosci. Biobehav. Rev., 1997, vol. 21, No. 4, pp. 455-468.

David et al., "Synthesis of hydrophobically end-capped poly(ethylene glycol)s with UV absorbing properties," Macromol. Rapid Commun., 2000, vol. 21, No. 14, pp. 990-993.

Davis et al., "Cyclodextrin-based pharmaceutics: past, present and future," Nature Reviews Drug Discovery, Dec. 1, 2004, vol. 3, No. 12, pp. 1023-1035.

European Search Report for Application No. 07 853 378.3 dated Apr. 16, 2013.

\* cited by examiner

Body Weight Loss in HT-29 Xenograft Implanted Mice

Figure 4. Distribution of CDP-Rho Systems Following Dosing

Cellular Uptake Analysis of CDP-Rho vs. LHRH-CDP-Rho by Flow Cytometry

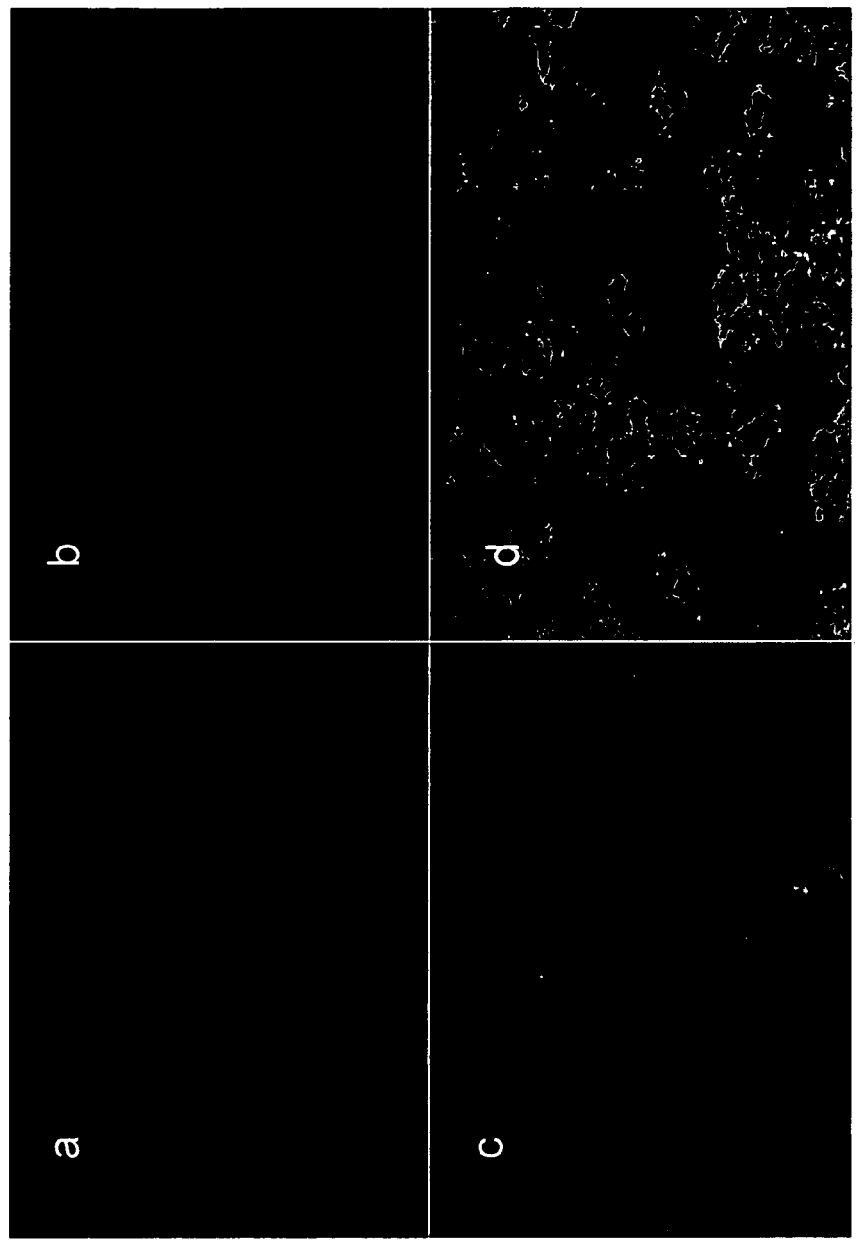
Figure 6. Colocalization of LHRH-CDP-Rho with Lysotracker Green

CYCLODEXTRIN-BASED POLYMERS FOR THERAPEUTICS DELIVERY

CROSS-REFERENCE TO RELATED APPLICATIONS

This patent application is a continuation of U.S. application Ser. No. 12/002,305, filed on Dec. 14, 2007, and claims the benefit of U.S. Provisional Application Nos. 60/897,096 filed on Jan. 24, 2007, and 61/002,752 filed on Nov. 9, 2007. The specifications of these applications are incorporated herein by reference in their entirety.

BACKGROUND OF THE INVENTION

Drug delivery of some small molecule therapeutic agents has been problematic due to their poor pharmacological profiles. These therapeutic agents often have low aqueous solubility, their bioactive forms exist in equilibrium with an inactive form, or high systemic concentrations of the agents lead to toxic side-effects. Some approaches to circumvent the problem of their delivery have been to conjugate the agent directly to a water-soluble polymer such as hydroxypropyl methacrylate (HPMA), polyethyleneglycol, and poly-L-glutamic acid. In some cases, such conjugates have been successful in solubilizing or stabilizing the bioactive form of the therapeutic agent, or achieving a sustained release formulation which circumvents complications associated with high systemic concentrations of the agent.

Another approach to the drug delivery problem has been to form host/guest inclusion complexes between the therapeutic agent and cyclodextrins or derivatives thereof. Cyclodextrins ($\alpha$, $\beta$, $\gamma$) and their oxidized forms have unique physico-chemical properties such as good water solubility, low toxicity and low immune response. To date, most of the drug delivery studies with cyclodextrins have focused on their ability to form supra-molecular complexes, wherein cyclodextrins form host/guest inclusion complexes with therapeutic molecules and thus alter the physical, chemical, and/or biological properties of these guest molecules.

There is an ongoing need for new approaches to the delivery of small therapeutic agents that have poor pharmacological profiles.

SUMMARY OF THE INVENTION

The present invention relates to novel compositions of polymer conjugates, defined as polymeric materials covalently coupled to therapeutic agents as carriers for therapeutics delivery. In one aspect, the present invention provides water-soluble, biocompatible polymer conjugates comprising a water-soluble, biocompatible polymer covalently attached to therapeutic agents through attachments that are cleaved under biological conditions to release the therapeutic agent.

One aspect of the invention relates to a polymer conjugate, comprising a therapeutic agent covalently attached to a polymer through a tether, wherein the tether comprises a self-cyclizing moiety. In some embodiments, the tether further comprises a selectivity-determining moiety.

One aspect of the invention relates to polymeric materials covalently coupled to therapeutic agents through a tether, wherein the tether comprises a self-cyclizing moiety. In certain embodiments, the tether further comprises a selectivity-determining moiety, e.g., covalently attached to the self-cyclizing moiety, such as in series.

In certain embodiments as disclosed herein, the selectivity-determining moiety is bonded to the self-cyclizing moiety between the self-cyclizing moiety and the polymer. In certain embodiments as disclosed herein, the selectivity-determining moiety promotes selectivity in the cleavage of the bond between the selectivity-determining moiety and the self-cyclizing moiety, e.g., under acidic conditions or under basic conditions. In certain embodiments as disclosed herein, the bond between the selectivity-determining moiety and the self-cyclizing moiety is selected from amide, carbamate, carbonate, ester, thioester, urea, and disulfide bonds.

In certain embodiments as disclosed herein, the self-cyclizing moiety is selected such that after cleavage of the bond between the selectivity-determining moiety and the self-cyclizing moiety, cyclization of the self-cyclizing moiety occurs, thereby releasing the therapeutic agent.

In certain embodiments as disclosed herein, cyclization of the self-cyclizing moiety forms a five- or six-membered ring. In certain embodiments as disclosed herein, the five- or six-membered ring is a heterocycle that comprises at least one heteroatom selected from nitrogen, oxygen, and sulfur. In certain embodiments as disclosed herein, the heterocycle is an imidazolidinone.

In certain embodiments as disclosed herein, the selectivity-determining moiety promotes enzymatic cleavage (i.e., by cathepsin or cathepsin B) of the bond between the selectivity-determining moiety and the self-cyclizing moiety. In certain embodiments as disclosed herein, the selectivity-determining moiety comprises a peptide (e.g., a dipeptide, tripeptide or tetrapeptide). In certain embodiments as disclosed herein, the peptide comprises a sequence selected from GFYA, GFLG, GFA, GLA, AVA, GVA, GIA, GVL, GVF, AVF, KF, and FK.

In certain embodiments as disclosed herein, the selectivity-determining moiety comprises an aminoalkylcarbonyloxyalkyl moiety. In certain embodiments as disclosed herein, the selectivity-determining moiety comprises cis-aconityl.

In certain embodiments as disclosed herein, the self-cyclizing moiety has a structure

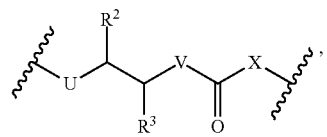

wherein

U is selected from $NR^1$ and S;

X is selected from O, $NR^5$, and S;

V is selected from O, S, and $NR^4$;

$R^2$ and $R^3$ are independently selected from hydrogen, alkyl, and alkoxy; or $R^2$ and $R^3$ together with the carbon atoms to which they are attached form a ring; and $R^1$, $R^4$, and $R^5$ are independently selected from hydrogen and alkyl.

In certain embodiments as disclosed herein, U is $NR^1$ and/or V is $NR^4$, and $R^1$ and $R^4$ are independently selected from methyl, ethyl, propyl, and isopropyl. In certain embodiments as disclosed herein, both $R^1$ and $R^4$ are methyl. In certain embodiments as disclosed herein, both $R^2$ and $R^3$ are hydrogen. In certain embodiments as disclosed herein, $R^2$ and $R^3$ together are —$(CH_2)_n$— wherein n is 3 or 4.

In certain embodiments as disclosed herein, the self-cyclizing moiety is selected from

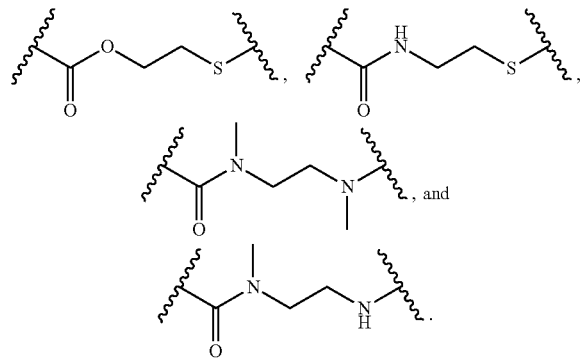

In certain embodiments as disclosed herein, U is bonded to the self-cyclizing moiety.

In certain embodiments as disclosed herein, the selectivity-determining moiety is represented by Formula A:

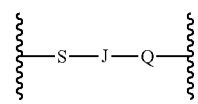

(A)

wherein
S a sulfur atom that is part of a disulfide bond;
J is optionally substituted hydrocarbyl; and
Q is O or $NR^{13}$, wherein $R^{13}$ is hydrogen or alkyl.

In certain embodiments as disclosed herein, the selectivity-determining moiety is represented by Formula B:

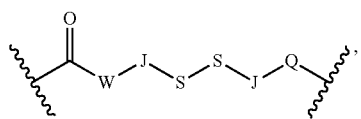

(B)

wherein
W is selected from $NR^{14}$, S, and O;
J, independently and for each occurrence, is hydrocarbyl or polyethylene glycol;
S is sulfur;
Q is O or $NR^{13}$, wherein $R^{13}$ is hydrogen or alkyl; and
$R^{14}$ is selected from hydrogen and alkyl.

In certain embodiments as disclosed herein according to Formula B, J comprises an aryl ring, such as a benzo ring. In certain such embodiments as disclosed herein, W and S are in a 1,2-relationship on the aryl ring. In certain embodiments as disclosed herein, the aryl ring is optionally substituted with alkyl, alkenyl, alkoxy, aralkyl, aryl, heteroaryl, halogen, —CN, azido, —$NR^xR^x$, —$CO_2OR^x$, —C(O)—$NR^xR^x$, —C(O)—$R^x$, —$NR^x$—C(O)—$R^x$, —$NR^xSO_2R^x$, —$SR^x$, —S(O)$R^x$, —$SO_2R^x$, —$SO_2NR^xR^x$, —$(C(R^x)_2)_n$—$OR^x$, —$(C(R^x)_2)_n$—$NR^xR^x$, and —$(C(R^x)_2)_n$—$SO_2R^x$; wherein $R^x$ is, independently for each occurrence, H or lower alkyl; and n is, independently for each occurrence, an integer from 0 to 2.

In certain embodiments as disclosed herein according to Formula A or B, J, independently and for each occurrence, is polyethylene glycol, polyethylene, polyester, alkenyl, or alkyl.

In certain embodiments as disclosed herein according to Formula A or B, J, independently and for each occurrence, represents a hydrocarbylene group comprising one or more methylene groups, wherein one or more methylene groups is optionally replaced by a group Y (provided that none of the Y groups are adjacent to each other), wherein each Y, independently for each occurrence, is selected from, substituted or unsubstituted aryl, heteroaryl, cycloalkyl, heterocycloalkyl, or —O—, C(=X) (wherein X is $NR^{30}$, O or S), —OC(O)—, —C(=O)O, —$NR^{30}$—, —$NR_1CO$—, —C(O)$NR^{30}$—, —S(O)$_n$— (wherein n is 0, 1, or 2), —OC(O)—$NR^{30}$, —$NR^{30}$—C(O)—$NR^{30}$—, —$NR^{30}$—C($NR^{30}$)—$NR^{30}$—, and —B($OR^{30}$)—; and $R^{30}$, independently for each occurrence, represents H or a lower alkyl.

In certain embodiments as disclosed herein according to Formula A or B, J, independently and for each occurrence, is substituted or unsubstituted lower alkylene (e.g., unsubstituted ethylene).

In certain embodiments as disclosed herein according to Formula A, the selectivity-determining moiety is

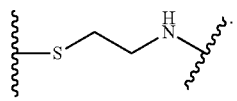 [SMILES: *NCCS*]

In certain embodiments as disclosed herein according to Formula B, the selectivity-determining moiety is selected from

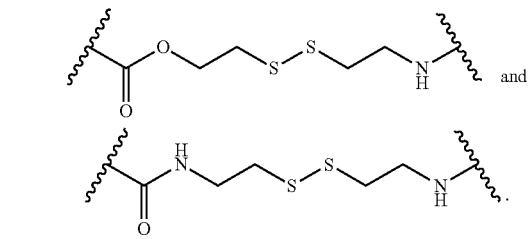

In certain embodiments as disclosed herein, the selectivity-determining moiety has a structure

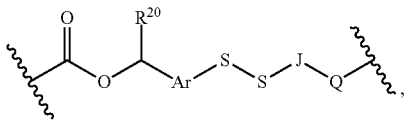

wherein Ar is a substituted or unsubstituted benzo ring;
J is optionally substituted hydrocarbyl (e.g., as defined anywhere above); and
Q is O or $NR^{13}$, wherein $R^{13}$ is hydrogen or alkyl.

In certain embodiments as disclosed herein Ar is unsubstituted. In certain embodiments as disclosed herein, Ar is a 1,2-benzo ring. In certain such embodiments, the selectivity determining moiety is

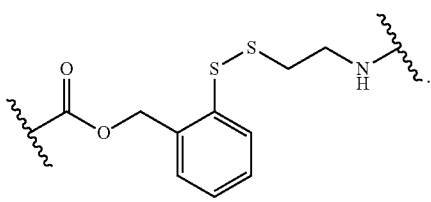 [SMILES: *NCCSSc1ccccc1COC(*)=O]

In certain embodiments as disclosed herein, the polymer comprises a plurality of cyclic moieties selected from cyclodextrins, crown ethers, cyclic oligopeptides, cryptands or cryptates, calixarenes, cavitands, or any combination thereof.

In certain embodiments, the polymer conjugate has a structure of Formula I:

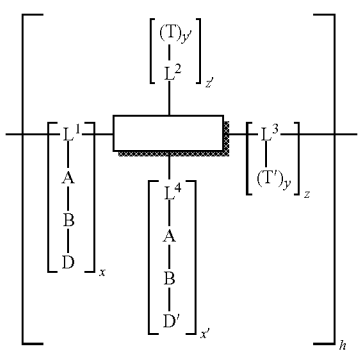

(I)

wherein P is a monomer moiety;

A, independently for each occurrence, is a selectivity-determining moiety or a direct bond;

B, independently for each occurrence, is a self-cyclizing moiety;

$L^1, L^2, L^3$ and $L^4$, independently for each occurrence, are a linker group;

D and D' are independently a therapeutic agent or prodrug thereof;

T and T' are independently a targeting ligand or precursor thereof;

y and y' are independently an integer from 1 to 10;

x, x', z, and z' are independently an integer from 0 to 10; and h is an integer from 2 to 30,000 (for example, from 2, 3, 4, 5, or 8 to about 25, 50, 100, 500, 1,000, 5,000, 10,000, 15,000, 20,000, or 25,000; or, for example, from 2, 3, or 4 to 5 or 10); wherein at least one occurrence of either x or x' is an integer greater than 0.

In certain embodiments, A is a selectivity-determining moiety.

In certain embodiments, $L^1$, $L^2$, $L^3$ and $L^4$ are independently selected from an alkyl chain, a polyethylene glycol (PEG) chain, polysuccinic anhydride, poly-L-glutamic acid, poly(ethyleneimine), an oligosaccharide, and an amino acid chain.

In certain embodiments, any of $L^1$, $L^2$, $L^3$ and $L^4$ are independently an alkyl chain wherein one or more methylene groups is optionally replaced by a group Y (provided that none of the Y groups are adjacent to each other), wherein each Y, independently for each occurrence, is selected from aryl, heteroaryl, carbocyclyl, heterocyclyl, or —O—, C(=X) (wherein X is $NR^1$, O or S), —OC(O)—, —C(=O)O, —$NR^1$—, —$NR^1$CO—, —C(O)$NR^1$—, —S(O)$_n$— (wherein n is 0, 1, or 2), —OC(O)—$NR^1$, —$NR^1$—C(O)—$NR^1$—, —$NR^1$—C($NR^1$)—$NR^1$—, and —B(O$R^1$)—; and $R^1$, independently for each occurrence, is H or lower alkyl.

In certain embodiments, A is selected such that the selectivity-determining moiety promotes selectivity in the cleavage of the bond between the selectivity-determining moiety and the self-cyclizing moiety.

In certain embodiments, B is capable of self-cyclizing to release the therapeutic agent once the bond between A and B has been cleaved.

In one aspect, the invention provides for a compound represented by Formula C:

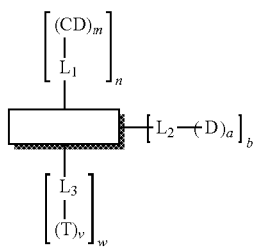

(C)

wherein

P represents a polymer chain;

CD represents a cyclic moiety;

$L_1$, $L_2$ and $L_3$, independently for each occurrence, may be absent or represent a linker group, provided that a plurality of occurrences of $L_2$ represent linkers that are cleavable under biological conditions;

D, independently for each occurrence, is selected from etoposide, tubulysin, epothilone, or an analog or derivative thereof;

T, independently for each occurrence, represents a targeting ligand or precursor thereof;

a, m and v, independently for each occurrence, represent integers in the range of 1 to 10;

n and w, independently for each occurrence, represent an integer in the range of 0 to about 30,000; and b represents an integer in the range of 1 to about 30,000; and either P comprises cyclodextrin moieties in the polymer chain or n is at least 1.

In certain embodiments, the compound is represented by Formula C':

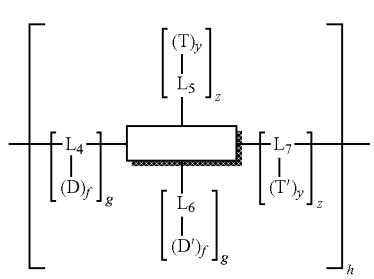

(C')

wherein

CD represents a cyclodextrin moiety, or derivative thereof;

$L_4$, $L_5$, $L_6$, and $L_7$, independently for each occurrence, may be absent or represent a linker group;

D and D', independently for each occurrence, is selected from etoposide, tubulysin, epothilone, or an analog or derivative thereof;

T and T', independently for each occurrence, represents the same or different targeting ligand or precursor thereof;

f and y, independently for each occurrence, represent an integer in the range of 1 and 10;

g and z, independently for each occurrence, represent an integer in the range of 0 and 10; and h is an integer from 2 to 30,000 (for example, from 2, 3, 4, 5, or 8 to about 25, 50, 100, 500, 1,000, 5,000, 10,000, 15,000, 20,000, or 25,000; or, for example, from 2, 3, or 4 to 5 or 10).

In certain embodiments, the compound is represented by Formula D:

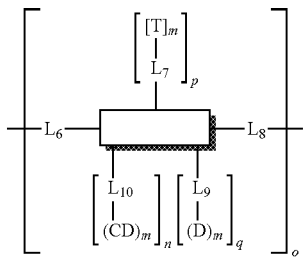

wherein

γ represents a monomer unit of a polymer that comprises cyclodextrin moieties;

T, independently for each occurrence, represents a targeting ligand or a precursor thereof;

$L_6$, $L_7$, $L_8$, $L_9$, and $L_{10}$, independently for each occurrence, may be absent or represent a linker group;

CD, independently for each occurrence, represents a cyclodextrin moiety or a derivative thereof;

D, independently for each occurrence, is selected from etoposide, tubulysin, epothilone, or an analog or derivative thereof;

m, independently for each occurrence, represents an integer in the range of 1 to 10;

o is an integer from 2 to 30,000 (for example, from 2, 3, 4, 5, or 8 to about 25, 50, 100, 500, 1,000, 5,000, 10,000, 15,000, 20,000, or 25,000; or, for example, from 2, 3, or 4 to 5 or 10); and p, n, and q, independently for each occurrence, represent an integer in the range of 0 to 10, wherein CD and D are each present at least once in the compound.

One aspect of the invention relates to a polymer covalently coupled to a therapeutic agent through a linker, wherein the linker comprises a phosphate group.

One aspect of the invention relates to a polymer, such as any polymer as described above, covalently coupled to a therapeutic agent through a linker, wherein the therapeutic agent is selected from etoposide, tubulysin, epothilone, or an analog or derivative thereof.

In certain embodiments as described above, the polymers employed may be biocompatible polymers.

In certain embodiments as described above, the polymer comprises a plurality of cyclic moieties selected from cyclodextrins, crown ethers, cyclic oligopeptides, cryptands or cryptates, calixarenes, cavitands, and any combination thereof.

In certain embodiments as described above, the therapeutic agent is a small molecule. In certain embodiments, the therapeutic agent contains an amino, hydroxyl, or thiol group. In certain embodiments, the therapeutic agent is attached to the self-cyclizing group through the amino, hydroxyl, or thiol group, preferably a hydroxyl group.

In certain embodiments as described above, the therapeutic agent is etoposide, tubulysin, epothilone, or an analog or derivative thereof. In certain embodiments as disclosed herein, the targeting ligand is a hormone, such a as a hormone that facilitates endocytosis. In certain embodiments, the hormone is luteinizing hormone-releasing hormone (LHRH).

In certain embodiments, a linker group represents a hydrocarbylene group wherein one or more methylene groups is optionally replaced by a group Y (provided that none of the Y groups are adjacent to each other), wherein each Y, independently for each occurrence, is selected from, substituted or unsubstituted aryl, heteroaryl, cycloalkyl, heterocycloalkyl, or —O—, C(=X) (wherein X is $NR_1$, O or S), —OC(O)—, —C(=O)O, —$NR_1$—, —$NR_1$CO—, —C(O)$NR_1$—, —S(O)$_n$— (wherein n is 0, 1, or 2), —OC(O)—$NR_1$, —$NR_1$—C(O)—$NR_1$—, —$NR_1$—C($NR_1$)—$NR_1$—, and —B(O$R_1$)—; and $R_1$, independently for each occurrence, represents H or a lower alkyl.

In certain embodiments, a linker group, e.g., between a therapeutic agent and a polymer, comprises a self-cyclizing moiety. In certain embodiments, a linker group, e.g., between a therapeutic agent and a polymer, comprises a selectivity-determining moiety.

In certain embodiments as disclosed herein, a linker group, e.g., between a therapeutic agent and a polymer, comprises a self-cyclizing moiety and a selectivity-determining moiety.

In certain embodiments, the linker group represents an amino acid or peptide, or derivative thereof.

In certain embodiments as disclosed herein, the therapeutic agent or targeting ligand is covalently bonded to the linker group via a biohydrolyzable bond (e.g., an ester, amide, carbonate, carbamate, or a phosphate).

In certain embodiments, the compound is biodegradable or bioerodable.

In certain embodiments as disclosed herein, the compound has a number average ($M_n$) molecular weight between 1,000 to 500,000 amu, or between 5,000 to 200,000 amu, or between 10,000 to 100,000 amu.

In one aspect, the invention provides for a pharmaceutical preparation comprising a pharmaceutical excipient and a compound of the invention, or a pharmaceutically acceptable ester, salt, or hydrate thereof. In certain embodiments, the therapeutic agent or prodrug thereof makes up at least 5% by weight of the compound. In certain embodiments, the therapeutic agent or prodrug thereof makes up at least 20% by weight of the compound.

In certain embodiments, the compound is water soluble.

In certain embodiments as disclosed herein, P is a linear polymer chain. In certain embodiments as disclosed herein, P is a branched polymer chain.

In certain embodiment as disclosed herein s, P comprises cyclodextrin moieties and at least one of the cyclodextrin moieties of P is oxidized. In certain such embodiments, a plurality of the cyclodextrin moieties of P are oxidized.

In certain embodiments as disclosed herein, P comprises cyclodextrin moieties that alternate with linker moieties in the polymer chain.

In certain embodiments, the linker moieties are attached to therapeutic agents or prodrugs thereof that are cleaved under biological conditions.

In one aspect, the invention provides for a method for delivering a therapeutic agent comprising administering to a patient in need thereof a therapeutically effective amount of one or more of the compounds of the invention. In certain such embodiments, the method is a method for treating cancer.

In one aspect, the invention relates to a compound represented by Formula C:

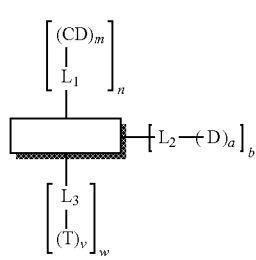

(C)

wherein
P represents a polymer chain;
CD represents a cyclodextrin moiety;
$L_2$ independently for each occurrence, may be absent or represents a linker group, wherein for one or more occurrences, $L_2$ is a linker group that comprises a phosphate group;
$L_1$ and $L_3$, independently for each occurrence, may be absent or represent a linker group;
D, independently for each occurrence, represents a therapeutic agent or a prodrug thereof;
T, independently for each occurrence, represents a targeting ligand or precursor thereof;
a, m and v, independently for each occurrence, represent integers in the range of 1 to 10;
n and w, independently for each occurrence, represent an integer in the range of 0 to about 30,000; and
b represents an integer in the range of 1 to about 30,000; and
wherein either P comprises cyclodextrin moieties in the polymer chain or n is at least 1, and wherein a plurality of therapeutic agents or prodrugs thereof are covalently attached to the polymer chain through attachments that are cleavable, e.g., under biological conditions.

In certain embodiments, for a plurality of occurrences, $L_2$ is a linker group comprising a phosphate group.

In certain embodiments, the compound is represented by Formula C':

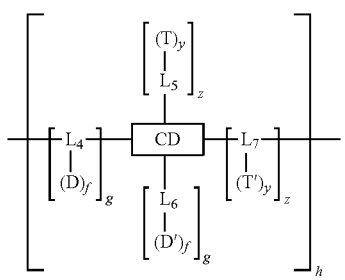

(C')

wherein
CD represents a cyclodextrin moiety, or derivative thereof;
$L_4$ and $L_6$, independently for each occurrence, may be absent or represent a linker group, wherein for one or more occurrences, $L_4$ or $L_6$ is a linker group that comprises a phosphate group;
$L_5$ and $L_7$, independently for each occurrence, may be absent or represent a linker group;

D and D', independently for each occurrence, represent the same or different therapeutic agent or prodrugs thereof;
T and T', independently for each occurrence, represents the same or different targeting ligand or precursor thereof;
f and y, independently for each occurrence, represent an integer in the range of 1 and 10;
g and z, independently for each occurrence, represent an integer in the range of 0 and 10; and
h is an integer from 2 to 30,000 (for example, from 2, 3, 4, 5, or 8 to about 25, 50, 100, 500, 1,000, 5,000, 10,000, 15,000, 20,000, or 25,000; or, for example, from 2, 3, or 4 to 5 or 10).

In certain embodiments, the compound represented by Formula D:

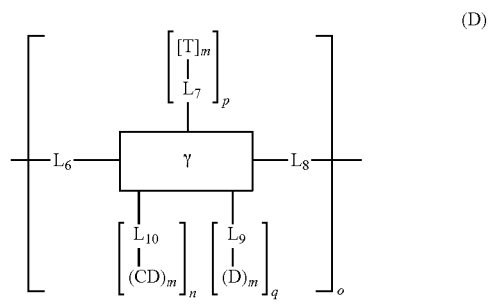

(D)

wherein
γ represents a monomer unit of a polymer;
T, independently for each occurrence, represents a targeting ligand or a precursor thereof;
$L_6$, $L_7$, $L_8$, and $L_{10}$, independently for each occurrence, may be absent or represent a linker group;
$L_9$, independently for each occurrence, may be absent or represents a linker group, wherein for one or more occurrences, $L_9$ is a linker group that comprises a phosphate group;
CD, independently for each occurrence, represents a cyclodextrin moiety or a derivative thereof;
D, independently for each occurrence, represents a therapeutic agent or a prodrug form thereof;
m, independently for each occurrence, represents an integer in the range of 1 to 10;
o is an integer from 2 to 30,000 (for example, from 2, 3, 4, 5, or 8 to about 25, 50, 100, 500, 1,000, 5,000, 10,000, 15,000, 20,000, or 25,000; or, for example, from 2, 3, or 4 to 5 or 10); and
p, n, and q, independently for each occurrence, represent an integer in the range of 0 to 10,
wherein CD and D are each present at least once in the compound.

In certain embodiments, at least one linker that connects the therapeutic agent or prodrug thereof to the polymer comprises a group represented by the formula

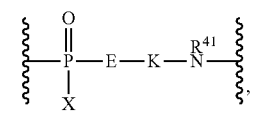

wherein
P is phosphorus;
O is oxygen;
E represents oxygen or $NR^{40}$;

K represents hydrocarbyl;

X is selected from $OR^{42}$ or $NR^{43}R^{44}$; and $R^{40}$, $R^{41}$, $R^{42}$, $R^{43}$, and $R^{44}$ independently represent hydrogen or optionally substituted alkyl.

In certain embodiments, E is $NR^{40}$ and $R^{40}$ is hydrogen.

In certain embodiments, K is lower alkylene (e.g., ethylene).

In certain embodiments, at least one linker comprises a group selected from

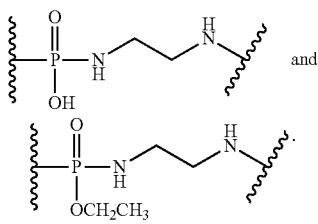

In certain embodiments, X is $OR^{42}$.

In certain embodiments, the linker group comprises an amino acid or peptide, or derivative thereof.

In certain embodiments as disclosed herein, the linker is connected to the therapeutic agent through a hydroxyl group (e.g., a phenolic hydroxyl group) on the therapeutic agent.

In certain embodiments as disclosed herein, the therapeutic agent is a small molecule, a peptide, a protein or a polymer that has therapeutic activity. In certain embodiments as disclosed herein, the therapeutic agent is a small molecule. In certain embodiments as disclosed herein, the therapeutic agent is selected from etoposide, tubulysin, epothilone, or an analog or derivative thereof.

In certain embodiments as disclosed herein, the therapeutic agent is hydrophobic and has a log P>0.4.

In certain embodiments as disclosed herein, the therapeutic agent has low aqueous solubility.

In certain embodiments as disclosed herein, the therapeutic agent or targeting ligand is covalently bonded to the linker group via a biohydrolyzable bond (e.g., an ester, amide, carbonate, or a carbamate).

In certain embodiments as disclosed herein, the therapeutic agent is selected from an anti-cancer, anti-fungal, anti-bacterial, anti-mycotic, or anti-viral therapeutic.

In certain embodiments as disclosed herein, the therapeutic agent is a receptor agonist. In certain embodiments, the therapeutic agent is a receptor antagonist.

In certain embodiments as disclosed herein, the compound is biodegradable or bioerodable.

In certain embodiments as disclosed herein, the compound has a number average ($M_n$) molecular weight between 1,000 to 500,000 amu, or between 5,000 to 200,000 amu, or between 10,000 to 100,000 amu.

In one aspect as disclosed herein, the invention provides for a pharmaceutical preparation comprising a pharmaceutical excipient and a compound of the invention, or a pharmaceutically acceptable ester, salt, or hydrate thereof.

In certain embodiments as disclosed herein, the therapeutic agent is selected from anorexics, antiarthritics, antiasthmatic agents, anticonvulsants, antidepressants; antihistamines, anti-inflammatory agents, antinauseants, antineoplastics, antipruritics, antipsychotics, antipyretics, antispasmodics, cardiovascular preparations, antihypertensives, diuretics, vasodilators, central nervous system stimulants, cough and cold preparations, decongestants, diagnostics, hormones, bone growth stimulants and bone resorption inhibitors, immunosuppressives, muscle relaxants, psychostimulants, sedatives, tranquilizers, anti-inflammatory agents, anti-epileptics, anesthetics, hypnotics, sedatives, neuroleptic agents, antidepressants, anxiolytics, anticonvulsant agents, neuron blocking agents, anticholinergic and cholinomimetic agents, antimuscarinic and muscarinic agents, antiadrenergics, antiarrhythmics, and antihypertensive agents.

In certain embodiments as disclosed herein, the therapeutic agent or prodrug thereof makes up at least 5% by weight of the compound. In certain embodiments, the therapeutic agent or prodrug thereof makes up at least 20% by weight of the compound.

In certain embodiments as disclosed herein, the compound is water soluble.

In certain embodiments, a plurality of the linker moieties are attached to therapeutic agents or prodrugs thereof and are cleaved under biological conditions.

In one aspect, the invention provides for a method for delivering a therapeutic agent comprising administering to a patient in need thereof a therapeutically effective amount of one or more of the compounds of the invention. In certain such embodiments, the method is a method for treating cancer.

BRIEF DESCRIPTION OF THE FIGURES

FIG. 6 shows substantial colocalization of LHRH-CDP-Rho with Lysotracker green as observed by confocal microscopy.

DETAILED DESCRIPTION OF THE INVENTION

I. Compounds

Figure 1:
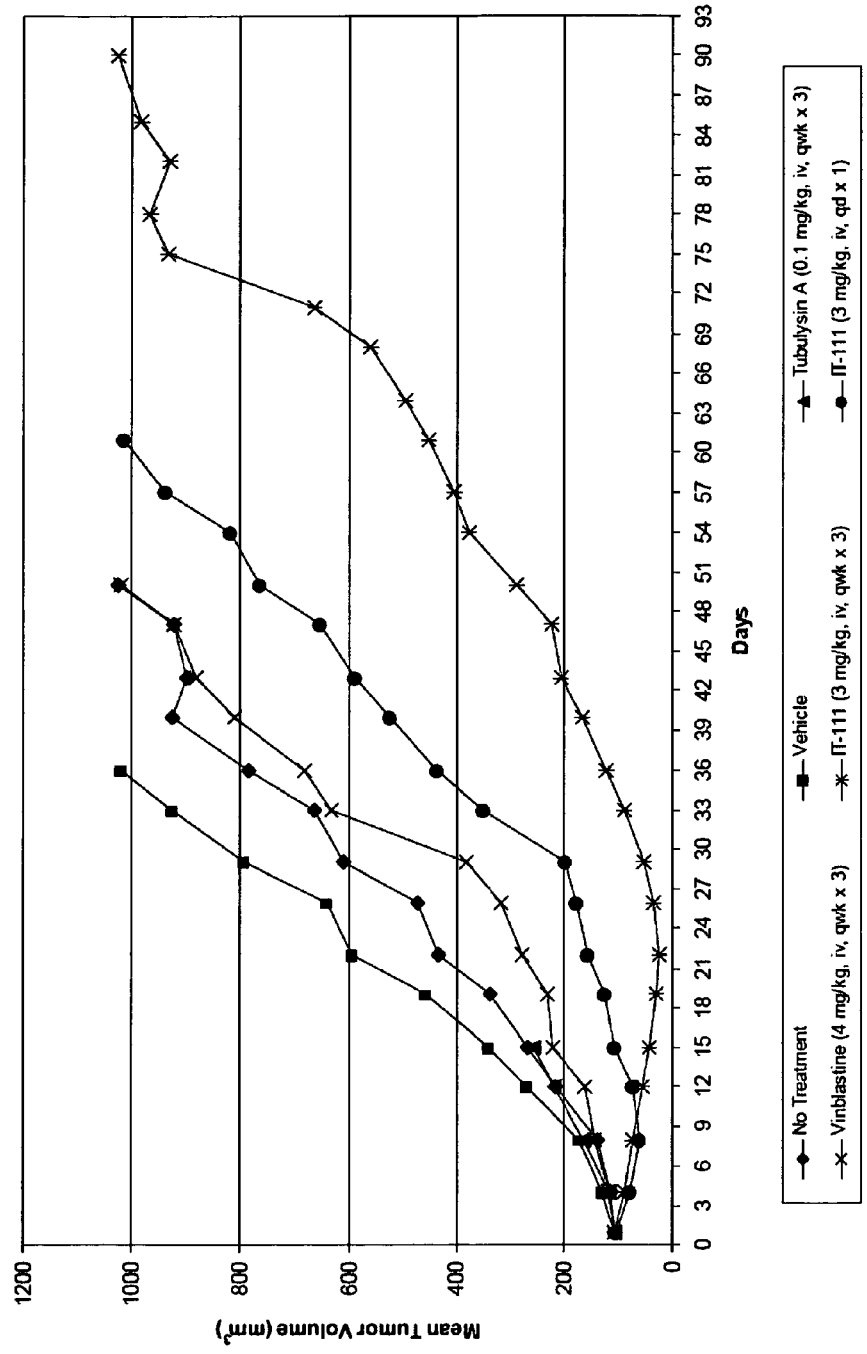
FIG. 1 shows the tumor volume mean summary data for HT29 colon carcinoma xenograft in mice treated with CDP-PEG-SS-Tubulysin.

The present invention provides water-soluble, biocompatible polymer conjugates comprising a water-soluble, biocompatible polymer covalently attached to therapeutic agents through attachments that are cleaved under biological conditions to release the therapeutic agent. In certain embodiments, a polymer conjugate comprises a therapeutic agent covalently attached to a polymer, preferably a biocompatible polymer, through a tether, e.g., a linker, wherein the tether comprises a selectivity-determining moiety and a self-cyclizing moiety which are covalently attached to one another in the tether, e.g., between the polymer and the therapeutic agent.

Polymeric conjugates of the present invention may be useful to improve solubility and/or stability of a therapeutic agent, reduce drug-drug interactions, reduce interactions with blood elements including plasma proteins, reduce or eliminate immunogenicity, protect the agent from metabolism, modulate drug-release kinetics, improve circulation time, improve drug half-life (e.g., in the serum, or in selected tissues, such as tumors), attenuate toxicity, improve efficacy, normalize drug metabolism across subjects of different species, ethnicities, and/or races, and/or provide for targeted delivery into specific cells or tissues. Poorly soluble and/or toxic compounds may benefit particularly from incorporation into polymeric compounds of the invention. In certain embodiments, the therapeutic agent is a small molecule, a macromolecule, an antibody, a peptide, a protein, an enzyme, a nucleic acid, or a polymer that has therapeutic function.

The polymer may be a polycation, polyanion, or non-ionic polymer. A polycationic or polyanionic polymer has at least one site that bears a positive or negative charge, respectively. In certain such embodiments, at least one of the linker moiety and the cyclic moiety comprises such a charged site, so that every occurrence of that moiety includes a charged site.

In certain embodiments, the polymer may be selected from polysaccharides, and other non-protein biocompatible polymers, and combinations thereof, that contain at least one terminal hydroxyl group, such as polyvinylpyrrollidone, poly(oxyethylene)glycol (PEG), polysuccinic anhydride, polysebacic acid, PEG-phosphate, polyglutamate, polyethylenimine, maleic anhydride divinylether (DIVMA), cellulose, pullulans, inulin, polyvinyl alcohol (PVA), N-(2-hydroxypropyl)methacrylamide (HPMA), dextran and hydroxyethyl starch (HES), and have optional pendant groups for grafting therapeutic agents, targeting ligands and/or cyclodextrin moieties. In certain embodiments, the polymer may be biodegradable such as poly(lactic acid), poly(glycolic acid), poly(alkyl 2-cyanoacrylates), polyanhydrides, and polyorthoesters, or bioerodible such as polylactide-glycolide copolymers, and derivatives thereof, non-peptide polyaminoacids, polyiminocarbonates, poly alpha-amino acids, polyalkyl-cyano-acrylate, polyphosphazenes or acyloxymethyl poly aspartate and polyglutamate copolymers and mixtures thereof.

In certain such embodiments, the polymer comprises cyclic moieties alternating with linker moieties that connect the cyclic structures, e.g., into linear or branched polymers, preferably linear polymers. The cyclic moieties may be any suitable cyclic structures, such as cyclodextrins, crown ethers (e.g., 18-crown-6, 15-crown-5, 12-crown-4, etc.), cyclic oligopeptides (e.g., comprising from 5 to 10 amino acid residues), cryptands or cryptates (e.g., cryptand[2.2.2], cryptand-2,1,1, and complexes thereof), calixarenes, or cavitands, or any combination thereof. Preferably, the cyclic structure is (or is modified to be) water-soluble. In certain embodiments, e.g., for the preparation of a linear polymer, the cyclic structure is selected such that under polymerization conditions, exactly two moieties of each cyclic structure are reactive with the linker moieties, such that the resulting polymer comprises (or consists essentially of) an alternating series of cyclic moieties and linker moieties, such as at least four of each type of moiety. Suitable difunctionalized cyclic moieties include many that are commercially available and/or amenable to preparation using published protocols. In certain embodiments, conjugates are soluble in water to a concentration of at least 0.1 g/mL, preferably at least 0.25 g/mL.

Thus, in certain embodiments, the invention relates to novel compositions of therapeutic cyclodextrin-containing polymeric compounds designed for drug delivery of therapeutic agents. In certain embodiments, these cyclodextrin-containing polymers improve drug stability and/or solubility, and/or reduce toxicity, and/or improve efficacy of the small molecule therapeutic when used in vivo. Furthermore, by selecting from a variety of linker groups, and/or targeting ligands, the rate of drug release from the polymers can be attenuated for controlled delivery.

The present invention includes polymer conjugates, such as cyclodextrin-containing polymer conjugates, wherein one or more therapeutic agents are covalently attached. The polymers include linear or branched cyclodextrin-containing polymers and polymers grafted with cyclodextrin. Exemplary cyclodextrin-containing polymers that may be modified as described herein are taught in U.S. Pat. Nos. 6,509,323 and 6,884,789, and U.S. Published Patent Application Nos. 2004-0109888, and 2004-0087024, which are incorporated herein in their entirety. These polymers are useful as carriers for small molecule therapeutic delivery, and may improve drug stability and solubility when used in vivo.

In certain embodiments, the underlying polymers are linear cyclodextrin-containing polymers, e.g., the polymer backbone includes cyclodextrin moieties. For example, the polymer may be a water-soluble, linear cyclodextrin polymer produced by providing at least one cyclodextrin derivative modified to bear one reactive site at each of exactly two positions, and reacting the cyclodextrin derivative with a linker having exactly two reactive moieties capable of forming a covalent bond with the reactive sites under polymerization conditions that promote reaction of the reactive sites with the reactive moieties to form covalent bonds between the linker and the cyclodextrin derivative, whereby a linear polymer comprising alternating units of cyclodextrin derivatives and linkers is produced. Alternatively the polymer may be a water-soluble, linear cyclodextrin polymer having a linear polymer backbone, which polymer comprises a plurality of substituted or unsubstituted cyclodextrin moieties and linker moieties in the linear polymer backbone, wherein each of the cyclodextrin moieties, other than a cyclodextrin moiety at the terminus of a polymer chain, is attached to two of said linker moieties, each linker moiety covalently linking two cyclodextrin moieties. In yet another embodiment, the polymer is a water-soluble, linear cyclodextrin polymer comprising a plurality of cyclodextrin moieties covalently linked together by a plurality of linker moieties, wherein each cyclodextrin moiety, other than a cyclodextrin moiety at the terminus of a polymer chain, is attached to two linker moieties to form a linear cyclodextrin polymer.

Cyclodextrins are cyclic polysaccharides containing naturally occurring D-(+)-glucopyranose units in an α-(1,4) linkage. The most common cyclodextrins are alpha (α)-cyclodextrins, beta (β)-cyclodextrins and gamma (γ)-cyclodextrins which contain six, seven, or eight glucopyranose units, respectively. Structurally, the cyclic nature of a cyclodextrin forms a torus or donut-like shape having an inner apolar or hydrophobic cavity, the secondary hydroxyl groups situated on one side of the cyclodextrin torus and the primary hydroxyl groups situated on the other. Thus, using (β)-cyclodextrin as an example, a cyclodextrin is often represented schematically as follows.

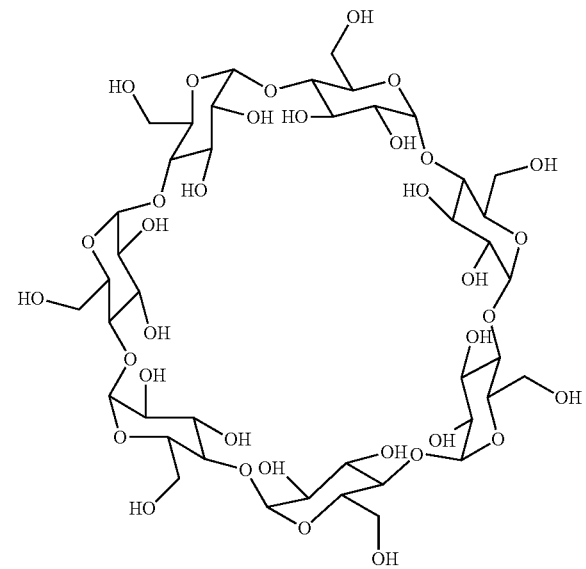

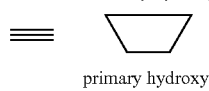

The side on which the secondary hydroxyl groups are located has a wider diameter than the side on which the primary hydroxyl groups are located. The present invention contemplates covalent linkages to cyclodextrin moieties on the primary and/or secondary hydroxyl groups. The hydrophobic nature of the cyclodextrin inner cavity allows for host-guest inclusion complexes of a variety of compounds, e.g., adamantane. (Comprehensive Supramolecular Chemistry, Volume 3, J. L. Atwood et al., eds., Pergamon Press (1996); T. Cserhati, *Anal. Biochem.*, 1995, 225:328-332; Husain et al., Applied Spectroscopy, 1992, 46:652-658; FR 2 665 169). Additional methods for modifying polymers are disclosed in Suh, J. and Noh, Y., *Bioorg. Med. Chem. Lett.* 1998, 8, 1327-1330.

In certain embodiments, the invention provides a polymer conjugate, comprising a therapeutic agent covalently attached to a polymer (such as any of the polymers discussed above) through a tether, wherein the tether comprises a self-cyclizing moiety. In some embodiments, the tether further comprises a selectivity-determining moiety. Thus, one aspect of the invention relates to a polymer conjugate comprising a therapeutic agent covalently attached to a polymer, preferably a biocompatible polymer, through a tether, wherein the tether comprises a selectivity-determining moiety and a self-cyclizing moiety which are covalently attached to one another.

In some embodiments, the polymer may be biocompatible.

In some embodiments, the selectivity-determining moiety is bonded to the self-cyclizing moiety between the self-cyclizing moiety and the polymer.

In certain embodiments, the selectivity-determining moiety is a moiety that promotes selectivity in the cleavage of the bond between the selectivity-determining moiety and the self-cyclizing moiety. Such a moiety may, for example, promote enzymatic cleavage between the selectivity-determining moiety and the self-cyclizing moiety. Alternatively, such a moiety may promote cleavage between the selectivity-determining moiety and the self-cyclizing moiety under acidic conditions or basic conditions.

In certain embodiments, the invention contemplates any combination of the foregoing. Those skilled in the art will recognize that, for example, any polymer of the invention in combination with any self-cyclizing moiety, any selectivity-determining moiety, and/or any therapeutic agent are within the scope of the invention. As an example, any of the various particular recited embodiments for a compound of Formula C may be combined with any of the various particular recited embodiments of the selectivity-determining moiety.

In certain embodiments, the selectivity-determining moiety is selected such that the bond is cleaved under acidic conditions.

In certain embodiments where the selectivity-determining moiety is selected such that the bond is cleaved under basic conditions, the selectivity-determining moiety is an aminoalkylcarbonyloxyalkyl moiety. In certain embodiments, the selectivity-determining moiety has a structure

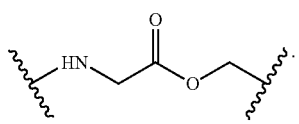 [SMILES: *COC(=O)CN*]

In certain embodiments where the selectivity-determining moiety is selected such that the bond is cleaved enzymatically, it may be selected such that a particular enzyme or class of enzymes cleaves the bond. In certain preferred such embodiments, the selectivity-determining moiety may be selected such that the bond is cleaved by a cathepsin, preferably cathepsin B.

In certain embodiments the selectivity-determining moiety comprises a peptide, preferably a dipeptide, tripeptide, or tetrapeptide. In certain such embodiments, the peptide is a dipeptide is selected from KF and FK, In certain embodiments, the peptide is a tripeptide is selected from GFA, GLA, AVA, GVA, GIA, GVL, GVF, and AVF. In certain embodiments, the peptide is a tetrapeptide selected from GFYA and GFLG, preferably GFLG.

In certain such embodiments, a peptide, such as GFLG, is selected such that the bond between the selectivity-determining moiety and the self-cyclizing moiety is cleaved by a cathepsin, preferably cathepsin B.

In certain embodiments, the selectivity-determining moiety is represented by Formula A:

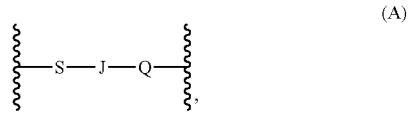

wherein
S a sulfur atom that is part of a disulfide bond;
J is optionally substituted hydrocarbyl; and
Q is O or NR$^{13}$, wherein R$^{13}$ is hydrogen or alkyl.

In certain embodiments, J may be polyethylene glycol, polyethylene, polyester, alkenyl, or alkyl. In certain embodiments, J may represent a hydrocarbylene group comprising one or more methylene groups, wherein one or more methylene groups is optionally replaced by a group Y (provided that none of the Y groups are adjacent to each other), wherein each Y, independently for each occurrence, is selected from, substituted or unsubstituted aryl, heteroaryl, cycloalkyl, heterocycloalkyl, or —O—, C(=X) (wherein X is NR$^{30}$, O or S), —OC(O)—, —C(=O)O, —NR$^{30}$—, —NR$_1$CO—, —C(O)NR$^{30}$—, —S(O)$_n$— (wherein n is 0, 1, or 2), —OC(O)—NR$^{30}$, —NR$^{30}$—C(O)—NR$^{30}$—, —NR$^{30}$—C(NR$^{30}$)—NR$^{30}$—, and —B(OR$^{30}$)—; and R$^{30}$, independently for each occurrence, represents H or a lower alkyl. In certain embodiments, J may be substituted or unsubstituted lower alkylene, such as ethylene. For example, the selectivity-determining moiety may be

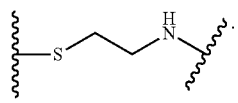 [SMILES: *NCCS*]

In certain embodiments, the selectivity-determining moiety is represented by Formula B:

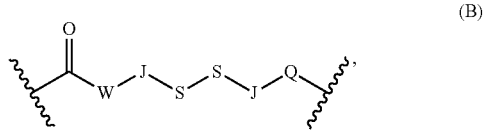

wherein
W is either a direct bond or selected from lower alkyl, NR$^{14}$, S, O;

S is sulfur;

J, independently and for each occurrence, is hydrocarbyl or polyethylene glycol;

Q is O or $NR^{13}$, wherein $R^{13}$ is hydrogen or alkyl; and $R^{14}$ is selected from hydrogen and alkyl.

In certain such embodiments, J may be substituted or unsubstituted lower alkyl, such as methylene. In certain such embodiments, J may be an aryl ring. In certain embodiments, the aryl ring is a benzo ring, In certain embodiments W and S are in a 1,2-relationship on the aryl ring. In certain embodiments, the aryl ring may be optionally substituted with alkyl, alkenyl, alkoxy, aralkyl, aryl, heteroaryl, halogen, —CN, azido, $R^x$, —$CO_2OR^x$, —C(O)—$NR^xR^x$, —C(O)—$R^x$, —$NR^x$—C(O)—$R^x$, —$NR^xSO_2R^x$, —$SR^x$, —S(O)$R^x$, —$SO_2R^x$, —$SO_2NR^xR^x$, —$(C(R^x)_2)_n$—$OR^x$, —$(C(R^x)_2)_n$—$NR^xR^x$, and —$(C(R^x)_2)_n$—$SO_2R^x$; wherein $R^x$ is, independently for each occurrence, H or lower alkyl; and n is, independently for each occurrence, an integer from 0 to 2.

In certain embodiments, the aryl ring is optionally substituted with alkyl, alkenyl, alkoxy, aralkyl, aryl, heteroaryl, halogen, —CN, azido, —$NR^xR^x$, —$CO_2OR^x$, —C(O)—$NR^xR^x$, —C(O)—$R^x$, —$NR^x$—C(O)—$R^x$, —$NR^xSO_2R^x$, —$SR^x$, —S(O)$R^x$, —$SO_2R^x$, —$SO_2NR^xR^x$, —$(C(R^x)_2)_n$—$OR^x$, —$(C(R^x)_2)_n$—$NR^xR^x$, and —$(C(R^x)_2)_n$—$SO_2R^x$; wherein $R^x$ is, independently for each occurrence, H or lower alkyl; and n is, independently for each occurrence, an integer from 0 to 2.

In certain embodiments, J, independently and for each occurrence, is polyethylene glycol, polyethylene, polyester, alkenyl, or alkyl.

In certain embodiments, independently and for each occurrence, represents a hydrocarbylene group comprising one or more methylene groups, wherein one or more methylene groups is optionally replaced by a group Y (provided that none of the Y groups are adjacent to each other), wherein each Y, independently for each occurrence, is selected from, substituted or unsubstituted aryl, heteroaryl, cycloalkyl, heterocycloalkyl, or —O—, C(=X) (wherein X is $NR^{30}$, O or S), —OC(O)—, —C(=O)O, —$NR^{30}$—, —$NR_1CO$—, —C(O)$NR^{30}$—, —S(O)$_n$— (wherein n is 0, 1, or 2), —OC(O)—$NR^{30}$, —$NR^{30}$—C(O)—$NR^{30}$—, —$NR^{30}$—C($NR^{30}$)—$NR^{30}$—, and —B($OR^{30}$)—; and $R^{30}$, independently for each occurrence, represents H or a lower alkyl.

In certain embodiments, J, independently and for each occurrence, is substituted or unsubstituted lower alkylene. In certain embodiments, J, independently and for each occurrence, is substituted or unsubstituted ethylene.

In certain embodiments, the selectivity-determining moiety is selected from

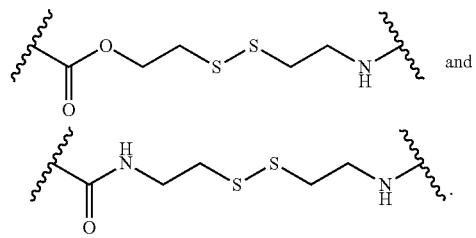

The selectivity-determining moiety may include groups with bonds that are cleavable under certain conditions, such as disulfide groups. In certain embodiments, the selectivity-determining moiety comprises a disulfide-containing moiety, for example, comprising aryl and/or alkyl group(s) bonded to a disulfide group. In certain embodiments, the selectivity-determining moiety has a structure

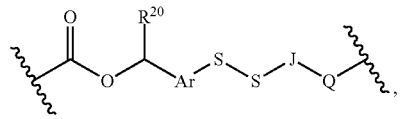

wherein

Ar is a substituted or unsubstituted benzo ring;

J is optionally substituted hydrocarbyl; and

Q is O or $NR^{13}$, wherein $R^{13}$ is hydrogen or alkyl.

In certain embodiments, Ar is unsubstituted. In certain embodiments, Ar is a 1,2-benzo ring. For example, suitable moieties within Formula B include

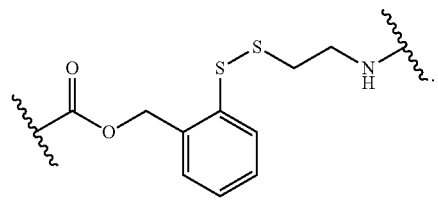 [SMILES: *NCCSSc1ccccc1COC(*)=O]

In certain embodiments, the self-cyclizing moiety is selected such that upon cleavage of the bond between the selectivity-determining moiety and the self-cyclizing moiety, cyclization occurs thereby releasing the therapeutic agent. Such a cleavage-cyclization-release cascade may occur sequentially in discrete steps or substantially simultaneously. Thus, in certain embodiments, there may be a temporal and/or spatial difference between the cleavage and the self-cyclization. The rate of the self-cyclization cascade may depend on pH, e.g., a basic pH may increase the rate of self-cyclization after cleavage. Self-cyclization may have a half-life after introduction in vivo of 24 hours, 18 hours, 14 hours, 10 hours, 6 hours, 3 hours, 2 hours, 1 hour, 30 minutes, 10 minutes, 5 minutes, or 1 minute.

In certain such embodiments, the self-cyclizing moiety may be selected such that, upon cyclization, a five- or six-membered ring is formed, preferably a five-membered ring. In certain such embodiments, the five- or six-membered ring comprises at least one heteroatom selected from oxygen, nitrogen, or sulfur, preferably at least two, wherein the heteroatoms may be the same or different. In certain such embodiments, the heterocyclic ring contains at least one nitrogen, preferably two. In certain such embodiments, the self-cyclizing moiety cyclizes to form an imidazolidone.

In certain embodiments, the self-cyclizing moiety has a structure

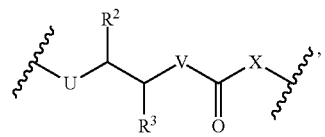

wherein

U is selected from $NR^1$ and S;

X is selected from O, $NR^5$, and S, preferably O or S;

V is selected from O, S and $NR^4$, preferably O or $NR^4$;

$R^2$ and $R^3$ are independently selected from hydrogen, alkyl, and alkoxy; or $R^2$ and $R^3$ together with the carbon atoms to which they are attached form a ring; and $R^1$, $R^4$, and $R^5$ are independently selected from hydrogen and alkyl.

In certain embodiments, U is $NR^1$ and/or V is $NR^4$, and $R^1$ and $R^4$ are independently selected from methyl, ethyl, propyl, and isopropyl. In certain embodiments, both $R^1$ and $R^4$ are methyl. On certain embodiments, both $R^2$ and $R^3$ are hydrogen. In certain embodiments $R^2$ and $R^3$ are independently alkyl, preferably lower alkyl. In certain embodiments, $R^2$ and $R^3$ together are —$(CH_2)_n$— wherein n is 3 or 4, thereby forming a cyclopentyl or cyclohexyl ring. In certain embodiments, the nature of $R^2$ and $R^3$ may affect the rate of cyclization of the self-cyclizing moiety. In certain such embodiments, it would be expected that the rate of cyclization would be greater when $R^2$ and $R^3$ together with the carbon atoms to which they are attached form a ring than the rate when $R^2$ and $R^3$ are independently selected from hydrogen, alkyl, and alkoxy. In certain embodiments, U is bonded to the self-cyclizing moiety.

In certain embodiments, the self-cyclizing moiety is selected from

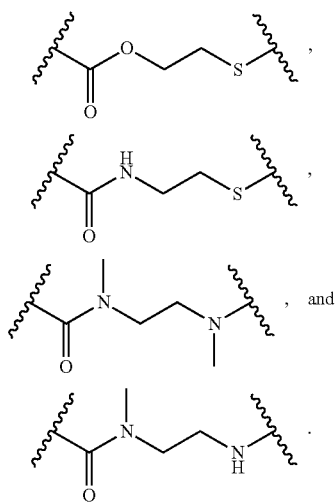

In certain embodiments, the selectivity-determining moiety may connect to the self-cyclizing moiety through carbonyl-heteroatom bonds, e.g., amide, carbamate, carbonate, ester, thioester, and urea bonds.

In certain embodiments, a therapeutic agent is covalently attached to a polymer through a tether, wherein the tether comprises a selectivity-determining moiety and a self-cyclizing moiety which are covalently attached to one another. In certain embodiments, the self-cyclizing moiety is selected such that after cleavage of the bond between the selectivity-determining moiety and the self-cyclizing moiety, cyclization of the self-cyclizing moiety occurs, thereby releasing the therapeutic agent. As an illustration, ABC may be a selectivity-determining moiety, and DEFGH maybe be a self-cyclizing moiety, and ABC may be selected such that enzyme Y cleaves between C and D. Once cleavage of the bond between C and D progresses to a certain point, D will cyclize onto H, thereby releasing therapeutic agent X, or a prodrug thereof.

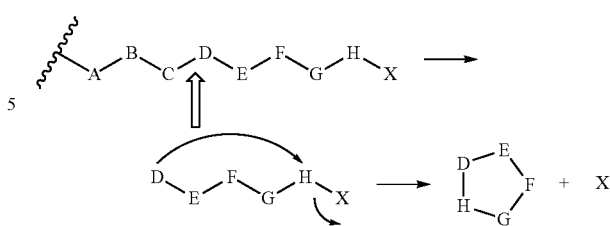

In certain embodiments therapeutic agent X may further comprise additional intervening components, including, but not limited to another self-cyclizing moiety or a leaving group linker, such as $CO_2$ or methoxymethyl, that spontaneously dissociates from the remainder of the molecule after cleavage occurs.

In certain embodiments, the invention provides a polymer conjugate, comprising a therapeutic agent covalently attached to a polymer (such as any of the polymers discussed above) through a linker, wherein the therapeutic agent is selected from etoposide, tubulysin, epothilone, or an analog or derivative thereof. The linkers may be cleavable under biological conditions. In some embodiments, a polymer may also comprise a targeting ligand and/or one or more cyclodextrin moieties pendant on the polymer. Thus one aspect of the invention relates to a polymer conjugate comprising a therapeutic agent covalently attached to a polymer through a tether, wherein the tether is cleavable under biological conditions.

One aspect of the invention relates to a compound, in some instances a polymeric compound, having a structure of Formula C:

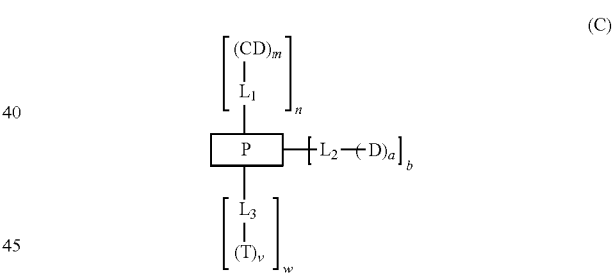

(C)

wherein

P represents a polymer chain;

CD represents a cyclic moiety;

$L_1$, $L_2$ and $L_3$, independently for each occurrence, may be absent or represent a linker group, provided that a plurality of occurrences of $L_2$ represent linkers that are cleavable under biological conditions;

D, independently for each occurrence, represents a therapeutic agent or a prodrug thereof;

T, independently for each occurrence, represents a targeting ligand or precursor thereof;

a, m and v, independently for each occurrence, represent integers in the range of 1 to 10;

n and w, independently for each occurrence, represent an integer in the range of 0 to about 30,000; and b represents an integer in the range of 1 to about 30,000, and wherein either P comprises a plurality of cyclic moieties in the polymer chain or n is at least 1.

In some embodiments, the cyclic moieties are independently selected from cyclodextrins, crown ethers, cyclic oligopeptides, cryptands or cryptates, calixarenes, cavitands, and any combination thereof. In certain embodiments, either P comprises cyclodextrin moieties in the polymer chain or n is at least 1.

In one aspect, Formula C may be represented by Formula C':

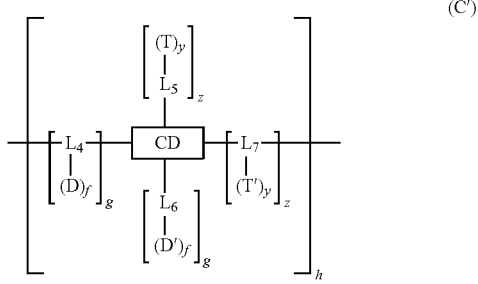

(C')

wherein
CD represents a cyclodextrin moiety, or derivative thereof;
$L_4$, $L_5$, $L_6$, and $L_7$, independently for each occurrence, may be absent or represent a linker group;
D and D', independently for each occurrence, represents a therapeutic agent or a prodrug thereof;
T and T', independently for each occurrence, represents the same or different targeting ligand or precursor thereof;
f and y, independently for each occurrence, represent an integer in the range of 1 and 10;
g and z, independently for each occurrence, represent an integer in the range of 0 and 10; and
h is an integer from 2 to 30,000 (for example, from 2, 3, 4, 5, or 8 to about 25, 50, 100, 500, 1,000, 5,000, 10,000, 15,000, 20,000, or 25,000; or, for example, from 2, 3, or 4 to 5 or 10).

In one aspect, Formula C may be represented by Formula D:

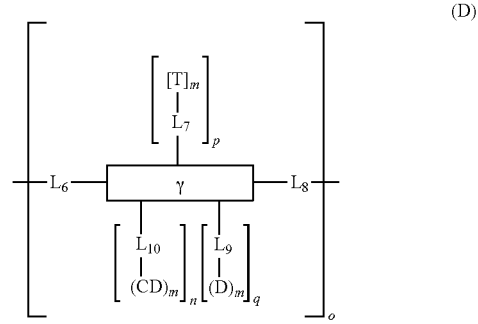

(D)

wherein
γ represents a monomer unit of a polymer;
T, independently for each occurrence, represents a targeting ligand or a precursor thereof;
$L_6$, $L_7$, $L_8$, $L_9$, and $L_{10}$, independently for each occurrence, may be absent or represent a linker group;
CD, independently for each occurrence, represents a cyclodextrin moiety or a derivative thereof;
D, independently for each occurrence, represents a therapeutic agent or a prodrug thereof;

m, independently for each occurrence, represents an integer in the range of 1 to 10;
o is an integer from 2 to 30,000 (for example, from 2, 3, 4, 5, or 8 to about 25, 50, 100, 500, 1,000, 5,000, 10,000, 15,000, 20,000, or 25,000; or, for example, from 2, 3, or 4 to 5 or 10); and
p, n, and q, independently for each occurrence, represent an integer in the range of 0 to 10, wherein CD and D are each present at least once in the compound.

In certain embodiments, the compound has a number average ($M_n$) molecular weight between 1,000 to 500,000 amu, between 5,000 to 200,000 amu, or between 10,000 to 100,000 amu.

In one aspect, the compounds of the invention, or a pharmaceutically acceptable ester, salt, or hydrate thereof, may be included in a pharmaceutical preparation that further comprises a pharmaceutical excipient.

In certain embodiments, B is a self-cyclizing moiety which is capable of self-cyclizing to release the therapeutic agent or prodrug thereof once the bond between the selectivity-determining moiety (A) and the self-cyclizing moiety has been cleaved. In certain such embodiments, the self-cyclizing moiety is capable of cyclizing to form an imidazolidinone.

In some embodiments, the therapeutic agent is a small molecule, for example, a hormone (e.g., luteinizing hormone-releasing hormone (LHRH)), etoposide, tubulysin, epothilone, or an analog or derivative thereof. In certain embodiments, therapeutic agent contains an amino, hydroxyl, or thiol group. In certain embodiments, the therapeutic agent is attached to the self-cyclizing group through the amino, hydroxyl, or thiol group. In certain embodiments, the therapeutic agent is attached to the self-cyclizing group through a hydroxyl group. In certain embodiments, the hormone facilitates endocytosis.

In certain embodiments, the therapeutic agent is a small molecule, a peptide, a protein, a nucleotide, a polynucleotide, or a polymer that has therapeutic function. In certain embodiments, the agent is an anti-cancer, anti-fungal, anti-bacterial, anti-mycotic, or anti-viral therapeutic. In certain embodiments, the agent is a receptor agonist. In certain embodiments, the agent is a receptor antagonist. In certain embodiments, the therapeutic agent is a protease inhibitor. Furthermore, a polymer of the present invention may contain one kind of therapeutic agent, or may contain more than one kind of therapeutic agent. For instance, two or more different cancer drugs, or a cancer drug and an immunosuppressant, or an antibiotic and an anti-inflammatory agent may be grafted on to the polymer. By selecting different selectivity determining moieties for different drugs, the release of each drug may be attenuated to achieve maximal dosage and efficacy.

In certain embodiments, the therapeutic agent may contain an amino, hydroxyl, or thiol group. In certain such embodiments, the therapeutic agent may be attached to the self-cyclizing group through the amino, hydroxyl, or thiol group. In certain such embodiments, the therapeutic agent is a hydroxyl-containing agent, including, but not limited to, salicylic acid, acetaminophen, morphine, etoposide, a tubulysin (preferably tubulysin A, tubulysin B, or tubulysin C), an epothilone, camptothecin, geldanamycin, rapamycin, or vancomycin, or an analog or derivative thereof.

In some embodiments, such therapeutic agents are covalently attached to subject polymers through functional groups comprising one or more heteroatoms, for example, hydroxy, thiol, carboxy, amino, and amide groups. Such groups may be covalently attached to the subject polymers through linker groups as described herein, for example, biocleavable linker groups, and/or through tethers, such as a tether comprising a selectivity-determining moiety and a self-cyclizing moiety which are covalently attached to one another.

In certain embodiments, the therapeutic agent is selected from anorexics, antiarthritics, antiasthmatic agents, anticonvulsants, antidepressants; antihistamines, anti-inflammatory agents, antinauseants, antineoplastics, antipruritics, antipsychotics, antipyretics, antispasmodics, cardiovascular preparations, antihypertensives, diuretics, vasodilators, central nervous system stimulants, cough and cold preparations, decongestants, diagnostics, hormones, bone growth stimulants and bone resorption inhibitors, immunosuppressives, muscle relaxants, psychostimulants, sedatives, tranquilizers, anti-inflammatory agents, anti-epileptics, anesthetics, hypnotics, sedatives, neuroleptic agents, antidepressants, anxiolytics, anticonvulsant agents, neuron blocking agents, anticholinergic and cholinomimetic agents, antimuscarinic and muscarinic agents, antiadrenergics, antiarrhythmics, and antihypertensive agents In certain embodiments, the therapeutic agent is hydrophobic and has a log P>0.4. In certain embodiments, the therapeutic agent has low aqueous solubility. In certain embodiments, the therapeutic agent or targeting ligand is covalently bonded to the linker group via a biohydrolyzable bond (e.g., an ester, amide, carbonate, or a carbamate), In certain embodiments, the therapeutic agent or prodrug thereof makes up at least 5%, 10%, 15%, or at least 20% by weight of the compound.

In certain embodiments, the compounds comprise cyclodextrin moieties and wherein at least one or a plurality of the cyclodextrin moieties of P is oxidized. In certain embodiments, the cyclodextrin moieties of P alternate with linker moieties in the polymer chain.

In certain embodiments, the compounds of the invention may be water soluble.

In certain embodiments, the linker group that connects to the therapeutic agent may comprise a self-cyclizing moiety, or a selectivity-determining moiety, or both. In certain embodiments, the selectivity-determining moiety is a moiety that promotes selectivity in the cleavage of the bond between the selectivity-determining moiety and the self-cyclizing moiety. Such a moiety may, for example, promote enzymatic cleavage between the selectivity-determining moiety and the self-cyclizing moiety. Alternatively, such a moiety may promote cleavage between the selectivity-determining moiety and the self-cyclizing moiety under acidic conditions or basic conditions.

In certain embodiments where the selectivity-determining moiety is selected such that the bond is cleaved enzymatically, it may be selected such that a particular enzyme or class of enzymes cleaves the bond. In certain preferred such embodiments, the selectivity-determining moiety may be selected such that the bond is cleaved by a cathepsin, preferably cathepsin B.

In certain embodiments the selectivity-determining moiety comprises a peptide, preferably a dipeptide, tripeptide, or tetrapeptide. In certain such embodiments, the peptide is a dipeptide is selected from KF and FK, In certain embodiments, the peptide is a tripeptide is selected from GFA, GLA, AVA, GVA, GIA, GVL, GVF, and AVF. In certain embodiments, the peptide is a tetrapeptide selected from GFYA and GFLG, preferably GFLG.

In certain such embodiments, a peptide, such as GFLG, is selected such that the bond between the selectivity-determining moiety and the self-cyclizing moiety is cleaved by a cathepsin, preferably cathepsin B.

In certain embodiments, the linker group that connects to the therapeutic agent may comprise a phosphate group, such as a phosphoramidite group. In certain embodiments, the linker group comprising a phosphate group is represented by the formula

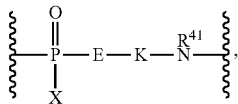

wherein
P is phosphorus;
O is oxygen;
E represents oxygen or $NR^{40}$;
K represents hydrocarbyl;
X is selected from $OR^{42}$ or $NR^{43}R^{44}$; and
$R^{40}$, $R^{41}$, $R^{42}$, $R^{43}$, and
$R^{44}$ independently represent hydrogen or optionally substituted alkyl, including lower alkyl (e.g., methyl, ethyl).

In certain embodiments, E is $NR^{40}$ and $R^{40}$ is hydrogen. In certain embodiments, K is lower alkylene, such as, for example, ethylene. In certain embodiments, X is $OR^{42}$.

In certain embodiments, the linker group is selected from

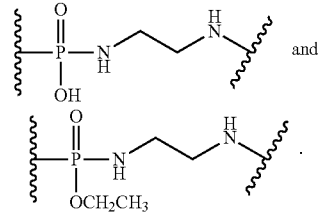

In certain embodiments, the linker group is connected to the therapeutic agent through a hydroxyl group (e.g., a phenolic hydroxyl group) on the therapeutic agent.

In certain embodiments, linker group comprises an amino acid or peptide, or derivative thereof.

In certain embodiments, any of the linker groups represents a hydrocarbylene group wherein one or more methylene groups is optionally replaced by a group Y (provided that none of the Y groups are adjacent to each other), wherein each Y, independently for each occurrence, is selected from, substituted or unsubstituted aryl, heteroaryl, cycloalkyl, heterocycloalkyl, or —O—, C(=X) (wherein X is $NR_1$, O or S), —OC(O)—, —C(=O)O, —$NR_1$—, —$NR_1$CO—, —C(O)$NR_1$—, —S(O)$_n$— (wherein n is 0, 1, or 2), —OC(O)—$NR_1$, —$NR_1$—C(O)—$NR_1$—, —$NR_1$—C($NR_1$)—$NR_1$—, and —B($OR_1$)—; and $R_1$, independently for each occurrence, represents H or a lower alkyl.

In certain embodiments, any of the linker groups may comprise a self-cyclizing moiety or a self-cyclizing moiety, or both. In certain embodiments, the selectivity-determining moiety may be bonded to the self-cyclizing moiety between the self-cyclizing moiety and the polymer.

In certain embodiments, any of the linker groups may independently be an alkyl chain, a polyethylene glycol (PEG) chain, polysuccinic anhydride, poly-L-glutamic acid, poly (ethyleneimine), an oligosaccharide, an amino acid chain, or any other suitable linkage. In certain embodiments, the linker group itself can be stable under physiological conditions, such as an alkyl chain, or it can be cleavable under physiological conditions, such as by an enzyme (e.g., the linkage contains a peptide sequence that is a substrate for a peptidase), or by hydrolysis (e.g., the linkage contains a hydrolyzable group, such as an ester or thioester). The linker groups can be biologically inactive, such as a PEG, polyglycolic acid, or polylactic acid chain, or can be biologically active, such as an oligo- or polypeptide that, when cleaved from the moieties, binds a receptor, deactivates an enzyme, etc. Various oligomeric linker groups that are biologically compatible and/or bioerodible are known in the art, and the selection of the linkage may influence the ultimate properties of the material, such as whether it is durable when implanted, whether it gradually deforms or shrinks after implantation, or whether it gradually degrades and is absorbed by the body. The linker group may be attached to the moieties by any suitable bond or functional group, including carbon-carbon bonds, esters, ethers, amides, amines, carbonates, carbamates, sulfonamides, etc.

In certain embodiments, any of the linker groups may independently be an alkyl group wherein one or more methylene groups is optionally replaced by a group Y (provided that none of the Y groups are adjacent to each other), wherein each Y, independently for each occurrence, is selected from aryl, heteroaryl, carbocyclyl, heterocyclyl, or —O—, C(=X) (wherein X is $NR^1$, O or S), —OC(O)—, —C(=O)O—, —$NR^1$—, —$NR^1$CO—, —C(O)$NR^1$—, —S(O)$_n$— (wherein n is 0, 1, or 2), —OC(O)—$NR^1$—, —$NR^1$—C(O)—$NR^1$—, —$NR^1$—C($NR^1$)—$NR^1$—, and —B($OR^1$)—; and $R^1$, independently for each occurrence, is H or lower alkyl.

In certain embodiments, any of the linker groups may independently be a derivatized or non-derivatized amino acid. In certain embodiments, linker groups with one or more terminal carboxyl groups may be conjugated, e.g., covalently conjugated, to the polymer. In certain embodiments, one or more of these terminal carboxyl groups may be capped by covalently attaching them to a therapeutic agent, a targeting ligand, or a cyclodextrin moiety via an (thio)ester or amide bond. In still other embodiments, linker groups with one or more terminal hydroxyl, thiol, or amino groups may be incorporated into the polymer. In preferred embodiments, one or more of these terminal hydroxyl groups may be capped by covalently attaching them to a therapeutic agent, a targeting ligand, or a cyclodextrin moiety via an (thio)ester, amide, carbonate, carbamate, thiocarbonate, or thiocarbamate bond. In certain embodiments, these (thio)ester, amide, (thio)carbonate or (thio)carbamates bonds may be biohydrolyzable, i.e., capable of being hydrolyzed under biological conditions.

In certain embodiments, the polymers as described above have polydispersities less than about 3, or even less than about 2.

The invention further contemplates methods for delivering a therapeutic agent comprising administering to a patient in need thereof a therapeutically effective amount of one or more of the compounds of the invention.

Tubulysins and derivatives and/or analogs thereof may be found, for example, in WO2004/005269, WO2004/005327, WO2004/005326, WO1998/13375, and WO2004/046170 and German Application Serial Nos. DE 100 08 089.8, the contents of which are incorporated herein in their entireties.

For example, tubulysin derivatives and/or analogs may be represented by Formula II:

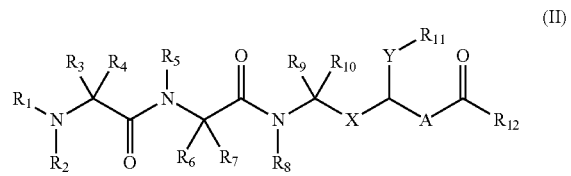

(II)

wherein
A is a substituted 5- or 6-membered heteroaryl;
X is O, S or $NR_{13}$ or $CR_{14}R_{15}$;
$X_a$ is O, S or $NR_a$;
Y is O, S or $NR_{16}$; and
$R_1$, $R_2$, $R_3$, $R_4$, $R_5$, $R_6$, $R_7$, $R_8$, $R_9$, $R_{10}$, $R_{13}$, $R_{14}$, $R_{15}$, $R_{16}$, and $R_a$ are independently H, alkyl, alkenyl, alkynyl, heteroalkyl, aryl, heteroaryl, cycloalkyl, alkylcycloalkyl, heteroalkylcycloalkyl, heterocycloalkyl, aralkyl or heteroaralkyl;

$R_{11}$ is H, alkyl, alkenyl, alkynyl, heteroalkyl, aryl, heteroaryl, cycloalkyl, alkylcycloalkyl, heteroalkylcycloalkyl, heterocycloalkyl, aralkyl, heteroaralkyl, —C(=O)-alkyl, —C(=O)-alkenyl, —C(=O)-alkynyl, —C(=O)-heteroalkyl, —C(=O)-aryl, —C(=O)-heteroaryl, —C(=O)-cycloalkyl, —C(=O)-alkylcycloalkyl, —C(=O)-heteroalkylcycloalkyl, —C(=O)-heterocycloalkyl, —C(=O)-aralkyl, or —C(=O)-heteroaralkyl;

$R_{12}$ is H, alkyl, alkenyl, alkynyl, heteroalkyl, aryl, heteroaryl, cycloalkyl, alkylcycloalkyl, heteroalkylcycloalkyl, heterocycloalkyl, aralkyl, heteroaralkyl, —$X_a$-alkyl, —$X_a$-alkenyl, —$X_a$-alkynyl, —$X_a$-heteroalkyl, —$X_a$-aryl, —$X_a$-heteroaryl, —$X_a$-cycloalkyl, —$X_a$-alkylcycloalkyl, —$X_a$-heteroalkylcycloalkyl, —$X_a$-heterocycloalkyl, —$X_a$-aralkyl, or —$X_a$-heteroaralkyl;

or two R's taken together form a cycloalkyl or heterocycloalkyl ring system;

or a pharmacologically acceptable salt, a solvate, a hydrate or a pharmacologically acceptable formulation thereof.

In some embodiments, tubulysin derivatives of Formula II are covalently attached to subject polymers through an occurrence of a functional group comprising one or more heteroatoms, for example, hydroxy, thiol, carboxy, amino, and amide groups, for example, when such groups occur in $R_{11}$ or $R_{12}$.

In certain embodiments, tubulysin derivatives and/or analogs of Formula II may be represented by Formula III:

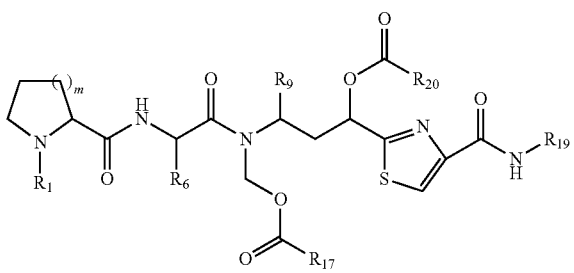

(III)

wherein
wherein $R_1$ represents $C_1$-$C_4$ alkyl;
$R_6$ represents $C_1$-$C_6$ alkyl;
$R_9$ represents $C_1$-$C_6$ alkyl;
$R_{17}$ represents $C_1$-$C_6$ alkyl or $C_1$-$C_6$ alkenyl;
$R_{19}$ represents aralkyl or heteroaralkyl;
$R_{20}$ represents $C_1$-$C_4$ alkyl; and
m equals 1 or 2.

In certain embodiments, $R_{19}$ represents the following structure:

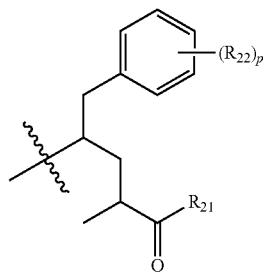

wherein
$R_{21}$ represents OH, $NH_2$, alkyloxy, alkyl amino or dialkyl amino;
$R_{22}$ represents halogen, OH, $NO_2$, $NH_2$, alkyloxy, alkyl amino or dialkyl amino; and
p equals 0, 1, 2 or 3.

In some embodiments, tubulysin derivatives of Formula III are covalently attached to subject polymers through an occurrence of a functional group comprising one or more heteroatoms, for example, hydroxy, thiol, carboxy, amino, and amide groups, such as the hydroxy or amino groups of $R_{21}$ or $R_{22}$.

In certain embodiments, tubulysin derivatives and/or analogs of Formula II may be represented by Formula IV:

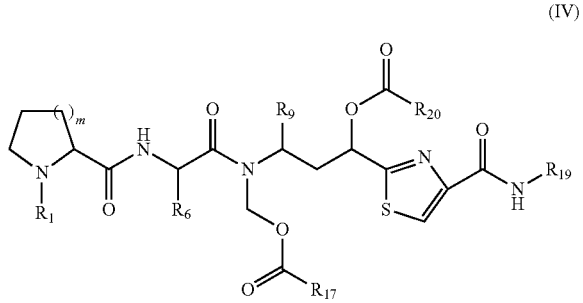

(IV)

wherein m represents 0, 1, 2, or 3;

$R_1$ represents methyl or ethyl;

$R_6$ represents isopropyl, isobutyl, ethyl, cyclopropyl, $CH_2$-cyclopropyl, or $CH(CH_3)CH_2CH_3$;

$R_9$ represents isopropyl, trifluoromethyl, chloromethyl, isobutyl, ethyl, cyclopropyl, $CH_2$-cyclopropyl, $CH(CH_3)CH_2CH_3$, cyclopentyl, or cyclohexyl;

$R_{17}$ represents methyl, ethyl, propyl, isopropyl, butyl, isobutyl, $CH=C(CH_3)$, cyclopropyl, cyclobutyl, or cyclohexyl;

$R_{20}$ represents methyl, ethyl, propyl, isopropyl, or phenyl; and $R_{19}$ represents

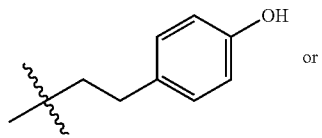

or

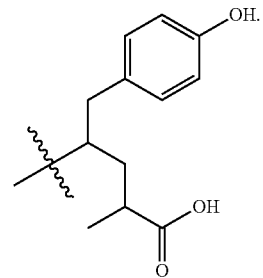

In some embodiments, tubulysin derivatives of Formula IV are covalently attached to subject polymers through an occurrence of a functional group comprising one or more heteroatoms, for example, hydroxy, thiol, carboxy, amino, and amide groups, such as the hydroxy or carboxy groups of $R_{19}$.

Further tubulysin derivatives and/or analogs may be represented by Formula V:

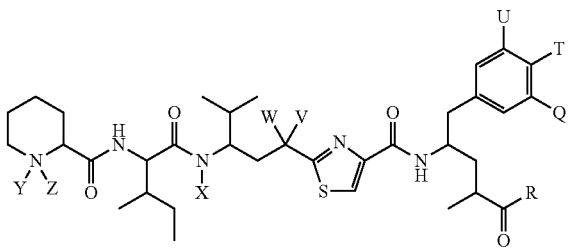

(V)

wherein

R represents H, alkyl, aryl, $OR_1$, $NR_1R_2$ or $NH(CH_2)_{2-4}$;

$R_1$ represents H, alkyl or aryl;

$R_2$ represents H, alkyl or aryl;

Q represents H, halogen, $NO_2$ or $NHR_3$;

U represents H, halogen, $NO_2$ or $NHR_3$;

$R_3$ represents H, HCO or $C_{1-4}$alkyl-CO;

T represents H, halogen, or $OR_4$, for example, T may represent H or $OR_4$;

$R_4$ represents H, alkyl, aryl, $COR_5$, $P(O)(OR_6)_2$ or $SO_3R_6$;

$R_5$ represents alkyl, alkenyl, aryl or heteroaryl;

$R_6$ represents H, alkyl or a metal ion;

V represents H, $OR_7$, halogen, or taken together with W represents =O;

$R_7$ represents H, alkyl or $COR_8$;

$R_8$ represents alkyl, alkenyl or aryl;

W represents H or alkyl, or taken together with V represents =O;

X represents H, alkyl, alkenyl, $CH_2NR_9$ or $CH_2OR_9$, for example, X may represent H, alkyl, alkenyl or $CH_2OR_9$;

$R_9$ represents H, alkyl, alkenyl, aryl or $COR_{10}$;

$R_{10}$ represents alkyl (e.g., methyl, ethyl, propyl, butyl (e.g., n-butyl, i-butyl), alkenyl (e.g., vinyl, dimethylvinyl), aryl or heteroaryl;

Y represents a free electron pair when Z represents $CH_3$ or $COR_{11}$, or O when Z represents $CH_3$;

$R_{11}$ represents alkyl, $CF_3$ or aryl; and

Z represents $CH_3$ when Y represents O or a free electron pair, or $COR_{11}$ when Y represents a free electron pair.

In some embodiments, tubulysin derivatives of Formula V are covalently attached to subject polymers through an occurrence of a functional group comprising one or more heteroatoms, for example, hydroxy, thiol, carboxy, amino, and amide groups, in some instances, through T or R.

Additional tubulysin derivatives of Formula V maybe represented by Formula Va:

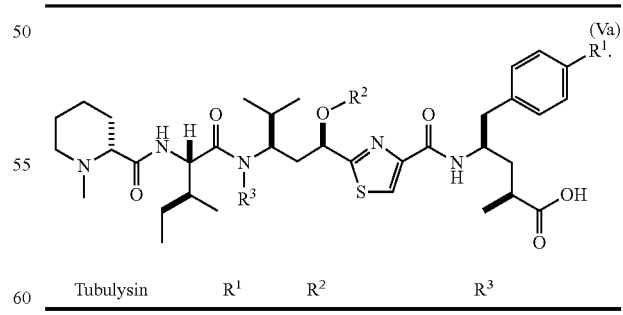

(Va)

| Tubulysin | $R^1$ | $R^2$ | $R^3$ |
|---|---|---|---|
| A | OH | Ac | $CH_2O—CO—CH_2CH(CH_3)_2$ |
| B | OH | Ac | $CH_2O—CO—CH_2CH_2CH_3$ |
| C | OH | Ac | $CH_2O—CO—CH_2CH_3$ |
| D | H | Ac | $CH_2O—CO—CH_2CH(CH_3)_2$ |
| E | H | Ac | $CH_2O—CO—CH_2CH_2CH_3$ |
| F | H | Ac | $CH_2O—CO—CH_2CH_3$ |
| G | OH | Ac | $CH_2O—CO—CH=C(CH_3)_2$ |

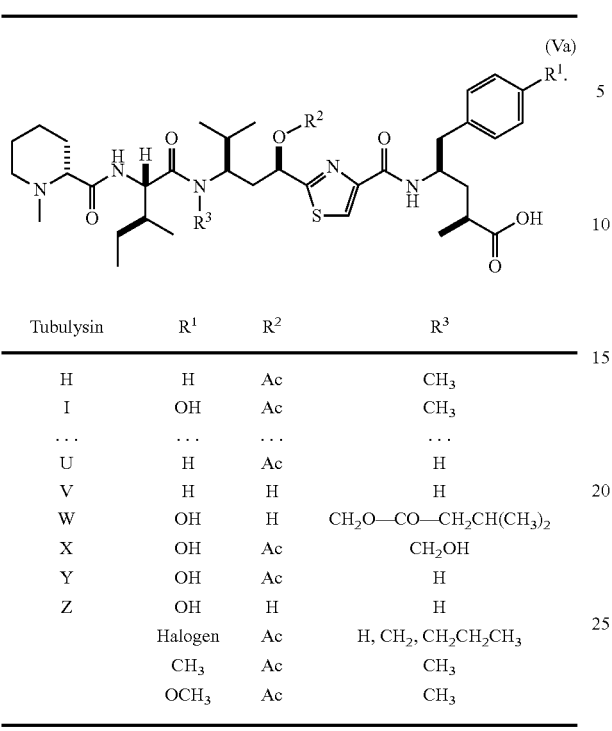

(Va)

| Tubulysin | R¹ | R² | R³ |
|---|---|---|---|
| H | H | Ac | $CH_3$ |
| I | OH | Ac | $CH_3$ |
| ... | ... | ... | ... |
| U | H | Ac | H |
| V | H | H | H |
| W | OH | H | $CH_2O-CO-CH_2CH(CH_3)_2$ |
| X | OH | Ac | $CH_2OH$ |
| Y | OH | Ac | H |
| Z | OH | H | H |
|  | Halogen | Ac | H, $CH_2$, $CH_2CH_2CH_3$ |
|  | $CH_3$ | Ac | $CH_3$ |
|  | $OCH_3$ | Ac | $CH_3$ |

In some embodiments, tubulysin derivatives of Formula Va are covalently attached to subject polymers through an occurrence of a functional group comprising one or more heteroatoms, for example, hydroxy, thiol, carboxy, amino, and amide groups, such as the carboxy group of Formula Va or $R^1$.

Further tubulysin derivatives and/or analogs may be represented by Formula VI:

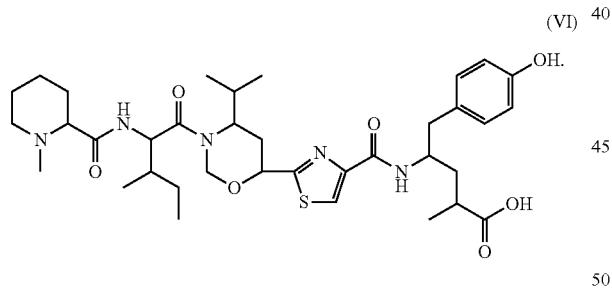

(VI)

In some embodiments, tubulysin derivatives of Formula VI are covalently attached to subject polymers through an occurrence of a functional group comprising one or more heteroatoms, for example, hydroxy, thiol, carboxy, amino, and amide groups, for example through the phenol group or the carboxy group depicted in Formula VI.

Additionally, epothilones and derivatives and/or analogs thereof may be found, for example, in PCT Publication Nos. WO2005/030767, WO2004/007492, WO2004/007483, and WO2002/32844 and German Application Serial Nos. DE 197 13 970.1, DE 100 51 136.8, DE 101 34 172.5, DE 102 32 094.2, the contents of which are incorporated herein in their entireties.

For example, epothilone derivatives and/or analogs may be represented by Formula VII:

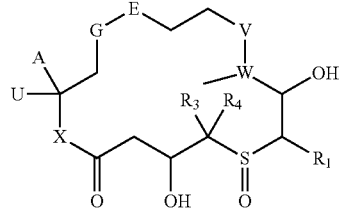

(VII)

wherein

A is a heteroalkyl, heterocycloalkyl, heteroalkylcycloalkyl, heteroaryl, heteroaralkenyl, or heteroaralkyl group;

U is hydrogen, halogen, an alkyl, heteroalkyl, heterocycloalkyl, heteroalkylcycloalkyl, heteroaryl or heteroaralkyl group;

G-E is selected from the following groups,

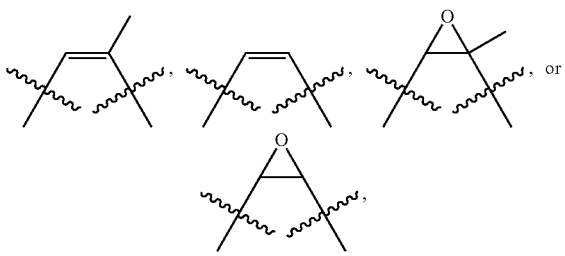

or is part of an optionally substituted phenyl ring;

$R_1$ is a $C_1$-$C_4$-alkyl, a $C_2$-$C_4$-alkenyl, a $C_2$-$C_4$-alkynyl, or a $C_3$-$C_4$-cycloalkyl group;

V—W is a group of formula $CH_2CH$ or $CH=C$;

X is oxygen or a group of the formula $NR_2$, wherein $R_2$ is hydrogen, an alkyl, alkenyl, alkynyl, heteroalkyl, aryl, heteroaryl, cycloalkyl, alkylcycloalkyl, heteroalkylcycloalkyl, heterocycloalkyl, aralkyl, or heteroaralkyl group; and $R_3$ and $R_4$ independently from each other represent hydrogen, $C_1$-$C_4$-alkyl or together are part of a cycloalkyl group with 3 or 4 ring atoms, or a pharmacologically acceptable salt, solvate, hydrate or formulation thereof;

or tautomers, geometrical isomers, or stereoisomers thereof.

In some embodiments, epothilone derivatives of Formula VII are covalently attached to subject polymers through an occurrence of a functional group comprising one or more heteroatoms, for example, hydroxy, thiol, carboxy, amino, and amide groups, for example, either of the hydroxy groups depicted in Formula VII.

In certain embodiments of Formula VII, A is a group of Formula VIII or IX,

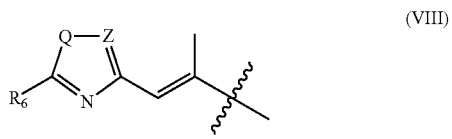

(VIII)

-continued

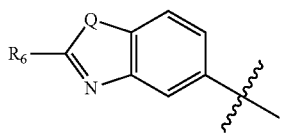
(IX)

wherein
Q is sulfur, oxygen or $NR_7$ (especially oxygen or sulfur), wherein $R_7$ is hydrogen, $C_1$-$C_4$ alkyl or $C_1$-$C_4$ heteroalkyl;
Z is nitrogen or CH (especially CH); and
$R_6$ is $OR_8$, $NHR_8$, $C_1$-$C_4$ alkyl, $C_1$-$C_4$ alkenyl, $C_1$-$C_4$ alkynyl or $C_1$-$C_6$ heteroalkyl (especially methyl, $CH_2OR_8$ or $CH_2NHR_8$), wherein $R_8$ is hydrogen, $C_1$-$C_4$ alkyl or $C_1$-$C_4$ heteroalkyl (especially hydrogen).

Further epothilone derivatives and/or analogs may be represented by Formula X:

(X)

wherein
$R_1$ is a $C_{1-6}$alkyl, a $C_{2-6}$alkynyl or a $C_{2-6}$alkenyl radical;
$R_2$ is a hydrogen atom or a $C_{1-6}$alkyl radical;
X—Y is selected from the following groups:

$R_3$ is a halogen atom or a $C_{1-6}$alkyl, a $C_{2-6}$alkenyl or a $C_{1-6}$-heteroalkyl radical;
$R_4$ is a bicycloaryl radical, a bicycloheteroaryl radical or a group of formula —C($R_5$)=CH$R_6$;
$R_5$ is a hydrogen atom or a methyl group; and
$R_6$ is an optionally substituted aryl or heteroaryl group;
or a pharmacologically acceptable salt, solvate, hydrate or a pharmacologically acceptable formulation thereof.

In certain embodiments, $R_4$ represents

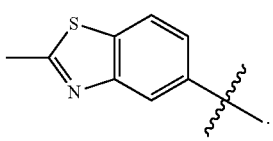 [SMILES: *c1ccc2sc(C)nc2c1]

In some embodiments, epothilone derivatives of Formula X are covalently attached to subject polymers through an occurrence of a functional group comprising one or more heteroatoms, for example, hydroxy, thiol, carboxy, amino, and amide groups, for example, either of the hydroxy groups depicted in Formula VII.

In certain embodiments, the compound of Formula X can be represented by the following structures:

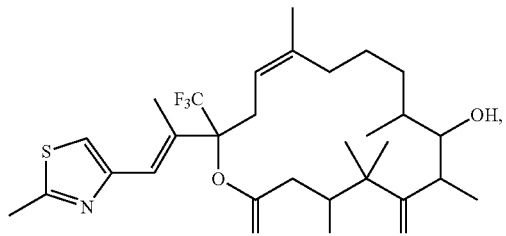

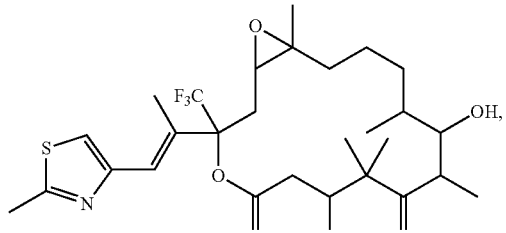

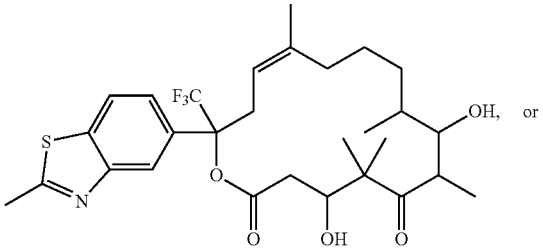

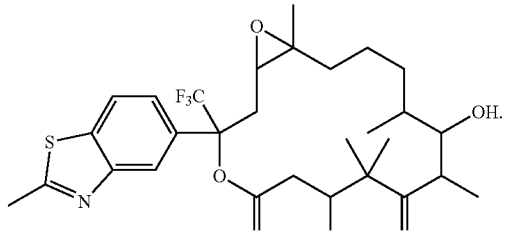

Further epothilone derivatives and/or analogs may be represented by Formula XI:

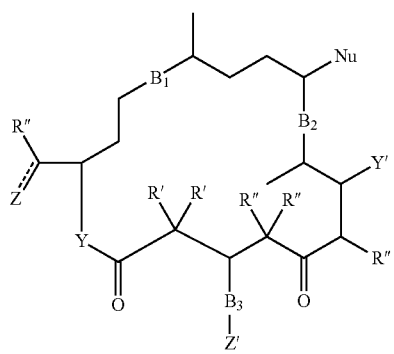
(XI)

wherein
$B_1$, $B_2$, $B_3$ are selected from single bonds; double bonds in the E(trans) form, Z(cis) form or as E/Z mixture; epoxide rings in the E(trans) form, Z(cis) form or E/Z mixture; cyclopropane rings in the E(trans) form, Z(cis) form or E/Z mixture; and/or combinations thereof; and being preferably selected from single and double bonds;

and particularly preferably being selected from $B_1$ as Z double bonds or epoxide and $B_2$ and $B_3$ as single bond;

R is selected from H; alkyl; aryl; aralkyl such as —$CH_2$-aryl, —$C_2H_4$-aryl and the like; alkenyl, such as vinyl; cycloalkyl, particularly a 3- to 7-membered cycloalkyl; $CH_nF_{3-n}$ with n=0 to 3; oxacycloalkyl, particularly a 3- to 7-membered oxacycloalkyl; and/or combinations thereof; being particularly selected from H, methyl, ethyl, phenyl, benzyl; and being particularly preferred selected from H, methyl, ethyl and combinations thereof;

R' is selected from the same group as R, and is preferably H;

R" is selected from the same group as R, and is preferably methyl;

Y is selected from S, NH, N-PG, NR and O; being preferably selected from NH, N-PG, NR and O, and being particularly preferably O;

Y' is selected from H, OH, OR, O-PG, $NH_2$, $NR_2$, $N(PG)_2$, SR and SH; being preferably O-PG and/or OH;

Nu is selected from R, O-PG, OR, $N(PG)_2$, $NR_2$, S-PG, SR, SeR, CN, $N_3$, aryl and heteroaryl; being preferably selected from R, O-PG, OR, $N(PG)_2$ and $NR_2$, and being particularly preferably H;

Z is selected from —OH, —O-PG, —OR, =O, =N-Nu, =CH-heteroaryl, =CH-aryl and =$PR_3$, where all previously mentioned double bound groups may be present in the E(trans) form, Z(cis) form or as E/Z mixture; being preferably =CH-heteroaryl; and being particularly preferred selected from .=O, (E)-(2-methylthiazol-4-yl)-CH= and (E)-(2-methyloxazol-4-yl)-CH=;

Z' is selected from O, OH, OR, O-PG, $N(H)_{1-2}$, $N(R)_{1-2}$, $N(PG)_{1-2}$, SR, S-PG and R; being preferably O, O-PG and/or OR;

$B_3$ is selected from single or double bonds in the E(trans) form, Z(cis) form or as E/Z mixture; being preferably selected from single and double bonds with heteroatoms such as O, S and N; and being particularly preferred a single bond to O-PG and/or OH;

PG is a protecting group, and is preferably selected from allyl, methyl, t-butyl (preferably with electron withdrawing group), benzyl, silyl, acyl and activated methylene derivatives such as methoxymethyl, alkoxyalkyl or 2-oxacycloalkyl; being preferably—predominantly for alcohol and amine functions—selected from trimethylsilyl, triethylsilyl, dimethyl-tert-butylsilyl, acetyl, propionyl, benzoyl, tetrahydropyranyl as well as protecting groups protecting neighbouring or bivalent groups ($PG_2$) concomitantly under formation of 5- to 7-membered rings, such as succinyl, phthalyl, methylene, ethylene, propylene, 2,2-dimethylpropa-1,3-diyl, acetonide; and/or combinations of all previously named protecting groups; alkyl is selected from hydrocarbons, also of branched isomers, preferably with $C_{1-20}$, particularly with 1 to 8 carbon atoms; aryl is selected from phenyl, naphthyl, benzyl, and their derivatives, preferably with up to five alkyl, alkoxy and/or halogen substituents, preferably from those with up to three substituents, particularly preferred with up to one substituent; preferably being selected from phenyl and benzyl derivatives; and combinations of these.

Hetaryl/heteroaryl is selected from five- or six-membered heteroaromatic moieties with one or more O, S and N atoms and their derivatives with up to four alkyl, alkoxy and/or halogen substituents, preferably from those with up to two substituents, particularly preferred with up to one substituent; preferably being selected from oxazole, thiazole and pyrimidine derivatives; and particularly preferred being an alkylthiazole derivative; and combinations thereof; with being particularly preferred Z=O, (E)-(2-methylthiazol-4-yl)-CH=, (E)-(2-methyloxazol-4-yl)-CH=; R'=H; R"=Me; Y', Z'=O-PG, OH and/or Y=O.

In some embodiments, epothilone derivatives of Formula XI are covalently attached to subject polymers through an occurrence of a functional group comprising one or more heteroatoms, for example, hydroxy, thiol, carboxy, amino, and amide groups, such as that of Y' or Z'.

In certain embodiments, derivatives and/or analogs of epothilone may be represented by Formula XII:

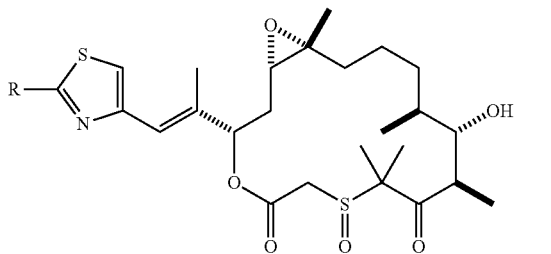

(XII)

wherein R is selected from $OR^1$, $NHR^1$, alkyl, alkenyl, alkynyl, and heteroalkyl (e.g., $CH_2OR^1$ or $CH_2NHR^1$); and $R^1$ is selected from hydrogen, $C_{1-4}$alkyl, and $C_{1-4}$heteroalkyl, preferably hydrogen.

In certain embodiments, R is selected from methyl, $CH_2OH$, and $CH_2NH_2$.

In some embodiments, epothilone derivatives of Formula XII are covalently attached to subject polymers through an occurrence of a functional group comprising one or more heteroatoms, for example, hydroxy, thiol, carboxy, amino, and amide groups, for example, the hydroxy group depicted in Formula XII.

In certain embodiments, the selectivity-determining moiety may be GFLG or KF or FK, the self-cyclizing moiety may be an imidazolidone-forming moiety, and the therapeutic agent may be a hydroxyl-containing agent, including, but not limited to, etoposide. The cascade to release etoposide for GFLG, for example, may be illustrated as shown below.

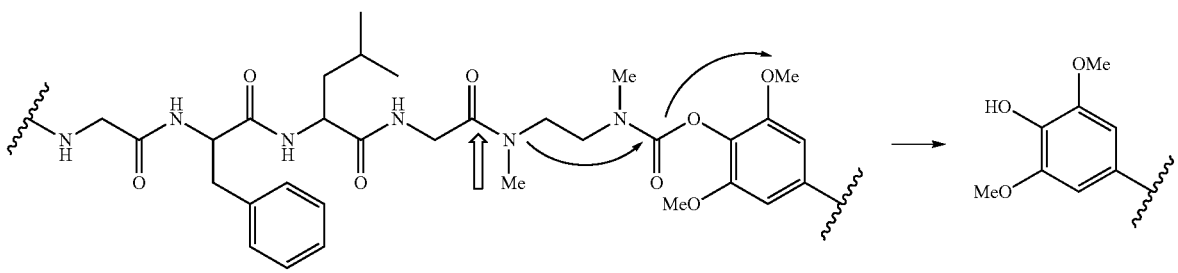 [SMILES: *NCC(=O)NC(Cc1ccccc1)C(=O)NC(CC(C)C)C(=O)NCC(=O)N(C)CCN(C)C(=O)Oc1c(OC)cc(*)cc1OC ; *c1cc(OC)c(O)c(OC)c1]

A similar cascade is contemplated when KF or FK is used in place of GFLG as the selectivity-determining moiety.

In certain embodiments, the selectivity-determining moiety may be cis-aconityl, the self-cyclizing moiety may be an imidazolidone-forming moiety, and the therapeutic agent may be a hydroxyl-containing agent, including, but not limited to, etoposide. The cascade to release etoposide may be illustrated as shown below, wherein either isoform of cis-aconityl may be used.

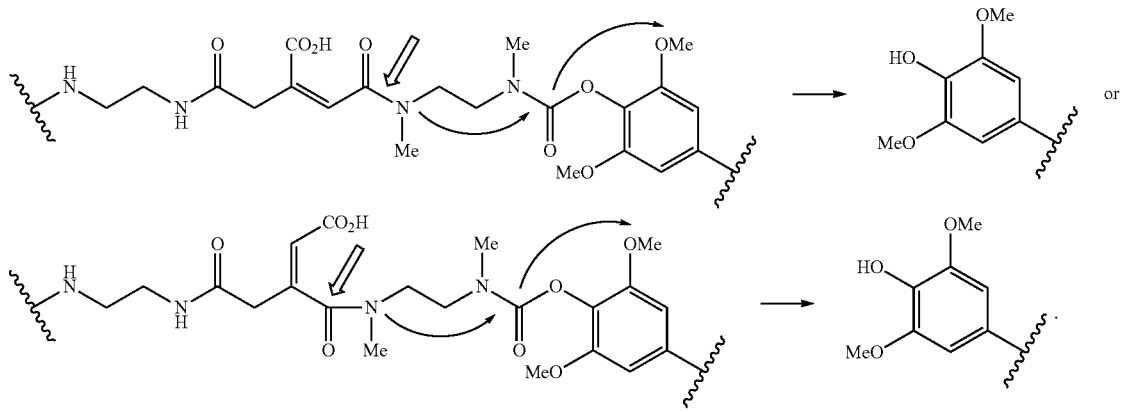

In certain embodiments, the selectivity-determining moiety may be cleavable under basic conditions, the self-cyclizing moiety may be an imidazolidone-forming moiety, and the therapeutic agent may be a hydroxyl-containing agent, including, but not limited to, etoposide. The cascade to release etoposide may be illustrated as shown below.

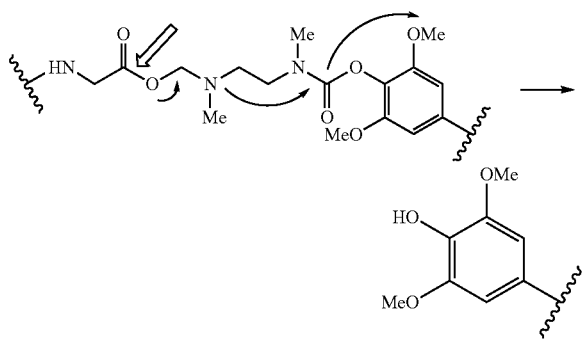

In certain embodiments, the present invention contemplates a linear, water-soluble, cyclodextrin-containing polymer, wherein a plurality of therapeutic agents are covalently attached to the polymer through attachments that are cleaved under biological conditions to release the therapeutic agents as discussed above, wherein administration of the polymer to a patient results in release of the therapeutic agent over a period of at least 2, 3, 5, 6, 8, 10, 15, 20, 24, 36, 48 or even 72 hours.

One embodiment of the present invention provides an improved delivery of certain hydrophobic small molecule therapeutics by covalently conjugating them to cyclodextrin-containing polymers as discussed above. Such conjugation improves the aqueous solubility and hence the bioavailability of the therapeutic agents. Accordingly, in one embodiment of the invention, the therapeutic agent is a hydrophobic compound with a log $P > 0.4$, $> 0.6$, $> 0.8$, $> 1$, $> 2$, $> 3$, $> 4$, or even $> 5$.

The polymer conjugates of the present invention preferably have molecular weights in the range of 10,000 to 500,000; 30,000 to 200,000; or even 70,000 to 150,000 amu.

In certain embodiments, the cyclodextrin moieties make up at least about 2%, 5% or 10% by weight, up to 20%, 30%, 50% or even 80% of the cyclodextrin-modified polymer by weight. In certain embodiments, the therapeutic agents, or targeting ligands make up at least about 1%, 5%, 10% or 15%, 20%, 25%, 30% or even 35% of the cyclodextrin-modified polymer by weight. Number-average molecular weight ($M_n$) may also vary widely, but generally fall in the range of about 1,000 to about 500,000 daltons, preferably from about 5000 to about 200,000 daltons and, even more preferably, from about 10,000 to about 100,000. Most preferably, $M_n$ varies between about 12,000 and 65,000 daltons. In certain other embodiments, $M_n$ varies between about 3000 and 150,000 daltons. Within a given sample of a subject polymer, a wide range of molecular weights may be present. For example, molecules within the sample may have molecular weights that differ by a factor of 2, 5, 10, 20, 50, 100, or more, or that differ from the average molecular weight by a factor of 2, 5, 10, 20, 50, 100, or more. Exemplary cyclodextrin moieties include cyclic structures consisting essentially of from 7 to 9 saccharide moieties, such as cyclodextrin and oxidized cyclodextrin. A cyclodextrin moiety optionally comprises a linker moiety that forms a covalent linkage between the cyclic structure and the polymer backbone, preferably having from 1 to 20 atoms in the chain, such as alkyl chains, including dicarboxylic acid derivatives (such as glutaric acid derivatives, succinic acid derivatives, and the like), and heteroalkyl chains, such as oligoethylene glycol chains.

In certain embodiments, the present invention contemplates attenuating the rate of release of the therapeutic agent by introducing various tether groups between the therapeutic agent and the polymer. Thus, in certain embodiments, the polymeric therapeutics of the present invention are compositions for controlled delivery of therapeutic agents. One skilled in the art would also recognize that by labeling the therapeutic agent and/or targeting ligand with radionuclei, or by forming complexes of NMR active nuclei, e.g., technetium, gadolinium, or dysprosium, the polymers of the present invention can achieve a dual diagnostic/therapeutic utility.

In other embodiments, the polymeric compounds stabilize the bioactive form of a therapeutic agent which exists in equilibrium between an active and inactive form. For instance, conjugating the therapeutic agent to the polymers of the present invention may shift the equilibrium between two tautomeric forms of the agent to the bioactive tautomer. In other embodiment, the polymeric compounds may attenuate the equilibrium between lactonic and acid forms of a therapeutic agent.

One method to determine molecular weight is by gel permeation chromatography ("GPC"), e.g., mixed bed columns, $CH_2Cl_2$ solvent, light scattering detector, and off-line dn/dc. Other methods are known in the art.

In other embodiments, the polymer conjugate of the invention may be a flexible or flowable material. When the polymer used is itself flowable, the polymer composition of the invention, even when viscous, need not include a biocompatible solvent to be flowable, although trace or residual amounts of biocompatible solvents may still be present.

While in certain embodiments the biodegradable polymer or the therapeutic agent may be dissolved in a small quantity of a non-toxic solvent to more efficiently produce an amorphous, monolithic distribution or a fine dispersion of the biologically active agent in the flexible or flowable composition, in certain preferred embodiments, no solvent is required to form a flowable composition. In certain embodiments where a solvent is used to facilitate mixing or to maintain the flowability of the polymer conjugate of the invention, it is preferably non-toxic and otherwise biocompatible, and preferably used in relatively small amounts.

Examples of suitable biocompatible solvents, include, but are not limited to, N-methyl-2-pyrrolidone, 2-pyrrolidone, ethanol, propylene glycol, acetone, methyl acetate, ethyl acetate, methyl ethyl ketone, dimethylformamide, dimethylsulfoxide, tetrahydrofuran, caprolactam, oleic acid, or 1-dodecylazacylcoheptanone. Preferred solvents include N-methylpyrrolidone, 2-pyrrolidone, dimethylsulfoxide, and acetone because of their solvating ability and their biocompatibility.

In certain embodiments, the subject polymer conjugates are soluble in one or more common organic solvents for ease of fabrication and processing. Common organic solvents include, but are not limited to, chloroform, dichloromethane, dichloroethane, 2-butanone, butyl acetate, ethyl butyrate, acetone, ethyl acetate, dimethylacetamide, N-methylpyrrolidone, dimethylformamide, and dimethylsulfoxide.

II. Targeting Ligand

In certain embodiments, the polymer conjugate comprises a targeting ligand. Thus in certain embodiments, a receptor, cell, and/or tissue-targeting ligand, or a precursor thereof is coupled to a polymer conjugate.

As used herein the term "targeting ligand" refers to any material or substance which may promote targeting of receptors, cells, and/or tissues in vivo or in vitro with the compositions of the present invention. The targeting ligand may be synthetic, semi-synthetic, or naturally-occurring. Materials or substances which may serve as targeting ligands include, but are not limited to, proteins, including antibodies, antibody fragments, hormones, hormone analogues, glycoproteins and lectins, peptides, polypeptides, amino acids, sugars, saccharides, including monosaccharides and polysaccharides, carbohydrates, small molecules, vitamins, steroids, steroid analogs, hormones, cofactors, bioactive agents, and genetic material, including nucleosides, nucleotides, nucleotide acid constructs and polynucleotides.

As indicated above, in certain instances, the targeting ligand may be a hormone, for example a hormone that facilitates endocytosis, such as receptor-mediated endocytosis. Such endocytosis may occur with regard to the present polymer conjugates in various structural forms thereof, such as microspheres, microparticles, and nanoparticles. The endocytosis may facilitate cellular uptake of the present polymer conjugates. In certain embodiments, the targeting ligand may be luteinizing hormone-releasing hormone (LHRH). For example, targeting ligands, such as hormones, such as LHRH, may be used in the subject polymer conjugates in combination with therapeutic agents and analogs or derivatives thereof as described herein, such as epothilones and tubulysins and analogs or derivatives thereof. In some embodiments, use of a hormone, such as LHRH, as a targeting ligand increases the cellular uptake of the present polymer conjugates in cells exhibiting abnormal proliferation, such as in cancer and/or tumor cells. For example, use of a hormone, such as LHRH, as a targeting ligand can be used to increase cellular uptake of the present polymer conjugates in breast, lung, colon, and ovarian cancer cells.

As used herein, the term "precursor" to a targeting ligand refers to any material or substance which may be converted to a targeting ligand. Such conversion may involve, for example, anchoring a precursor to a targeting ligand. Exemplary targeting precursor moieties include maleimide groups, disulfide groups, such as ortho-pyridyl disulfide, vinylsulfone groups, azide groups, and α-iodo acetyl groups. The attachment of the targeting ligand or precursor thereof to the polymer may be accomplished in various ways including, but not limited to chelation, covalent attachment, or formation of host-guest complexes. In certain embodiments, an optional linker group may be present between the targeting ligand or precursor thereof and the polymer, wherein the linker group is attached to the polymer via chelation, covalent attachment or form host guest complexes. For example, the one terminal end of a linker group may be attached to the targeting ligand while the other may be attached to an adamantane group, or other such hydrophobic moiety, which forms a host guest complex with a cyclodextrin moiety. Thus the targeting ligand may be attached to a grafted cyclodextrin moiety, to a cyclodextrin moiety within the polymeric chain, or to the polymeric chain itself. The number of targeting ligands per polymeric chain may vary according to various factors including but not limited to the identity of the therapeutic agent, nature of the disease, type of polymer chain. Structures of possible linker groups are the same as linker groups defined elsewhere in this application.

III. Definitions

The term "active" as used herein means biologically, therapeutically or pharmacologically active.

An "adjuvant", as the term is used herein, is a compound that has little or no therapeutic value on its own, but increases the effectiveness of a therapeutic agent. Exemplary adjuvants include radiosensitizers, transfection-enhancing agents (such as chloroquine and analogs thereof), chemotactic agents and chemoattractants, peptides that modulate cell adhesion and/or cell mobility, cell permeabilizing agents, inhibitors of multidrug resistance and/or efflux pumps, etc.

The term "agonist", as used herein, is meant to refer to an agent that mimics or up-regulates (e.g., potentiates or supplements) the bioactivity of a protein of interest, or an agent that facilitates or promotes (e.g., potentiates or supplements) an interaction among polypeptides or between a polypeptide and another molecule (e.g., a steroid, hormone, nucleic acids, small molecules etc.). An agonist can be a wild-type protein or derivative thereof having at least one bioactivity of the wild-type protein. An agonist can also be a small molecule that up-regulates the expression of a gene or which increases at least one bioactivity of a protein. An agonist can also be a protein or small molecule which increases the interaction of a polypeptide of interest with another molecule, e.g., a target peptide or nucleic acid.

"Antagonist" as used herein is meant to refer to an agent that down-regulates (e.g., suppresses or inhibits) the bioactivity of a protein of interest, or an agent that inhibits/suppresses or reduces (e.g., destabilizes or decreases) interaction among polypeptides or other molecules (e.g., steroids, hormones, nucleic acids, etc.). An antagonist can also be a compound that down-regulates the expression of a gene of interest or which reduces the amount of the wild-type protein present. An antagonist can also be a protein or small molecule which decreases or inhibits the interaction of a polypeptide of interest with another molecule, e.g., a target peptide or nucleic acid.

The terms "biocompatible polymer" and "biocompatibility" when used in relation to polymers are art-recognized. For example, biocompatible polymers include polymers that are neither themselves toxic to the host (e.g., an animal or human), nor degrade (if the polymer degrades) at a rate that produces monomeric or oligomeric subunits or other byproducts at toxic concentrations in the host. In certain embodiments of the present invention, biodegradation generally involves degradation of the polymer in an organism, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible. Hence, a subject composition may comprise 99%, 98%, 97%, 96%, 95%, 90% 85%, 80%, 75% or even less of biocompatible polymers, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1 M NaOH at 37° C. until complete degradation is observed. The solution is then neutralized with 1 M HCl. About 200 µL of various concentrations of the degraded sample products are placed in 96-well tissue culture plates and seeded with human gastric carcinoma cells (GT3TKB) at 104/well density. The degraded sample products are incubated with the GT3TKB cells for 48 hours. The results of the assay may be plotted as % relative growth vs. concentration of degraded sample in the tissue-culture well. In addition, polymers and formulations of the present invention may also be evaluated by well-known in vivo tests, such as subcutaneous implantations in rats to confirm that they do not cause significant levels of irritation or inflammation at the subcutaneous implantation sites.

The term "biodegradable" is art-recognized, and includes polymers, compositions and formulations, such as those described herein, that are intended to degrade during use. Biodegradable polymers typically differ from non-biodegradable polymers in that the former may be degraded during use. In certain embodiments, such use involves in vivo use, such as in vivo therapy, and in other certain embodiments, such use involves in vitro use. In general, degradation attributable to biodegradability involves the degradation of a biodegradable polymer into its component subunits, or digestion, e.g., by a biochemical process, of the polymer into smaller, non-polymeric subunits. In certain embodiments, two different types of biodegradation may generally be identified. For example, one type of biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. In contrast, another type of biodegradation may involve cleavage of a bond (whether covalent or otherwise) internal to sidechain or that connects a side chain to the polymer backbone. For example, a therapeutic agent or other chemical moiety attached as a side chain to the polymer backbone may be released by biodegradation. In certain embodiments, one or the other or both general types of biodegradation may occur during use of a polymer.

As used herein, the term "biodegradation" encompasses both general types of biodegradation. The degradation rate of a biodegradable polymer often depends in part on a variety of factors, including the chemical identity of the linkage responsible for any degradation, the molecular weight, crystallinity, biostability, and degree of cross-linking of such polymer, the physical characteristics (e.g., shape and size) of an implant, and the mode and location of administration. For example, the greater the molecular weight, the higher the degree of crystallinity, and/or the greater the biostability, the biodegradation of any biodegradable polymer is usually slower. The term "biodegradable" is intended to cover materials and processes also termed "bioerodible".

In certain embodiments wherein the biodegradable polymer also has a therapeutic agent or other material associated with it, the biodegradation rate of such polymer may be characterized by a release rate of such materials. In such circumstances, the biodegradation rate may depend on not only the chemical identity and physical characteristics of the polymer, but also on the identity of material(s) incorporated therein. Degradation of the subject compositions includes not only the cleavage of intramolecular bonds, e.g., by oxidation and/or hydrolysis, but also the disruption of intermolecular bonds, such as dissociation of host/guest complexes by competitive complex formation with foreign inclusion hosts.

In certain embodiments, polymeric formulations of the present invention biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 and 8 having a temperature of between 25 and 37° C. In other embodiments, the polymer degrades in a period of between about one hour and several weeks, depending on the desired application.

As used herein the term "bioerodable" refers to polymers which deliver sustained effective amounts of therapeutic agent to target tissue over desired extended periods of time. Thus, a polymer according to the invention in the biological environment of host tissue and the like, in one aspect, is subjected to hydrolytic enzymes and oxidative species under, and in proportion to, the host's inflammatory response. This results in release of the therapeutic agent via the breaking of the covalent linked bonds. Thus, in certain embodiments, the materials of the invention utilize the mammal's own wound-healing repair process in being degraded thereby, as hereinbefore described.

The biodegradable polymers polylactic acid, polyglycolic acid, and polylactic-glycolic acid copolymer (PLGA), have been investigated extensively for nanoparticle formulation. These polymers are polyesters that, upon implantation in the body, undergo simple hydrolysis. The products of such hydrolysis are biologically compatible and metabolizable moieties (e.g., lactic acid and glycolic acid), which are eventually removed from the body by the citric acid cycle. Polymer biodegradation products are formed at a very slow rate, and hence do not affect normal cell function. Several implant studies with these polymers have proven safe in drug delivery applications, used in the form of matrices, microspheres, bone implant materials, surgical sutures, and also in contraceptive applications for long-term effects. These polymers are also used as graft materials for artificial organs, and recently as basement membranes in tissue engineering investigations. Nature Med. 824-826 (1996). Thus, these polymers have been time-tested in various applications and proven safe for human use. Most importantly, these polymers are FDA-approved for human use.

When polymers are used for delivery of pharmacologically active agents in vivo, it is essential that the polymers themselves be nontoxic and that they degrade into non-toxic degradation products as the polymer is eroded by the body fluids. Many synthetic biodegradable polymers, however, yield oligomers and monomers upon erosion in vivo that adversely interact with the surrounding tissue. D. F. Williams, J. Mater. Sci. 1233 (1982). To minimize the toxicity of the intact polymer carrier and its degradation products, polymers have been designed based on naturally occurring metabolites. Probably the most extensively studied examples of such polymers are the polyesters derived from lactic or glycolic acid and polyamides derived from amino acids.

A number of bioerodable or biodegradable polymers are known and used for controlled release of pharmaceuticals. Such polymers are described in, for example, U.S. Pat. Nos. 4,291,013, 4,347,234, 4,525,495, 4,570,629, 4,572,832, 4,587,268, 4,638,04, 4,675,381, 4,745,160, and 5,219,980, which are incorporated herein in their entirety.

A biohydrolyzable bond (e.g., ester, amide, carbonate, carbamates, or imide) refers to a bond that is cleaved (e.g., an ester is cleaved to form a hydroxyl and a carboxylic acid) under physiological conditions. Physiological conditions include the acidic and basic environments of the digestive tract (e.g., stomach, intestines, etc.), acidic environment of a tumor, enzymatic cleavage, metabolism, and other biological processes, and preferably refer to physiological conditions in a vertebrate, such as a mammal.

Upon copolymerization of a comonomer precursor with a cyclodextrin monomer precursor, two cyclodextrin monomers may be linked together by joining the primary hydroxyl side of one cyclodextrin monomer with the primary hydroxyl side of another cyclodextrin monomer, by joining the secondary hydroxyl side of one cyclodextrin monomer with the secondary hydroxyl side of another cyclodextrin monomer, or by joining the primary hydroxyl side of one cyclodextrin monomer with the secondary hydroxyl side of another cyclodextrin monomer. Accordingly, combinations of such linkages may exist in the final copolymer. Both the comonomer A precursor and the comonomer A of the final copolymer may be neutral, cationic (for example quaternary ammonium groups), or anionic (for example sulfate, phosphate, borinate or carboxylate) groups. The charge of comonomer A of the copolymer may be adjusted by adjusting pH conditions. Examples of suitable comonomer A precursors include, but are not limited to succinimide (e.g., dithiobis(succinimidyl propionate) DSP, and dissucinimidyl suberate (DSS)), glutamates, and aspartates).

The cyclodextrin-containing polymers of the present invention may be linear, branched or grafted. As used herein, the term "linear cyclodextrin-containing polymer" refers to a polymer comprising ($\alpha$, $\beta$, or $\gamma$) cyclodextrin molecules, or derivatives thereof which are inserted within a polymer chain. As used herein, the term "grafted cyclodextrin-containing polymer" refers to a polymer comprising ($\alpha$, $\beta$, or $\gamma$) cyclodextrin molecules, or derivatives thereof which are pendant off of the polymer chain. The term "graft polymer" as used herein refers to a polymer molecule which has additional moieties attached as pendent groups along a polymer backbone. The term "graft polymerization" denotes a polymerization in which a side chain is grafted onto a polymer chain, which side chain consists of one or several other monomers. The properties of the graft copolymer obtained such as, for example, solubility, melting point, water absorption, wettability, mechanical properties, adsorption behavior, etc., deviate more or less sharply from those of the initial polymer as a function of the type and amount of the grafted monomers. The term "grafting ratio", as used herein, means the weight percent of the amount of the monomers grafted based on the weight of the polymer. As used herein, a branched cyclodextrin-containing polymer refers to a polymer backbone with a plurality of branch points, wherein each branch point is a starting point of yet another strand of the polymer backbone, and each section of polymer backbone may have a plurality of ($\alpha$, $\beta$, or $\gamma$) cyclodextrin molecules, or derivatives thereof, inserted into or grafted onto the chain.

The phrase "controlled release" or "sustained release" refers to the use of systems that allow for the controlled or tunable delivery of one or more of the present compounds or compositions over time. For example, in certain instances, the present compounds or compositions are used in conjunction with a controlled release system that delivers an effective amount (such as an approximately continuous amount, an increasing amount, or a decreasing amount) of the compound(s) over a certain period of time, for example, over a period of at least about 4, 8, 12, 24, 48, or 72 hours, over a period of at least about 1, 2, 3, 4, or 5 days, over a period of at least about 1, 2, or 3 weeks, or over a period of at least about 1, 2, 3, 4, 5, or 6 months. Such controlled release systems may be used in conjunction with medical devices, such as stents and catheters, to provide medical devices which offer controlled release of the present compounds and/or compositions. By way of example, some suitable controlled release systems include hydrogels, polymers, meshes, and others demonstrated in the art.

The term "cyclodextrin moiety" refers to ($\alpha$, $\beta$, or $\gamma$) cyclodextrin molecules or derivatives thereof, which may be in their oxidized or reduced forms. Cyclodextrin moieties may comprise optional linkers. Optional therapeutic agents and/or targeting ligands may be further linked to these moieties via an optional linker. The linkage may be covalent (optionally via biohydrolyzable bonds, e.g., esters, amides, carbamates, and carbonates) or may be a host-guest complex between the cyclodextrin derivative and the therapeutic agent and/or targeting ligand or the optional linkers of each. Cyclodextrin moieties may further include one or more carbohydrate moieties, preferably simple carbohydrate moieties such as galactose, attached to the cyclic core, either directly (i.e., via a carbohydrate linkage) or through a linker group.

As used herein, the term "$EC_{50}$" means the concentration of a drug that produces 50% of its maximum response or effect.

The term "$ED_{50}$" means the dose of a drug that produces 50% of its maximum response or effect.

An "effective amount" of a subject compound, with respect to the subject method of treatment, refers to an amount of the therapeutic in a preparation which, when applied as part of a desired dosage regimen provides a benefit according to clinically acceptable standards for the treatment or prophylaxis of a particular disorder.

As used herein the term "low aqueous solubility" refers to water insoluble compounds having poor solubility in water, that is <5 mg/ml at physiological pH (6.5-7.4). Preferably, their water solubility is <1 mg/ml, more preferably <0.1 mg/ml. It is desirable that the drug is stable in water as a dispersion; otherwise a lyophilized or spray-dried solid form may be desirable.

A "patient" or "subject" to be treated by the subject method can mean either a human or non-human subject.

The "polymerizations" of the present invention include radical, anionic, and cationic mechanisms, as well as reactions of bifunctional molecules (analogous to the formation of nylon, e.g., reacting molecules each of which bears two or more different reactive moieties that react with each other (but, preferably, are disfavored from reacting intramolecularly by steric, conformational, or other constraints), or reacting two or more different compounds, each compound bearing two or more reactive moieties that react only with reactive moieties of different compounds (i.e., intermolecularly)), as well as metal-catalyzed polymerizations such as olefin metathesis, and other polymerization reactions known to those of skill in the art.

The terms "prophylactic" and "therapeutic" are art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e., it is intended to diminish, ameliorate, or stabilize the existing unwanted condition or side effects thereof).

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the frequency of, or alternatively delaying, pain sensations experienced by subjects in a treated population versus an untreated control population.

The term "small molecule" refers to a compound having a molecular weight less than about 2500 amu, preferably less than about 2000 amu, even more preferably less than about 1500 amu, still more preferably less than about 1000 amu, or most preferably less than about 750 amu.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents may include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. Unless specifically indicated as unsubstituted, all occurrences of moieties bearing one or more C—H bonds may be either unsubstituted or substituted as defined herein. By way of example, a reference to an "alkyl" or "aryl" group will be understood to include unsubstituted or substituted variants thereof.

As used herein, the terms "therapeutic agent" includes any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. More particularly, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

A "therapeutically effective amount" of a compound, with respect to a method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

"Physiological conditions" describe the conditions inside an organism, i.e., in vivo. Physiological conditions include the acidic and basic environments of body cavities and organs, enzymatic cleavage, metabolism, and other biological processes, and preferably refer to physiological conditions in a vertebrate, such as a mammal.

The term "physiological pH," as used herein, refers to a pH that is about 7.4 at the standard physiological temperature of 37.4° C. The term "non-physiological pH," as used herein, refers to a pH that is less than or greater than "physiological pH," preferably between about 4 and 7.3, or greater than 7.5 and less than about 12. The term "neutral pH," as used herein, refers to a pH of about 7. In preferred embodiments, physiological pH refers to pH 7.4, and non-physiological pH refers to pH between about 6 and 7. The term "acidic pH" refers to a pH that is below pH 7, preferably below about pH 6, or even below about pH 4.

The term "prodrug" is intended to encompass compounds which, under physiological conditions, are converted into the therapeutically active agents of the present invention. A common method for making a prodrug is to include selected moieties which are hydrolyzed under physiological conditions to reveal the desired molecule. In other embodiments, the prodrug is converted by an enzymatic activity of the host animal.

As used herein, "proliferating" and "proliferation" refer to cells undergoing mitosis.

The term "acyl" is art-recognized and refers to a group represented by the general formula hydrocarbylC(O)—, preferably alkylC(O)—.

The term "acyloxy" is art-recognized and refers to a group represented by the general formula hydrocarbylC(O)O—, preferably alkylC(O)O—.

The term "alkoxyalkyl" refers to an alkyl group substituted with an alkoxy group and may be represented by the general formula alkyl-O-alkyl.

The terms "alkenyl" and "alkynyl" refer to unsaturated aliphatic groups analogous in length and possible substitution to the alkyls described below, but that contain at least one double or triple bond respectively.

The term "alkoxy" refers to an alkyl group having an oxygen attached thereto. Representative alkoxy groups include methoxy, ethoxy, propoxy, tert-butoxy and the like.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2, 2-trifluoroethyl, etc.

The term "$C_{x-y}$" when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylcycloalkyl" refers to groups, which contain cycloalkyl as well as alkyl, alkenyl or alkynyl groups according to the above definition, e.g. alkylcycloalkyl, alkylcycloalkenyl, alkenylcycloalkyl and alkynylcycloalkyl groups, etc. Preferentially a alkylcycloalkyl group is composed of a cycloalkyl group, comprising one or more rings, comprising three to ten, preferentially three, four, five, six or seven carbon-atoms and one or two alkyl, alkenyl, or alkynyl groups with one or two to six carbon atoms.

The term "alkylthio", as used herein, refers to a thiol group substituted with an alkyl group and may be represented by the general formula alkyl-S—.

The term "amide" or "amido," as used herein, refers to a group

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

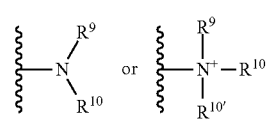

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "amidine" denotes the group —C(NH)—NHR wherein R is H or alkyl or aralkyl. A preferred amidine is the group —C(NH)—NH$_2$.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

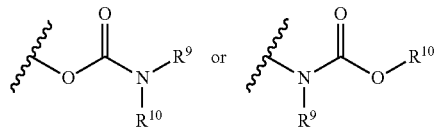

wherein $R^9$ and $R^{10}$ independently represent hydrogen or a hydrocarbyl group.

The term "carbonate" is art-recognized and refers to a group —OCO2-.

The term "carboxy", as used herein, refers to a group represented by the formula CO2H.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbonyl" is art-recognized and includes such moieties as may be represented by the general formula:

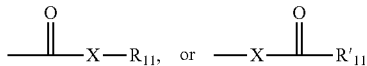

wherein X is a bond or represents an oxygen or a sulfur, and $R_{11}$ represents a hydrogen, an alkyl, an alkenyl, —(CH$_2$)$_m$—R$_8$ or a pharmaceutically acceptable salt, $R'_{11}$ represents a hydrogen, an alkyl, an alkenyl or —(CH$_2$)$_m$—R$_8$, where m and R$_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "cycloalkyl" refers to a saturated or partially unsaturated (e.g. cycloalkenyl) cyclic group, comprising one or several rings, preferentially one or two, containing three to fourteen ring carbon atoms, preferentially three to ten, preferentially three, four, five, six or seven ring carbon atoms. Furthermore the term cycloalkyl refers to a group where one or more hydrogen atoms are replaced by F, Cl, Br, I, OH, =O, SH, =S, NH$_2$, =NH, or NO$_2$, or cyclic ketones, for example cyclohexanone, 2-cyclohexenone or cyclopentanone. Examples of cycloalkyl groups are cyclopropyl, cyclobutyl, cyclopentenyl, spiro[4,5]-decanyl, norbornyl, cyclohexyl, cyclopentenyl, cyclohexadienyl, decalinyl, cubanyl, bicyclo[4.3.0]nonyl, tetralin, cyclopentylcyclohexyl, fluor-cyclohexyl or the cyclohex-2-enyl group.

The term "ester", as used herein, refers to a group —C(O)OR$^9$ wherein R$^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a heteroaryl group.

The terms "hetaralkenyl" and "heteroaralkenyl", as used herein, refers to an alkenyl group substituted with a heteroaryl group.

The term "heteroalkyl" refers to a alkyl, alkenyl or alkynyl group, where several, preferentially one, two or three carbon atoms are replaced by a O, N, P, B, Se, Si, or S atom, preferentially O, S, N. The term heteroalkyl also includes a carboxylic acid or a thereof derived group, for example acyl (alkyl-CO), acylalkyl, alkoxycarbonyl, acyloxy, acyloxyalkyl, carboxyalkylamid or alkoxycarbonyloxy.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings may be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heteroalkylcycloalkyl" refers to alkylcycloalkyl groups, according to the above definition, wherein one or several, preferentially one, two or three carbon atoms are replaced by O, N, Si, Se, P or S, preferentially O, S, N. In certain instances a heteroakylcycloalkyl group comprises one or two ring systems with three to ten, preferentially three, four, five, six or seven ring atoms and one or two alkyl, alkenyl, alkynyl or heteroalkyl groups with one or two to six carbon atoms. Examples of such a group are alkylheterocycloalkyl, alkylheterocycloalkenyl, alkenyl-heterocycloalkyl, alkynylheterocycloalkyl, heteroalkyl-cycloalkyl, heteroalkylheterocycloalkyl and heteroalkylheterocycloalkenyl, wherein the cyclic group is saturated or partially (e.g., two-fold or threefold) unsaturated.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocycloalkyl" refers to the above definition of cycloalkyl, wherein one or more, preferentially one, two or three ring carbon atoms are replaced by a O, N, Si, Se, P, or S, preferentially O, S, N. Preferentially a heterocycloalkyl group is composed of one or two rings comprising three to ten, preferentially three, four, five, six or seven ring atoms. Moreover, the term heterocycloalkyl refers to groups where one or more hydrogen atoms are replaced by F, Cl, Br, I, OH, =O, SH, =S, $NH_2$, $NO_2$. Examples of heterocycloalkyl are piperidyl, morpholinyl, urotropinyl, pyrrolidinyl, tetrahydrothiophenyl, tetrahydropyranyl, tetrahydrofuryl, oxacyclopropyl, azacyclopropyl or 2-pyrazolinyl groups as well as lactams, lactones, cyclic imides and cyclic anhydrides.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, imidazolidinone, piperidine, piperazine, pyrrolidine, morpholine, lactones, lactams, and the like.

The term "hydrocarbyl", as used herein, refers to a group that is bonded through a carbon atom that optionally has a =O or =S substituent and typically has at least one carbon-hydrogen bond and a primarily carbon backbone, but may optionally include functional groups with heteroatoms interrupting the carbon backbone. Examples of such functional groups with interrupting heteroatoms include amino, amide, carbonate, carbamate, ether (e.g., polyethylene glycol), ester, thioester, thiourea, and urea groups. For illustrative purposes, additional examples of hydrocarbyl groups include methyl, ethoxyethyl, 2-pyridyl, trifluoromethyl, and acetyl, but not, for example, ethoxy (which is linked through oxygen, not carbon). Additional hydrocarbyl groups include, but are not limited to aryl, heteroaryl, carbocycle, heterocycle, alkyl, alkenyl, alkynyl, and combinations thereof. Hydrocarbyl also includes corresponding divalent species (i.e., hydrocarbylene), such as alkylene, arylene, etc.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle may be substituted or unsubstituted. In certain embodiments, each ring of the polycycle contains from 3 to 10 atoms in the ring, preferably from 5 to 7.

The term "sulfate" is art-recognized and refers to the group —$OSO_3H$, or a pharmaceutically acceptable salt thereof.

The term "sulfonamide" is art-recognized and refers to the group represented by the general formulae

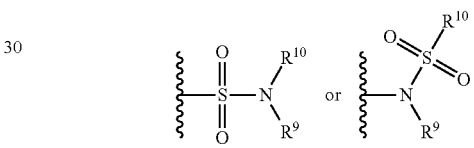

wherein $R^9$ and $R^{10}$ independently represents hydrogen or hydrocarbyl.

The term "sulfoxide" is art-recognized and refers to the group —S(O)—.

The term "sulfonate" is art-recognized and refers to the group $SO_3H$, or a pharmaceutically acceptable salt thereof.

The term "sulfone" is art-recognized and refers to the group —$S(O)_2$—.

The term "thioester", as used herein, refers to a group —C(O)$SR^9$ or —SC(O)$R^9$ wherein $R^9$ represents a hydrocarbyl.

The term "urea" is art-recognized and may be represented by the general formula

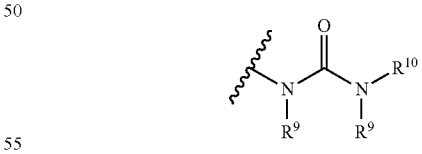

wherein $R^9$ and $R^{10}$ independently represent hydrogen or a hydrocarbyl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

IV. Pharmaceutical Compositions, Formulations and Dosages

In part, a biocompatible polymer composition of the present invention includes a biocompatible and optionally biodegradable polymer, such as one having the recurring monomeric units shown in one of the foregoing formulas, optionally including any other biocompatible and optionally biodegradable polymer mentioned above or known in the art. In certain embodiments, the compositions are non-pyrogenic, e.g., do not trigger elevation of a patient's body temperature by more than a clinically acceptable amount.

The subject compositions may contain a "drug," "therapeutic agent," "medicament," or "bioactive substance," which are biologically, physiologically, or pharmacologically active substances that act locally or systemically in the human or animal body. For example, a subject composition may include any of the other compounds discussed above.

Various forms of the medicaments or biologically active materials may be used which are capable of being released from the polymer matrix into adjacent tissues or fluids. They may be hydrophobic molecules, neutral molecules, polar molecules, or molecular complexes capable of hydrogen bonding. They may be in the form of ethers, esters, amides and the like, including prodrugs which are biologically activated when injected into the human or animal body, e.g., by cleavage of an ester or amide. A therapeutic agent in a subject composition may vary widely with the purpose for the composition.

Plasticizers and stabilizing agents known in the art may be incorporated in polymers of the present invention. In certain embodiments, additives such as plasticizers and stabilizing agents are selected for their biocompatibility. In certain embodiments, the additives are lung surfactants, such as 1,2-dipalmitoylphosphatidycholine (DPPC) and L-α-phosphatidylcholine (PC).

A composition of this invention may further contain one or more adjuvant substances, such as fillers, thickening agents or the like. In other embodiments, materials that serve as adjuvants may be associated with the polymer matrix. Such additional materials may affect the characteristics of the polymer matrix that results.

For example, fillers, such as bovine serum albumin (BSA) or mouse serum albumin (MSA), may be associated with the polymer matrix. In certain embodiments, the amount of filler may range from about 0.1 to about 50% or more by weight of the polymer matrix, or about 2.5, 5, 10, 25, or 40 percent. Incorporation of such fillers may affect the biodegradation of the polymeric material and/or the sustained release rate of any encapsulated substance. Other fillers known to those of skill in the art, such as carbohydrates, sugars, starches, saccharides, celluloses and polysaccharides, including mannitose and sucrose, may be used in certain embodiments of the present invention.

In other embodiments, spheronization enhancers facilitate the production of subject polymeric matrices that are generally spherical in shape. Substances such as zein, microcrystalline cellulose or microcrystalline cellulose co-processed with sodium carboxymethyl cellulose may confer plasticity to the subject compositions as well as implant strength and integrity. In particular embodiments, during spheronization, extrudates that are rigid, but not plastic, result in the formation of dumbbell shaped implants and/or a high proportion of fines, and extrudates that are plastic, but not rigid, tend to agglomerate and form excessively large implants. In such embodiments, a balance between rigidity and plasticity is desirable. The percent of spheronization enhancer in a formulation typically range from 10 to 90% (w/w).

In certain embodiments, a subject composition includes an excipient. A particular excipient may be selected based on its melting point, solubility in a selected solvent (e.g., a solvent that dissolves the polymer and/or the therapeutic agent), and the resulting characteristics of the microparticles or nanoparticles.

Excipients may comprise a few percent, about 5%, 10%, 15%, 20%, 25%, 30%, 40%, 50%, or higher percentage of the subject compositions.

Buffers, acids and bases may be incorporated in the subject compositions to adjust their pH. Agents to increase the diffusion distance of agents released from the polymer matrix may also be included.

Disintegrants are substances that, in the presence of liquid, promote the disruption of the subject compositions. Disintegrants are most often used in implants, in which the function of the disintegrant is to counteract or neutralize the effect of any binding materials used in the subject formulation. In general, the mechanism of disintegration involves moisture absorption and swelling by an insoluble material.

Examples of disintegrants include croscarmellose sodium and crospovidone which, in certain embodiments, may be incorporated into the polymeric matrices in the range of about 1-20% of total matrix weight. In other cases, soluble fillers such as sugars (mannitol and lactose) may also be added to facilitate disintegration of implants.

Other materials may be used to advantage or to control the desired release rate of a therapeutic agent for a particular treatment protocol. For example, if the sustained release is too slow for a particular application, a pore-forming agent may be added to generate additional pores in the matrix. Any biocompatible water-soluble material may be used as the pore-forming agent. They may be capable of dissolving, diffusing or dispersing out of the formed polymer system whereupon pores and microporous channels are generated in the system. The amount of pore-forming agent (and size of dispersed particles of such pore-forming agent, if appropriate) within the composition should affect the size and number of the pores in the polymer system.

Pore-forming agents include any pharmaceutically acceptable organic or inorganic substance that is substantially miscible in water and body fluids and will dissipate from the forming and formed matrix into aqueous medium or body fluids or water-immiscible substances that rapidly degrade to water-soluble substances.

Suitable pore-forming agents include, for example, sugars such as sucrose and dextrose, salts such as sodium chloride and sodium carbonate, and polymers such as hydroxylpropylcellulose, carboxymethylcellulose, polyethylene glycol, and PVP. The size and extent of the pores may be varied over a wide range by changing the molecular weight and percentage of pore-forming agent incorporated into the polymer system.

The charge, lipophilicity or hydrophilicity of any subject polymeric matrix may be modified by attaching in some fashion an appropriate compound to the surface of the matrix. For example, surfactants may be used to enhance wettability of poorly soluble or hydrophobic compositions. Examples of suitable surfactants include dextran, polysorbates and sodium lauryl sulfate. In general, surfactants are used in low concentrations, generally less than about 5%.

Binders are adhesive materials that may be incorporated in polymeric formulations to bind and maintain matrix integrity. Binders may be added as dry powder or as solution. Sugars and natural and synthetic polymers may act as binders.

Materials added specifically as binders are generally included in the range of about 0.5%-15% w/w of the matrix formulation. Certain materials, such as microcrystalline cellulose, also used as a spheronization enhancer, also have additional binding properties.

Various coatings may be applied to modify the properties of the matrices.

Three exemplary types of coatings are seal, gloss and enteric coatings. Other types of coatings having various dissolution or erosion properties may be used to further modify subject matrices behavior, and such coatings are readily known to one of ordinary skill in the art.

The seal coat may prevent excess moisture uptake by the matrices during the application of aqueous based enteric coatings. The gloss coat generally improves the handling of the finished matrices. Water-soluble materials such as hydroxypropylcellulose may be used to seal coat and gloss coat implants. The seal coat and gloss coat are generally sprayed onto the matrices until an increase in weight between about 0.5% and about 5%, often about 1% for a seal coat and about 3% for a gloss coat, has been obtained.

Enteric coatings consist of polymers which are insoluble in the low pH (less than 3.0) of the stomach, but are soluble in the elevated pH (greater than 4.0) of the small intestine. Polymers such as EUDRAGIT™, RohmTech, Inc., Malden, Mass., and AQUATERIC™, FMC Corp., Philadelphia, Pa., may be used and are layered as thin membranes onto the implants from aqueous solution or suspension or by a spray drying method. The enteric coat is generally sprayed to a weight increase of about 1% to about 30%, preferably about 10 to about 15% and may contain coating adjuvants such as plasticizers, surfactants, separating agents that reduce the tackiness of the implants during coating, and coating permeability adjusters.

The present compositions may additionally contain one or more optional additives such as fibrous reinforcement, colorants, perfumes, rubber modifiers, modifying agents, etc. In practice, each of these optional additives should be compatible with the resulting polymer and its intended use. Examples of suitable fibrous reinforcement include PGA microfibrils, collagen microfibrils, cellulosic microfibrils, and olefinic microfibrils. The amount of each of these optional additives employed in the composition is an amount necessary to achieve the desired effect.

The therapeutic polymer conjugates as described herein can be administered in various pharmaceutical formulations, depending on the disorder to be treated and the age, condition and body weight of the patient, as is well known in the art. For example, where the compounds are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eyedrops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent or a coating agent. Although the dosage will vary depending on the symptoms, age and body weight of the patient, the nature and severity of the disorder to be treated or prevented, the route of administration and the form of the drug, in general, a daily dosage of from 0.01 to 2000 mg of the therapeutic agent is recommended for an adult human patient, and this may be administered in a single dose or in divided doses.

The precise time of administration and/or amount of therapeutic polymer conjugate that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those therapeutic polymer conjugates, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" refers to the relatively non-toxic, inorganic and organic acid addition salts of the therapeutic polymer conjugates. These salts can be prepared in situ during the final isolation and purification of the therapeutic polymer conjugates, or by separately reacting a purified polymer in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", *J. Pharm. Sci.* 66:1-19)

In other cases, the therapeutic polymer conjugates useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of the polymer(s). These salts can likewise be prepared in situ during the final isolation and purification of the polymer(s), or by separately reacting the purified polymer(s) in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including ophthalmic, otic, buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a therapeutic polymer conjugate(s) with the carrier and, optionally, one or more accessory ingredients. In general, the formulations are prepared by uniformly and intimately bringing into association a therapeutic polymer conjugate with liquid carriers, or finely divided solid carriers, or both, and then, if necessary, shaping the product.

Formulations suitable for oral administration may be in the form of capsules, cachets, pills, tablets, gums, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a therapeutic polymer conjugate(s) as an active ingredient. A compound may also be administered as a bolus, electuary or paste.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active therapeutic polymer conjugates may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more therapeutic polymer conjugates with one or more suitable nonirritating excipients or carriers comprising for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of a therapeutic polymer conjugate(s) include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to ligand(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a therapeutic polymer conjugate(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The therapeutic polymer conjugate(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a therapeutic polymer conjugate(s) to the body. Such dosage forms can be made by dissolving or dispersing the agent in the proper medium. Absorption enhancers can also be used to increase the flux of the ligand across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more therapeutic polymer conjugate(s) in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of therapeutic polymer conjugate(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the therapeutic polymer conjugate(s) of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of agents may be given orally, parenterally, topically, or rectally. They are of course given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a therapeutic polymer conjugate, drug or other material other than directly into the central nervous system, such that it enters the patient's system and, thus, is subject to metabolism and other like processes, for example, subcutaneous administration.

The present therapeutic polymer conjugate(s) may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the therapeutic polymer conjugate(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

V. Physical Structures of the Subject Compositions

The subject polymers may be formed in a variety of shapes. For example, in certain embodiments, subject polymer matrices may be presented in the form of microparticles or nanoparticles. Microspheres typically comprise a biodegradable polymer matrix incorporating a drug. Microspheres can be formed by a wide variety of techniques known to those of skill in the art. Examples of microsphere forming techniques include, but are not limited to, (a) phase separation by emulsification and subsequent organic solvent evaporation (including complex emulsion methods such as oil in water emulsions, water in oil emulsions and water-oil-water emulsions); (b) coacervation-phase separation; (c) melt dispersion; (d) interfacial deposition; (e) in situ polymerization; (f) spray drying and spray congealing; (g) air suspension coating; and (h) pan and spray coating. These methods, as well as properties and characteristics of microspheres are disclosed in, for example, U.S. Pat. No. 4,438,253; U.S. Pat. No. 4,652,441; U.S. Pat. No. 5,100,669; U.S. Pat. No. 5,330,768; U.S. Pat. No. 4,526,938; U.S. Pat. No. 5,889,110; U.S. Pat. No. 6,034,175; and European Patent 0258780, the entire disclosures of which are incorporated by reference herein in their entireties.

To prepare microspheres of the present invention, several methods can be employed depending upon the desired application of the delivery vehicles. Suitable methods include, but are not limited to, spray drying, freeze drying, air drying, vacuum drying, fluidized-bed drying, milling, co-precipitation and critical fluid extraction. In the case of spray drying, freeze drying, air drying, vacuum drying, fluidized-bed drying and critical fluid extraction; the components (stabilizing polyol, bioactive material, buffers, etc.) are first dissolved or suspended in aqueous conditions. In the case of milling, the components are mixed in the dried form and milled by any method known in the art. In the case of co-precipitation, the components are mixed in organic conditions and processed as described below. Spray drying can be used to load the stabilizing polyol with the bioactive material. The components are mixed under aqueous conditions and dried using precision nozzles to produce extremely uniform droplets in a drying chamber. Suitable spray drying machines include, but are not limited to, Buchi, NIRO, APV and Lab-plant spray driers used according to the manufacturer's instructions.

The shape of microparticles and nanoparticles may be determined by scanning electron microscopy. Spherically shaped nanoparticles are used in certain embodiments, for circulation through the bloodstream. If desired, the particles may be fabricated using known techniques into other shapes that are more useful for a specific application.

In addition to intracellular delivery of a therapeutic agent, it also possible that particles of the subject compositions, such as microparticles or nanoparticles, may undergo endocytosis, thereby obtaining access to the cell. The frequency of such an endocytosis process will likely depend on the size of any particle.

In certain embodiments, solid articles useful in defining shape and providing rigidity and structural strength to the polymeric matrices may be used. For example, a polymer may be formed on a mesh or other weave for implantation. A polymer may also be fabricated as a stent or as a shunt, adapted for holding open areas within body tissues or for draining fluid from one body cavity or body lumen into another. Further, a polymer may be fabricated as a drain or a tube suitable for removing fluid from a post-operative site, and in some embodiments adaptable for use with closed section drainage systems such as Jackson-Pratt drains and the like as are familiar in the art.

The mechanical properties of the polymer may be important for the processability of making molded or pressed articles for implantation. For example, the glass transition temperature may vary widely but must be sufficiently lower than the temperature of decomposition to accommodate conventional fabrication techniques, such, as compression molding, extrusion, or injection molding.

VI. Biodegradability and Release Characteristics

In certain embodiments, the polymers and blends of the present invention, upon contact with body fluids, undergo gradual degradation. The life of a biodegradable polymer in vivo depends upon, among other things, its molecular weight, crystallinity, biostability, and the degree of crosslinking. In general, the greater the molecular weight, the higher the degree of crystallinity, and the greater the biostability, the slower biodegradation will be.

If a subject composition is formulated with a therapeutic agent or other material, release of such an agent or other material for a sustained or extended period as compared to the release from an isotonic saline solution generally results. Such release profile may result in prolonged delivery (over, about 1 to about 2,000 hours, or alternatively about 2 to about 800 hours) of effective amounts (e.g., about 0.0001 mg/kg/hour to about 10 mg/kg/hour) of the agent or any other material associated with the polymer.

A variety of factors may affect the desired rate of hydrolysis of polymers of the subject invention, the desired softness and flexibility of the resulting solid matrix, rate and extent of bioactive material release. Some of such factors include the selection/identity of the various subunits, the enantiomeric or diastereomeric purity of the monomeric subunits, homogeneity of subunits found in the polymer, and the length of the polymer. For instance, the present invention contemplates heteropolymers with varying linkages, and/or the inclusion of other monomeric elements in the polymer, in order to control, for example, the rate of biodegradation of the matrix.

To illustrate further, a wide range of degradation rates may be obtained by adjusting the hydrophobicities of the backbones or side chains of the polymers while still maintaining sufficient biodegradability for the use intended for any such polymer. Such a result may be achieved by varying the various functional groups of the polymer. For example, the combination of a hydrophobic backbone and a hydrophilic linkage produces heterogeneous degradation because cleavage is encouraged whereas water penetration is resisted.

One protocol generally accepted in the field that may be used to determine the release rate of any therapeutic agent or other material loaded in the polymer matrices of the present invention involves degradation of any such matrix in a 0.1 M PBS solution (pH 7.4) at 37° C., an assay known in the art. For purposes of the present invention, the term "PBS protocol" is used herein to refer to such protocol.

In certain instances, the release rates of different polymer systems of the present invention may be compared by subjecting them to such a protocol. In certain instances, it may be necessary to process polymeric systems in the same fashion to allow direct and relatively accurate comparisons of different systems to be made. For example, the present invention teaches several different means of formulating the polymeric, matrices of the present invention. Such comparisons may indicate that any one polymeric system releases incorporated material at a rate from about 2 or less to about 1000 or more times faster than another polymeric system.

Alternatively, a comparison may reveal a rate difference of about 3, 5, 7, 10, 25, 50, 100, 250, 500 or 750 times. Even higher rate differences are contemplated by the present invention and release rate protocols.

In certain embodiments, when formulated in a certain manner, the release rate for polymer systems of the present invention may present as mono- or bi-phasic.

Release of any material incorporated into the polymer matrix, which is often provided as a microsphere, may be characterized in certain instances by an initial increased release rate, which may release from about 5 to about 50% or more of any incorporated material, or alternatively about 10, about 15, about 20, about 25, about 30 or about 40%, followed by a release rate of lesser magnitude.

The release rate of any incorporated material may also be characterized by the amount of such material released per day per mg of polymer matrix. For example, in certain embodiments, the release rate may vary from about 1 ng or less of any incorporated material per day per mg of polymeric system to about 500 or more ng/day/mg. Alternatively, the release rate may be about 0.05, 0.5, 5, 10, 25, 50, 75, 100, 125, 150, 175, 200, 250, 300, 350, 400, 450, or 500 ng/day/mg. In still other embodiments, the release rate of any incorporated material may be about 10,000 ng/day/mg, or greater. In certain instances, materials incorporated and characterized by such release rate protocols may include therapeutic agents, fillers, and other substances.

In another aspect, the rate of release of any material from any polymer matrix of the present invention may be presented as the half-life of such material in the matrix.

In addition to the embodiment involving protocols for in vitro determination of release rates, in vivo protocols, whereby in certain instances release rates for polymeric systems may be determined in vivo, are also contemplated by the present invention. Other assays useful for determining the release of any material from the polymers of the present system are known in the art.

VII. Implants and Delivery Systems

In its simplest form, a biodegradable delivery system for a therapeutic agent consists of a dispersion of such a therapeutic agent in a polymer matrix. In other embodiments, an article is used for implantation, injection, or otherwise placed totally or partially within the body, the article comprising the subject compositions. It is particularly important that such an article result in minimal tissue irritation when implanted or injected into vasculated tissue.

Biodegradable delivery systems, and articles thereof, may be prepared in a variety of ways known in the art. The subject polymer may be melt-processed using conventional extrusion or injection molding techniques, or these products may be prepared by dissolving in an appropriate solvent, followed by formation of the device, and subsequent removal of the solvent by evaporation or extraction.

Once a system or implant article is in place, it should remain in at least partial contact with a biological fluid, such as blood, internal organ secretions, mucus membranes, cerebrospinal fluid, and the like to allow for sustained release of any encapsulated therapeutic agent.

VIII. Methods and Uses

In certain situations, the present polymer conjugates can be used in the treatment of one or more diseases, such as those exhibiting abnormal cellular proliferation, such as cancer, for example, breast, lung, colon, and ovarian cancer. When employed in the treatment of cancers, the subject polymer conjugates in some cases comprise one or more therapeutic agents including, but not limited to, salicylic acid, acetaminophen, morphine, etoposide, a tubulysin (preferably tubulysin A, tubulysin B, or tubulysin C), an epothilone, camptothecin, or vancomycin, or an analog or derivative thereof, particularly a tubulysin, an epothilone or an analog or derivative thereof.

REFERENCES

Additional cyclodextrin-containing polymers that can be modified according to the teachings of the present invention, as well as methods of preparing such polymers, are disclosed in U.S. Pat. Nos. 6,509,323; 7,018,609; 7,091,192; and, 7,166,302 and U.S. patent application Ser. No. 09/453,707, all of which are hereby incorporated herein by reference in their entireties.

All of the references, patents, and publications cited herein are hereby incorporated by reference in their entireties.

EXEMPLIFICATION

Example 1

Synthesis of CDP-PEG-GFLG-MEDA-ETOP

Synthesis of FMOC-PEG-GFLG-MEDA

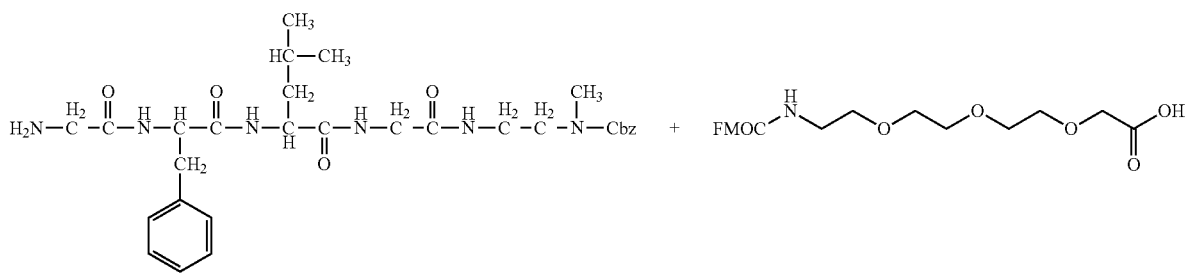

-continued

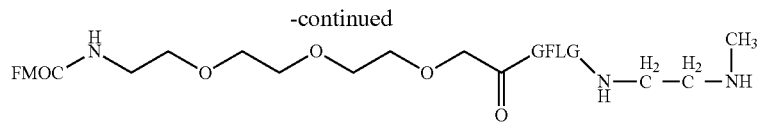

Fmoc-PEG-aceticacid (5.7 g, 13 mmol), HBTU (4.9 g, 13 mmol), HOBT (2.0 g, 13 mmol), and DIPEA (3.4 g, 26 mmol) were dissolved in DMF (25 mL). GFLG-MEDA-Z (5.1 g, 8.8 mmol) was dissolved in DMF (13 mL) and DIPEA (3.7 g, 29 mmol) and added to the previous solution prepared. The reaction mixture was stirred for 1.5 h at room temperature. DMF was removed under reduced pressure and the obtained residue was dissolved in 200 mL $CH_2Cl_2$, the solution was washed twice with 0.1 N HCl (200 mL) and followed by washing with water (200 mL). It was then dried over $MgSO_4$ and $CH_2Cl_2$ was removed under vacuum to yield crude product. It was then purified by flash column chromatography to yield white solid product, FMOC-PEG-GFLG-MEDA-Z (6.2 g, 72%).

FMOC-PEG-GFLG-MEDA-Z (3.0 g, 3.0 mmol) was dissolved in $CH_2Cl_2$ (60 mL) of 0.2 M 2-Bromo-1,3,2-benzodioxaborole (2.4 g, 12 mmol). The reaction mixture was stirred overnight at room temperature. The reaction was stopped by the addition of MeOH (10 mL). Solvents were removed under vacuum. The obtained residue was dissolved in a small volume of methanol and precipitated in cool diethyl ether to yield the product (2.6 g, >99%). ESI/MS (m/z) expected 860.01; found 882.76 [M+Na].

Synthesis of PEG-GFLG-MEDA-ETOP

FMOC-PEG-GFLG-MEDA (2.6 g, 2.8 mmol), Etop-NP (2.7 g, 3.6 mmol), DIPEA (0.70 g, 5.5 mmol) and DMAP (34 mg, 0.28 mmol) were dissolved in DMF (60 mL) and stirred for 1.5 h at 60° C. DMF was removed under vacuum. The obtained residue was dissolved in $CH_2Cl_2$ (150 mL). It was then washed twice with 0.1 N HCl (150 mL) and followed by washing with water (150 mL). It was dried over $MgSO_4$ and reduced under vacuum to yield the crude product. The crude product was purified by flash column chromatography to yield the product, FMOC-PEG-GFLG-MEDA-ETOP (3.2 g, 80%). ESI/MS (m/z) expected 1474.6; found 1497.16 [M+Na].

FMOC-PEG-GFLG-MEDA-ETOP (100 mg, 0.068 mmol) was dissolved in 1.2 mL of 20% piperidine in DMF. The reaction mixture was stirred for 3 min at room temperature. The product was precipitated in diethyl ether (50 mL) and washed with to yield the product (60 mg, 70%). ESI/MS (m/z) expected 1252.32; found 1274.87 [M+Na].

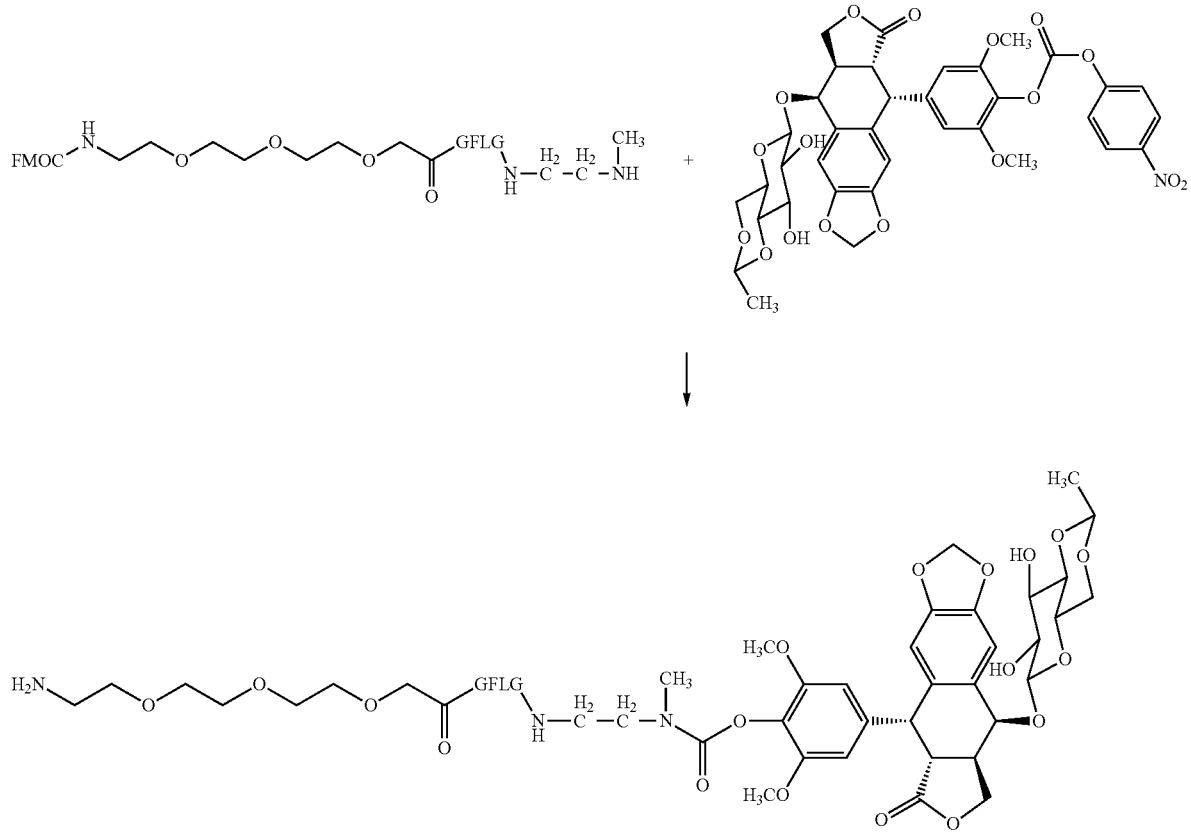

Synthesis of CDP-PEG-GFLG-MEDA-ETOP

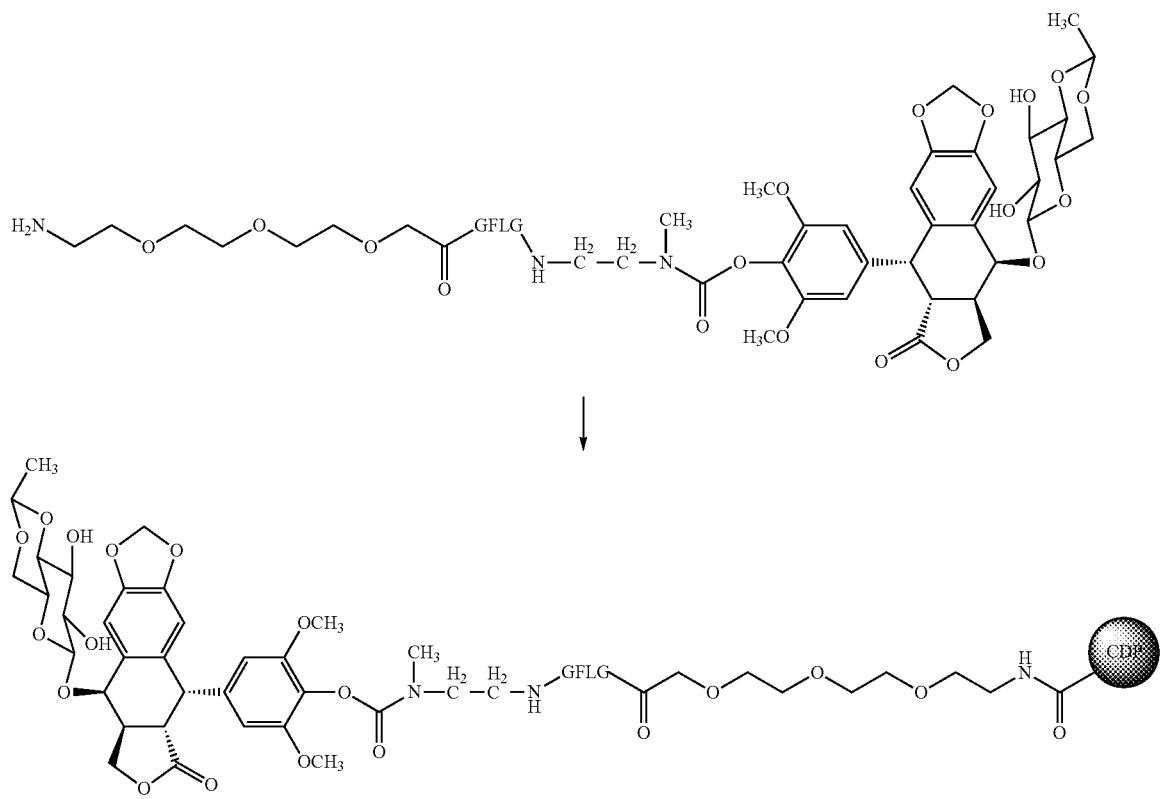

Cyclodextrin-based polymer (CDP) (1.8 g, 0.36 mmol) was dissolved in dry DMF (35 mL). The mixture was stirred until completely dissolved. DIPEA (0.94 g, 7.3 mmol), EDC (0.70 g, 3.6 mmol), and NHS (420 mg, 3.6 mmol) were added into the above solution. PEG-GFLG-MEDA-ETOP (1.4 g, 1.1 mmol) was dissolved in DMF (10 mL) and added to the polymer solution. The solution was stirred for 4 h, and then the polymer was precipitated in ethylacetate (150 mL). The precipitate was dissolved in DMF (15 mL) and precipitated in acetone (75 mL). The precipitated product was dissolved in pH 4 water (80 mL). The solution was dialyzed using 25K MWCO membrane (Spectra/Por 7) for 24 h. It was filtered through 0.2 μm filters (Nalgene) and lyophilized to yield white solid (1.1 g, 61%). Loading of etoposide was determined to be 10% w/w by UV-Vis Spectroscopy at 283 nm.

Example 2

Synthesis of CDP-Carbamate-S—S-Etoposide

Synthesis of 4-nitrophenyl carbonate ester of etoposide

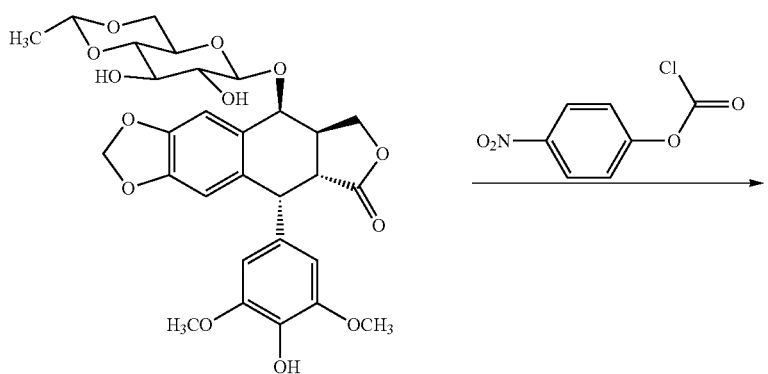

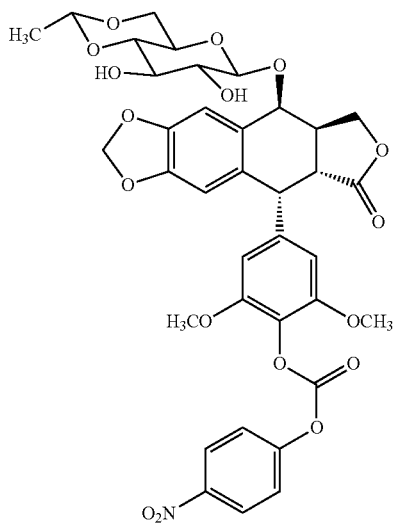

In a dry 100 mL round bottom flask, etoposide (1.0 g, 1.7 mmol) and TEA (2.5 g, 25 mmol) were dissolved in anhydrous THF (35 mL) under argon. To that solution, 4-nitrophenyl chloroformate (0.39 g, 1.95 mmol) in anhydrous THF (15 mL) was added dropwise over 30 min. The reaction mixture was stirred for additional 2 h at RT. The mixture was filtered and concentrated under reduced pressure to yield yellow solid. The solid was purified by flash column chromatography to yield light yellow solid (0.75 g, 59%).

Synthesis of 4-pyridylthiol cysteamine carbamate of etoposide

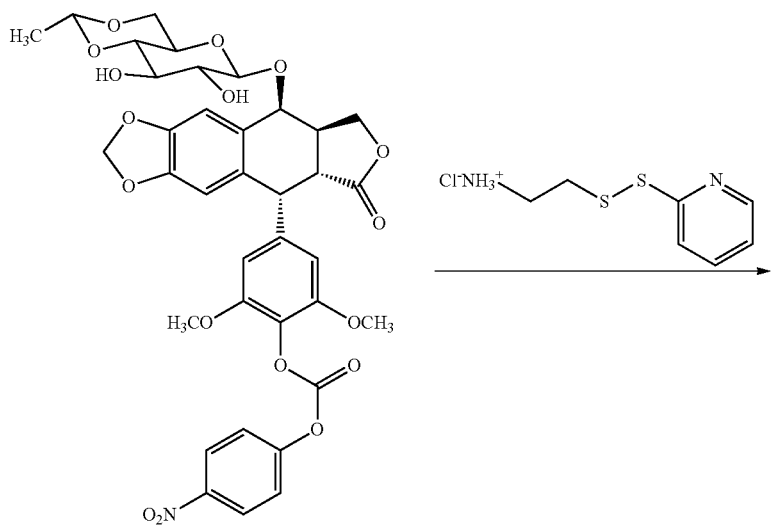

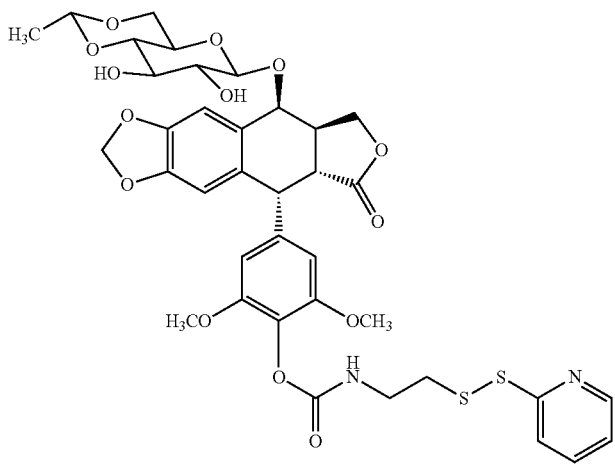

In a dry 25 mL round bottom flask, 4-nitrophenyl carbonate ester of etoposide (100 mg, 0.13 mmol), 4-pyridylthiol cysteamine hydrochloride (35 mg, 0.16 mmol), DIPEA (34 mg, 0.27 mmol) were dissolved in DMF (5 mL). The reaction mixture was stirred at room temperature for 15 h. DMF was removed under reduced pressure to yield a light yellow solid. $CH_2Cl_2$ (25 mL) was added and it was washed with 0.1 N HCl (10 mL) twice. It was then dried over $MgSO_4$ and concentrated to yield a light yellow solid. The solid was purified by flash column chromatography to yield yellow solid (51 mg, 48%).

Synthesis of cystamine carbamate of etoposide

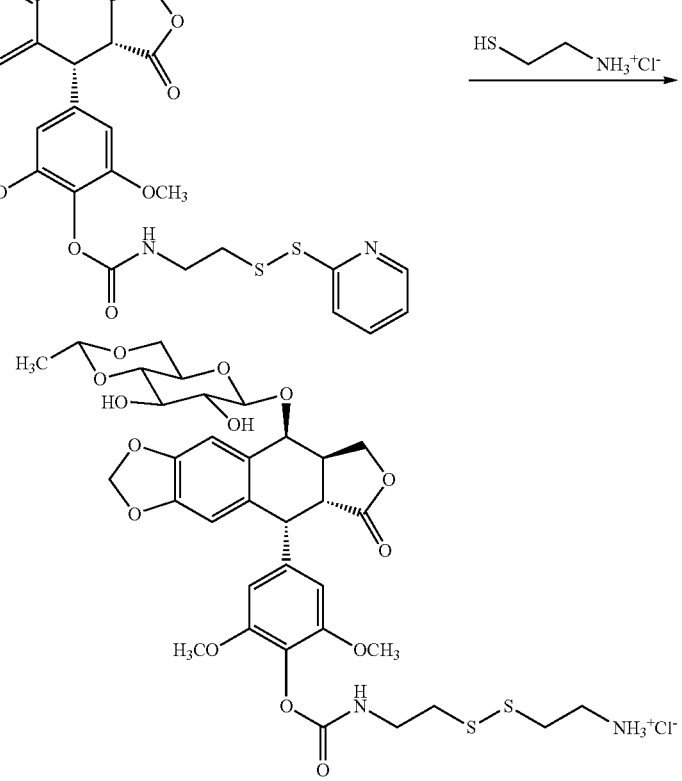

In a 10 mL round bottom flask, 4-pyridylthiol cysteamine carbamate of etoposide (50 mg, 0.0625 mmol) and cysteamine hydrochloride (6.4 mg, 0.057 mmol) were dissolved in MeOH (2 mL). The mixture was stirred for 1 h at room temperature. The solution was concentrated under vacuum and diethyl ether (5 mL) was added to precipitate out white solid. The solid was filtered and redissolved in MeOH (0.5 mL) and precipitated in CH$_2$Cl$_2$ (15 mL). The solid was filtered and dried under vacuum to yield a white solid. It was then purified by Prep HPLC to yield white solid (19 mg, 38%). ESI/MS (m/z) expected 767.84; found 767.29 [M]$^+$.

Synthesis of CDP-Carbamate-S—S-Etoposide

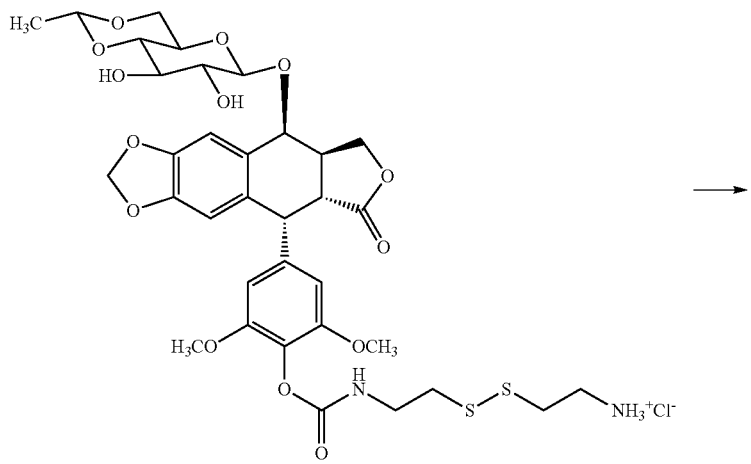

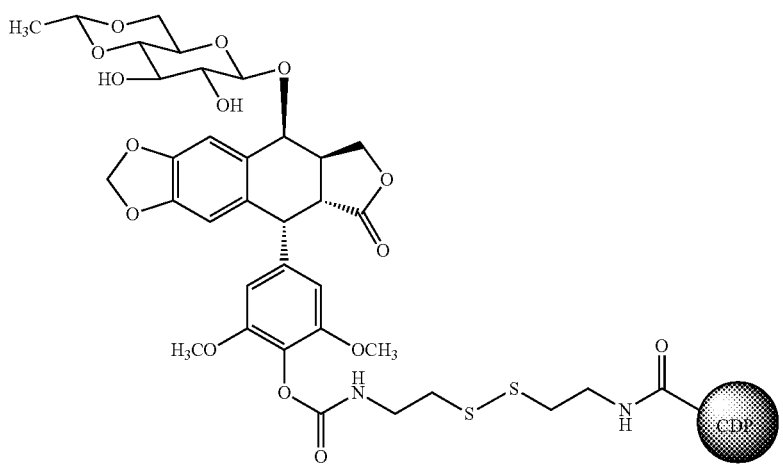

CDP (96 mg, 0.020 mmol) was dissolved in dry N,N-dimethylformamide (2 mL). The mixture was stirred for 20 min. Cystamine carbamate of etoposide (35 mg, 0.044 mmol), N,N-Diisopropylethylamine (5.6 mg, 0.044 mmol), N-(3-Dimethylaminopropyl)-N'-ethylcarbodiimide hydrochloride (11 mg, 0.059 mmol), and N-Hydroxysuccinimide (5.0 mg, 0.044 mmol) were added to the polymer solution and stirred for 4 h. The polymer was precipitated with ethylacetate (50 mL). The precipitate was dissolved in deionized water (10 mL). The solution was dialyzed using 25K MWCO membrane (Spectra/Por 7) for 27 h. It was filtered through 0.2 μm filters (Nalgene) and lyophilized to yield white solid (57 mg, 59%). Loading of etoposide was determined to be 12.5% w/w by UV-Vis Spectroscopy at 283 nm.

Example 3

Synthesis of CDP-EDA-Phosphoester-Etoposide

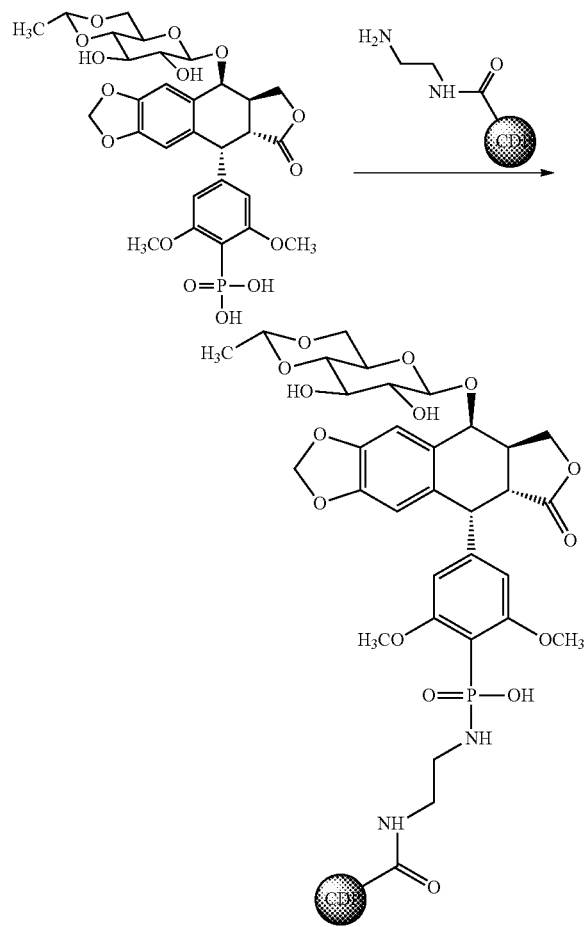

In a 100 mL round bottom flask, etopophosphate (720 mg, 1.1 mmol), N,N'-diisopropylcarbodiimide (96 mg, 0.72 mmol), N-hydroxysuccinimide (83 mg, 0.72 mmol) and N,N-Diisopropylethylamine (140 mg, 2.3 mmol) were dissolved in anhydrous DMF (10 mL). The solution was stirred for 45 min at room temperature. EDA functionalized CDP (1.5 g, 0.60 mmol) and N,N-Diisopropylethylamine (160 mg, 2.3 mmol) were dissolved in anhydrous DMF (10 mL) on a separate 100 mL round bottom flask. This reaction mixture was added to the previous mixture at room temperature and stirred for 4 h at room temperature. The mixture was concentrated to 10 mL and precipitated out in ethyl acetate (500 mL). The polymer was dissolved in deionized water (150 mL) and it was dialyzed using 25K MWCO membrane (Spectra/Por 7) for 26 h. It was then filtered through 0.2 μm filters (Nalgene) and lyophilized to yield white solid (1.1 g, 73%). Loading of etoposide was determined to be 8.3% w/w by UV-Vis Spectroscopy at 283 nm.

Example 4

CDP-PEG-SS-Tubulysin

Synthesis of CDP-PEG-SS-Py

A mixture of CDP-PEG (2 g, 0.43 mmole), which was synthesized according to a published procedure (Bioconjugate Chem. 2003, 14, 1007), pyridine dithioethylamine hydrochloric salt (384 mg, 1.73 mmole), EDC (333 mg, 1.73 mmole), and NHS (198 mg, 1.73 mmole) was dried overnight in a 200 mL round bottom flask under vacuum. Anhydrous DMF (40 mL) was then added, followed by DIEA (0.3 mL, 1.73 mmole). The reaction mixture was stirred under argon at room temperature for 4 h. Diethyl ether (300 mL) was then added into the mixture to precipitate the polymer. The crude product was dissolved in $H_2O$ (400 mL) and the solution was dialyzed using a 25K MWCO membrane (Spectra/Por 7) against water. The dialysis water was changed twice over a period of 24 h, after which the polymer containing solution was filtered through a 0.2 μm filter membrane and lyophilized to yield 1.64 g of CDP-PEG-SS-Py (82% yield) as a white solid.

Synthesis of CDP-PEG-SH

To a PBS (6.8 mL) solution of CDP-PEG-SS-Py (155 mg, 0.032 mmole) was added a water (1 mL) solution of DTT, which gave rise to 20 mg/mL of the concentration of polymer. The reaction mixture was stirred at room temperature for 3 h and then dialyzed by a 25K MWCO membrane in degassed EDTA (1 mM, 2 L) water solution. The dialysis water was changed once over a period of 24 h. After filtration with 0.2 μm filter membrane, the solution was lyophilized to produce a white solid (109 mg) in quantitative yield.

Synthesis of Tubulysin-SS-Py

To a solution of pyridine dithioethylamine hydrochloric salt (15.8 mg, 0.071 mmole) in anhydrous DMF (1.5 mL) was added DIEA (25 μL, 0.142 mmole) followed by a solution of tubulysin A (40 mg, 0.047 mmole) in anhydrous DMF (0.5 mL). The reaction mixture was stirred under argon at room temperature for 2 h. The mixture was then evaporated under vacuum. The crude product was purified by silica gel column chromatography ($CH_2Cl_2$/MeOH, 15/1) to afford white solid (54 mg) in quantitative yield.

Synthesis of CDP-PEG-SS-Tubulysin ("CDP-S—S-Tub")

CDP-PEG-SS-Py (43 mg, 0.0094 mmole) was dissolved in degassed MeOH (1.8 mL), into which was added a methanol solution (0.35 mL) of Tub-S—S-pyr (9.5 mg, 0.0094 mmole) to bring the total reaction volume of 2.15 mL. The resulting yellow mixture was stirred under argon at room temperature for 4 h. N-ethyl maleimide (118 mg, 0.94 mmole) was then added to quench the reaction resulting in clear, colorless solution. This solution was dialyzed using a 25K MWCO membrane, and the dialysis water was changed once over a period of 24 h. The solution was then filtered through 0.2 μm filter membrane and lyophilized to afford target polymer (27 mg, 45% yield) as a white solid.

containing 10% fetal bovine serum (FBS). 10,000 cells per well were seeded in a 96-well plate and incubated at 37° C. for 24 hours, at which time drug was added to triplicate wells at various concentrations. After 72 hours of incubation at 37° C.

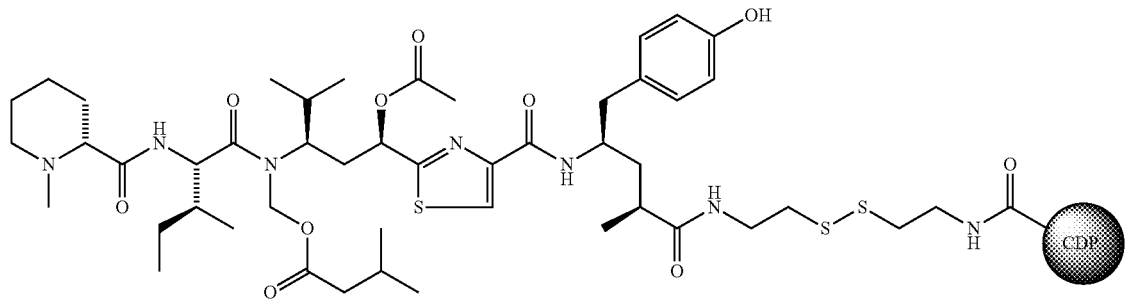

CDP-PEG-SS-Tubulysin (General Structure)

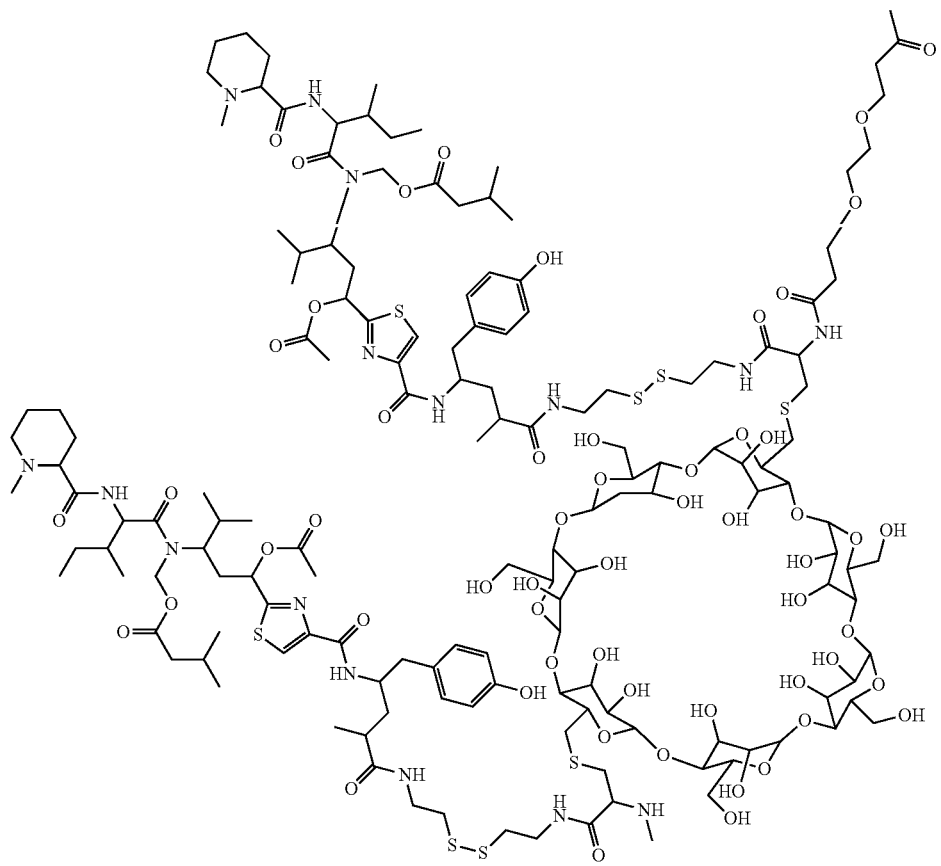 [SMILES: CCC(C)C(NC(=O)C1CCCCN1C)C(=O)N(COC(=O)CC(C)C)C(CC(OC(C)=O)c1nc(C(=O)NC(Cc2ccc(O)cc2)CC(C)C(=O)NCCSSCCNC(=O)C(CSCC2OC3OC4C(CO)OC(OC5C(CO)OC(OC6C(CO)OC(OC7C(CSCC(NC(=O)CCOCCOCCC(C)=O)C(=O)NCCSSCCNC(=O)C(C)CC(Cc8ccc(O)cc8)NC(=O)c8csc(C(CC(C(C)C)N(COC(=O)CC(C)C)C(=O)C(NC(=O)C9CCCCN9C)C(C)CC)OC(C)=O)n8)OC(OC8C(O)CC(OC8CO)OC8C(CO)OC(OC2C(O)C3O)C(O)C8O)C(O)C7O)C(O)C6O)C(O)C5O)C(O)C4O)NC)cs1)C(C)C]

CDP-PEG-SS-Tubulysin (Detailed Structure)

Example 5

In Vitro Studies of Etoposide Derivatives

The cytotoxicity of drug-polymer conjugates and linker-drug precursors was determined in the human ovarian carcinoma cell line A2780. Cells were grown in RPMI 1640 media in the presence of drug, cells were washed with PBS, incubated for 1 hour with an MTS solution, and analyzed according to manufacturer's instructions (CellTiter 96 one solution cell proliferation assay, Promega, Madison, Wis.). The concentration of drug to kill 50% of cells ($IC_{50}$) was determined using a 4-parameter fit (see Table 1).

TABLE 1

IC$_{50}$ values for etoposide derivatives

| Compound | Linker | Drug Loading | IC$_{50}$ (μM) |
|---|---|---|---|
| etoposide | — | — | 0.2 |
| CDP-GFLG-DMEDA-Etop | DMEDA-GFLG | 8.1% | 349.0 |
| CDP-GFLG-MEDA-Etop | MEDA-GFLG | 9.2% | 81.3 |
| CDP-PEG-GFLG-MEDA-Etop | MEDA-GFLG-PEG | 10.9% | 22.6 |
| CDP-carbonate-SS-Etop | disulfide bond | 17.0% | 12.3 |
| CDP-carbamate-SS-Etop | disulfide bond | 12.5% | 15.1 |
| CDP-EDA-EtopPhos | phosphate | 10.7% | 0.7 |
| CDP-EDA-EtopPhosphoester | phosphoester | 13.7% | 25.7 |

Example 6

In Vitro Studies of CDP-PEG-SS-Tubulysin

The antiproliferative activity of CDP-PEG-SS-Tubulysin (CDP-S—S-Tub) was evaluated in vitro in multiple human cancer cell lines (NCI-H1299 lung cancer, HT-29 colon cancer, and A2780 ovarian cancer) and compared with Tubylysin A (Tub A) and the sulfur derivatized Tubylysin A (Tub-SH) (Table 2). The data shows that the conjugate maintains high antiproliferative activity.

TABLE 2

IC50 values for CDP-PEG-SS-Tubulysin

| Cell lines | IC$_{50}$ (nM) | | |
|---|---|---|---|
| | CDP-S-S-Tub | Tub A | Tub-SH |
| NCI-H1299 (lung) cells | 23.7 | 2.8 | N/A |
| HT-29 (colon) cells | 4.9 | 1.3 | 4.4 |
| A2780 (ovarian) cells | 13 | 2.4 | N/A |

Example 7

Maximum Tolerated Dose (MTD) Studies of CDP-S—S-Tub

HRLN female nu/nu mice were set up and dosing solutions were prepared. Body weight was determined biweekly until the end of the study. The endpoint was where mean weight loss exceeded 20% or >10% of animals in a group died, dosing was immediately stopped. Moribund animals were euthanized following PRC SOP. All animals were euthanized 14 days post final dose.

The maximum tolerated dose of CDP-PEG-SS-Tubulysin (CDP-S—S-Tub) was determined in nude mice and found to be 6 mg/kg (in Tubulysin equivalents) whereas that of Tubulysin A was 0.05 mg/kg (Table 3).

TABLE 3

MTD studies of CDP-S-S-Tub[a]

| Group | n | Treatment agent | mg/kg | Mean BW Nadir[b] | # of TR[c] | Avg. Day of TR |
|---|---|---|---|---|---|---|
| 1 | 4 | CDP-S-S-Tub | 10 | (−) 23.4% Day 5 | 4 | 7 |
| 2 | 5 | CDP-S-S-Tub | 8 | (−) 22.1% Day 11 | 1 | 11 |
| 3 | 5 | CDP-S-S-Tub | 6 | (−) 10.8% Day 4 | 0 | N/A |
| 4 | 4 | CDP-S-S-Tub | 3 | (−) 8.7% Day 11 | 0 | N/A |
| 5 | 4 | CDP-S-S-Tub | 1 | (−) 0.4% Day 2 | 0 | N/A |
| 6 | 4 | Tubulysin A | 3 | (−) 9.7% Day 2 | 4 | 3 |
| 7 | 4 | Tubulysin A | 1 | (−) 15.7% Day 3 | 4 | 4 |
| 8 | 4 | Tubulysin A | 0.3 | (−) 18.9% Day 8 | 4 | 9 |
| 9 | 5 | Tubulysin A | 0.05 | (−) 0.3% Day 5 | 0 | N/A |

[a]all mice were treated with schedule qwkx3 using iv injection
[b]Nadir: the lowest point
[c]TR: treatment related deaths

Example 8

Efficacy Studies of CDP-S—S-Tub

General Procedure

Subcutaneous human tumor xenografts. The HT29 colon cancer cell line was maintained in nude mice. Then 1 mm$^3$ HT29 tumor fragments were implanted s.c. into the right flank of HRLN female nu/nu mice.

Tumors were measured in two dimensions with calipers bi-weekly to the end of the study. Tumor volume was calculated based on the formula: tumor volume=(length×width$^2$)/2. Tumor weight was obtained from tumor volume assuming 1 mm$^3$ is equal to 1 mg of tumor in weight. When tumors reach an average size of 80-120 mg, a pair match was done to sort mice into groups of ten each and then treatment was started (day 1).

All of the treatments were given by i.v. The endpoint of the experiment was a tumor volume of 1 gm or 90 days. When tumor reached the endpoint the mouse was euthanized and endpoint tumor growth delay was calculated consequently. End-point tumor size was chosen to maximize the number of tumor doublings within the exponential growth phase in the control animals. It was set at 1000 mm$^3$ for HT29.

Determination of treatment efficacy. Treatment efficacy was determined by the time which took a specific tumor to reach the predetermined endpoint size (1000 mm$^3$ for HT29). The time to endpoint (TTE) for each mouse was calculated from the equation TTE=[log(endpoint)−b]/m, where b was the intercept and m was the slope of the line obtained by linear regression of a log-transformed tumor growth data set, which consisted of the first observation that exceeded the study endpoint volume and the three consecutive observations that immediately preceded the attainment of the endpoint volume. TTE values equal to the last day of the study were assigned to those mice whose tumor volume did not reach the endpoint size. A TTE value equal to the day of death was assigned to a mouse whose death was classified as treatment-related death. The mice whose deaths were classed as non-treatment-related deaths were excluded from TTE calculations. Tumor growth delay (TGD) is defined as the difference between the median TTE for a treatment group and the median TTE of the control group (TGD=T−C). It is expressed in days and as a percentage of the median TTE of the control group: % TGD=[(T−C)/C]×100, where T equals the median TTE for a treatment group and C equals the median TTE for control.

Treatment may cause partial regression or complete regression of the tumor in an animal. Partial regression response is defined as the tumor volume's being ≦50% of its day 1 volume for three consecutive measurements during the course of the study and ≧13.5 mm$^3$ for one or more of these three measurements. Complete regression response is defined as the tumor volume is <13.5 mm$^3$ for three consecutive measurements during the course of the study. A tumor-free survivor is an animal with a complete regression response at the end of the study.

Determination of tolerability. Animals were weighed daily on days 1 to 5, then twice per week until the completion of the study. The mice were examined for overt signs of any adverse drug-related side effects. Acceptable toxicity for the maximum tolerated dose was defined as group mean weight loss less than 20% or no more than 10% of animals in a group die from toxicity.

Efficacy Studies

Efficacy was evaluated in nude mice bearing subcutaneously implanted HT-29 colorectal carcinoma xenografts.

blastine was administered as a solution in 100% Saline. The dosing volume was 10 mL/kg (0.200 mL/20 g mouse) adjusted for body weight.

Figure 2:
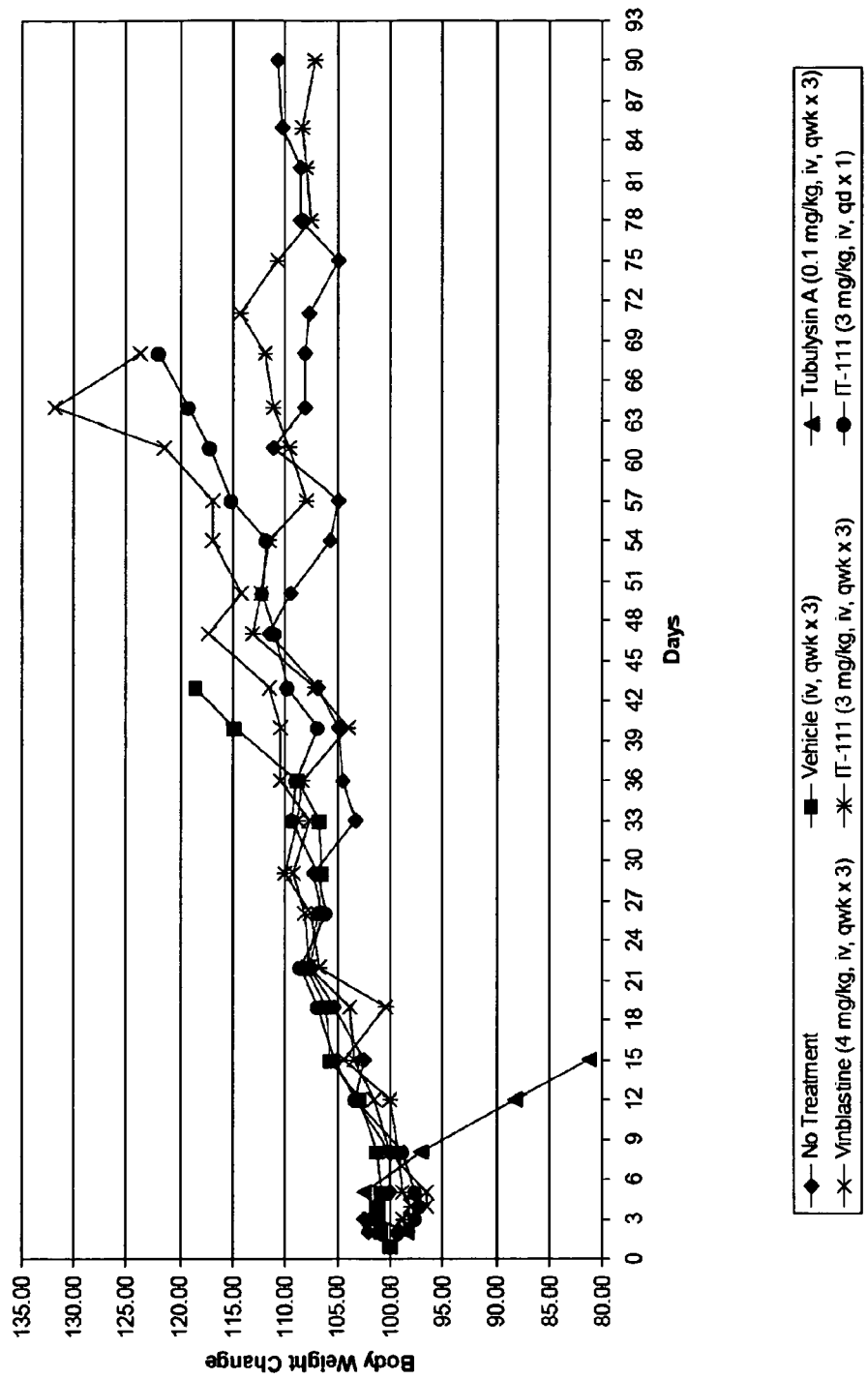
FIG. 2 shows the body weight mean summary data for HT29 colon carcinoma xenograft in mice treated with CDP-PEG-SS-Tubulysin.

Treatment with CDP-PEG-SS-Tubulysin (CDP-S—S-Tub) was well tolerated, with no mortality or significant antitumor effect. It was better tolerated than vinblastine and Tubulysin A. Treatment with CDP-PEG-SS-Tubulysin resulted in a higher number of regressions and a significant increase in tumor growth delay compared to Vinblastine. Treatment with Tubulysin A was proven to be toxic for the mice, causing 50% mortality and 26.8% maximum body weight loss on day 26 (Table 4 and FIGS. 1-2).

TABLE 4

Antitumor activity of CDP-S-S-Tub

| | Group | | | | |
|---|---|---|---|---|---|
| | 1[b] | 2 | 3 | 4 | 5 |
| | | | n | | |
| | 10 | 10 | 10 | 10 | 10 |
| Treatment Regimen[a] | | | | | |
| Agent | Vehicle[c] | Tubulysin A | Vinblastine | CDP-S-S-TUB | CDP-S-S-TUB |
| mg/kg | — | 0.1 | 4 | 3[d] | 3[d] |
| Schedule | qwkx3 | qwkx3 | qwkx3 | qwkx3 | qdx1 |
| Treatment Results | | | | | |
| MTV(n), Day 90[e] | — | — | — | 700.0 (3) | — |
| BW Nadir (%) | — | −26.80 | −3.60 | −2.20 | −2.90 |
| Median TTE | 33.65 | 34.46 | 45.05 | 73.55 | 56.92 |
| TC | — | 0.81 | 11.4 | 39.9 | 23.27 |
| % TGD | — | 2.42 | 33.89 | 118.57 | 69.15 |
| Statistical Significance[f] | | | | | |
| vs G1 | — | ne | ** | *** | *** |
| vs G4 | *** | ne | *** | — | *** |
| vs G5 | *** | ne | ns | *** | — |
| Regressions | | | | | |
| PR | 0 | 0 | 0 | 6 | 0 |
| CR | 0 | 0 | 0 | 3 | 0 |
| TFS | 0 | 0 | 0 | 1 | 0 |
| Deaths | | | | | |
| TR | 0 | 5 | 0 | 0 | 0 |

Endpoint: TV = 1000 mm³ or Day 90, whichever comes first
[a]all mice were treated using i.v. injection
[b]control group
[c]vehicle: 10% DMSO: 1% Tween 80: 89% Saline
[d]active Tub dose equivalents
[e]MTV(n): median tumor volume (mm3) for the number of animals on the day of TGD analysis (excludes animals with tumor volume at endpoint)
[f]ne = not evaluable; ns = non-significant;  = $0.001 < P < 0.01$; * = $P < 0.001$ HRLN female nu/nu mice were set up with 1 mm³ HT-29 tumor fragments s.c. in the flank. The pair match was then done when the tumors reached an average size of 80 to 120 mg and was followed by beginning treatment. Dosing solutions were prepared daily and body weight was determined bi-weekly until the end of the study. Caliper measurements were taken bi-weekly to the end of the study. Animals were monitored individually, and the endpoint of the experiment was a tumor volume of 1 g or 90 days, whichever came first. Responders were followed longer. When the endpoint was reached, the animals were euthanized.

CDP-PEG-SS-Tubulysin (CDP-S—S-Tub) was administered as a solution in 100% water. Tubulysin A was administered as a solution in 10% DMSO:1% Tween 80:89% Saline. The vehicle was 10% DMSO:1% Tween 80:89% Saline. Vin- A polymer-tubulysin conjugate CDP-PEG-SS-Tubulysin was synthesized and found to be highly soluble in water. The conjugate showed strong antiproliferative activity in multiple human cancer cell lines. The MTD of CDP-PEG-SS-Tubulysin was determined to be between 3 and 10 mg/kg while the free drug Tubulysin A was severely toxic even at 0.1 mg/kg. Efficacy studies of CDP-PEG-SS-Tubulysin at 3 mg/kg showed that it was well-tolerated and produced substantial antitumor activity during a 90-day study. By contrast, the free drug Tubulysin A showed excessive toxicity, causing 50% mortality. Vinblastine, a vinca alkaloid that inhibits tubulin polymerization by binding to the same binding site as Tubulysin A, was significantly less effective as an antitumor agent compared to CDP-PEG-SS-Tubulysin. These results demonstrate that conjugation to a cyclodextrin-based polymer can improve the solubility, tolerability, and preclinical antitumor activity of antitumor drugs such as Tubulysin A.

Example 9

Characterization and Release Studies of CDP-PEG-SS-Tubulysin

Loading was determined by HPLC to be 12%. The particle size of the parent polymer was measured to be 9-10 nm while CDP-PEG-SS-Tubulysin self-assembled into nanoparticles with a particle size of 127 nm. The solubility of Tubulysin A in water was determined to be 0.1 mg/mL at a neutral pH while that of CDP-PEG-SS-Tubulysin was found to be 100 times higher.

Release studies were performed by incubating CDP-PEG-SS-Tubulysin in both PBS and human plasma. Release kinetics of tubulysin from the polymer conjugate at 24 h showed 4.5% release in PBS at pH 5.5, 48% release in PBS at pH 7.4 and 75% release in human plasma at pH 7.5. At 48 h, release kinetics were determined to be 9.2% release in PBS at pH 5.5, 68% release in PBS at pH 7.4 and 82% release in human plasma at pH 7.5.

Example 10

Enhanced Uptake of Cyclodextrin-Based Polymer Nanoparticles by Targeting with LHRH Peptide To increase the cellular uptake of cyclodextrin-based polymer (CDP) in cancer cells, luteinizing hormone-releasing hormone (LHRH) was used as a targeting ligand and the receptor-mediated endocytosis of the nanoparticles investigated in several human cancer cell lines.

LHRH-PEG-maleimide and rhodamine (Rho)-maleimide were conjugated to CDP to form LHRH targeted nanoparticulate polymers (7.1% w/w LHRH, 11.3% w/w Rho). Table 5 lists properties of the prepared CDP naoparticles.

TABLE 5

Properties of CDP naoparticles

| Compound | Mw of parent polymer (kDa) | Mw/Mn* | LHRH loading (wt %) | Rho loading (wt %) | Particle Size (nm)+ |
|---|---|---|---|---|---|
| LHRHa-CDP-Rho | 64 | 2.1 | 7.1 | 11.3 | 41 (145.3) |
| CDP-Rho | 64 | 2.1 | — | 10.7 | 34 (34) |
| sLHRHa-CDP-Rho | 64 | 2.1 | 5.2 | 8.8 | 30 (228.6) |

*Polymer dispersity determined by light scattering techniques.
+Mean particle size determined in water (number in bracket represent in RPMI culture medium) by dynamic light scattering using a ZetaPals instrument (Brookhaven Instruments, Holtsville, NY).

Cellular uptake studies of nanoparticles formed by LHRH targeted CDP-Rho (LHRH-CDP-Rho), non-targeted polymer (CDP-Rho, 10.7% w/w Rho), CDP-Rho mixed with excess LHRH and scrambled LHRH conjugated polymer (sLHRH-CDP-Rho) (5.2% w/w LHRH, 8.8% w/w Rho) were performed at either 37 or 4° C. in MCF-7 (breast cancer), OVCAR-3 (ovarian cancer), and SKOV-3 (ovarian cancer) cell lines and analyzed by microplate reader or FACS. To investigate the endocytosis of LHRH-CDP-Rho, cells were incubated with conjugates at 4° C. and chased with fresh medium at 37° C. The intracellular localization of LHRH-CDP-Rho was visualized by laser scanning confocal microscopy. Table 6 lists cellular uptake levels in various cell lines.

TABLE 6

Cellular uptake levels

| | Percentage (%) of Total Dosing | |
|---|---|---|
| Cell Lines | CDP-Rho | LHRHa-CDP-Rho |
| MCF-7 | 0.02 ± 0.005 | 0.85 ± 0.11 |
| OVCAR | 0.01 ± 0.001 | 0.59 ± 0.18 |
| SKOV-3 | 0.01 ± 0.004 | 0.40 ± 0.09 |

Figure 3:
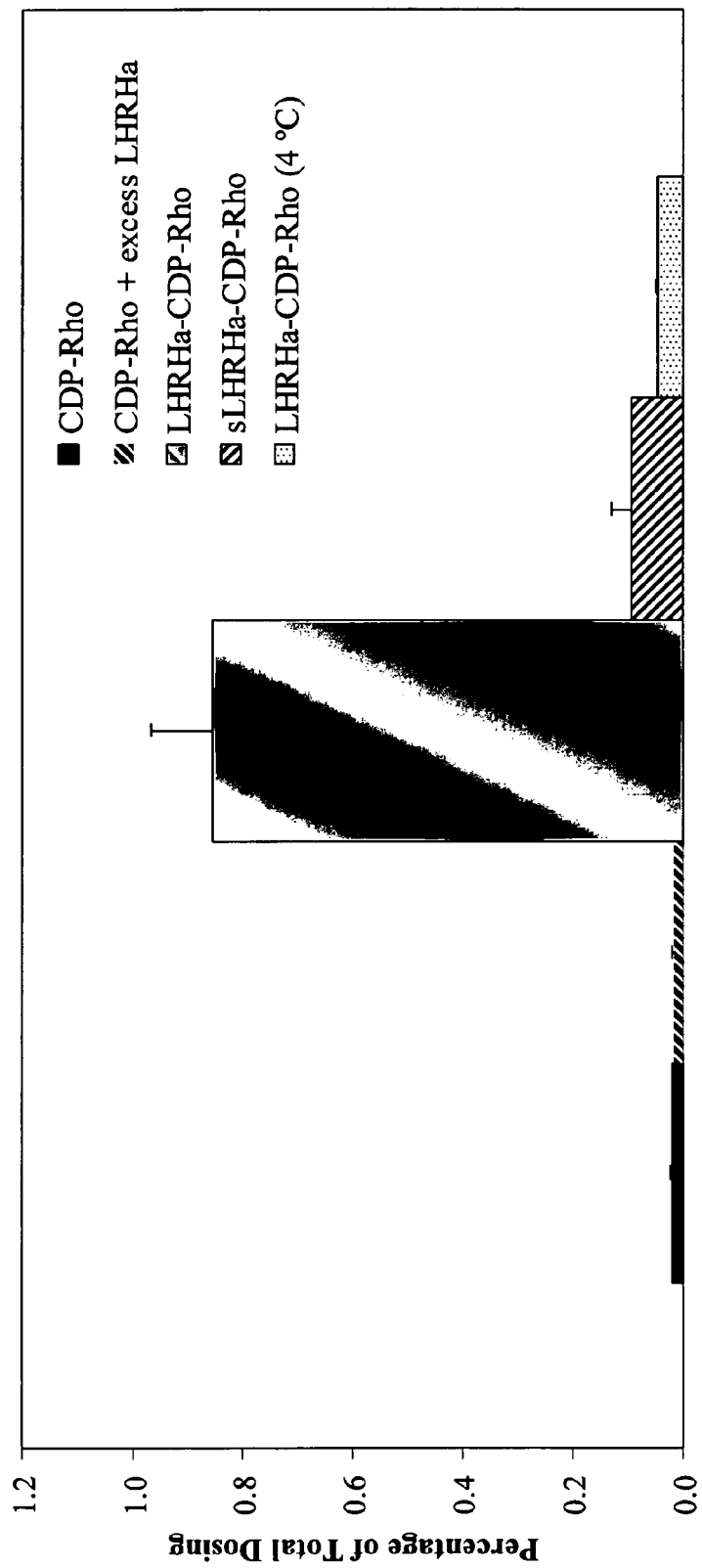
FIG. 3 shows the relative cellular uptake properties of 5 different CDP-Rho systems as a percentage of total dosing.

To assess comparative cellular uptake of CDP-Rho systems, MCF-7 Cells were incubated with LHRHa targeted, sLHRHa targeted or non-targeted CDP-Rho conjugates at a concentration of 30 μM (Rhodamine equivalent) for 3 h at 37° C. or 4° C. Cells in parallel wells were incubated with mixture of CDP-Rho and LHRHa. Cells were then assayed for fluorescence by using a spectrofluorometer (FIG. 3). Each column in FIG. 3 represents the mean of three measurements with error bars representing the standard deviation.

Figure 4:
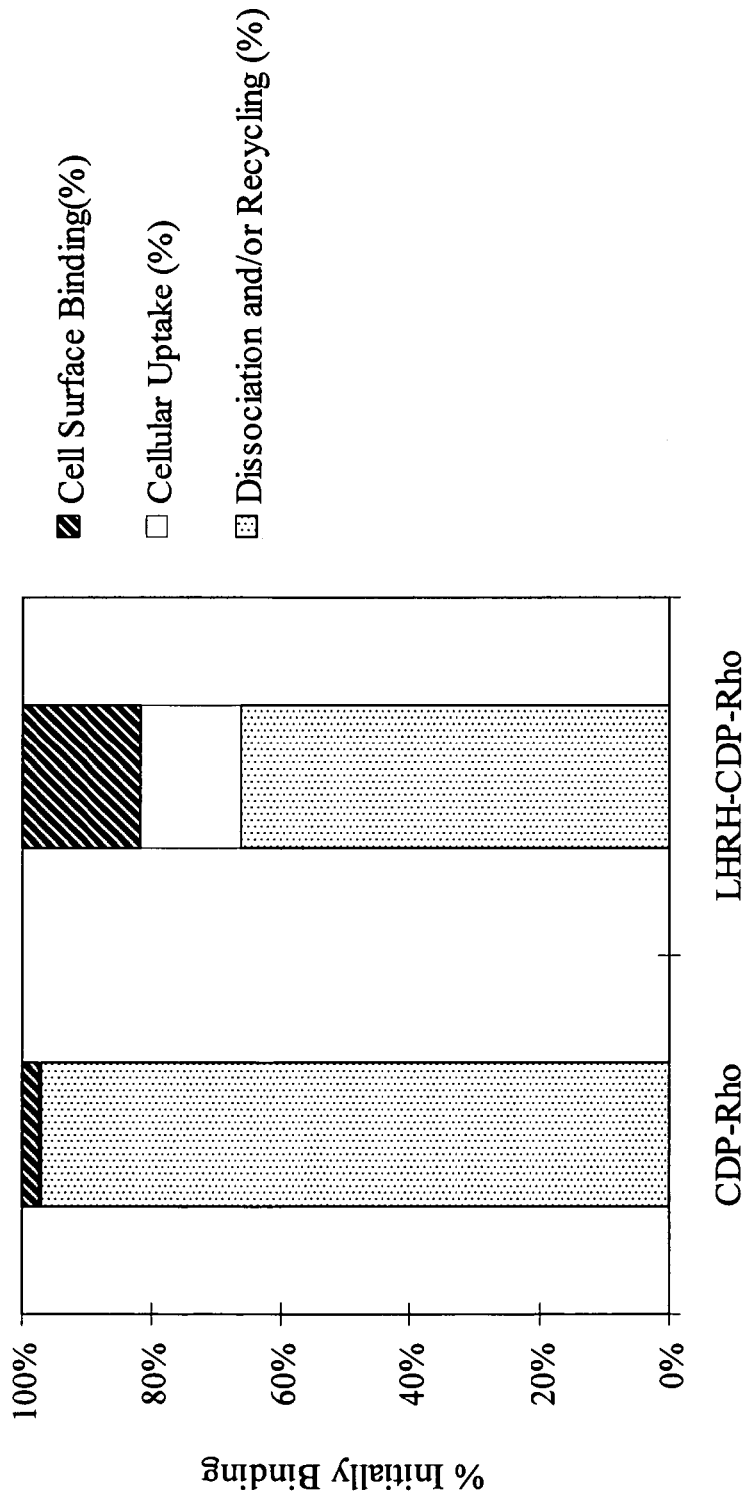
FIG. 4 shows the relative distribution of CDP-Rho in two systems following dosing.

The distribution of CDP-Rho systems following dosing was determined. MCF-7 Cells were pulsed with targeted (LHRHa-CDP-Rho) or non-targeted CDP-Rho conjugates at a concentration of 30 μM for 3 h at 4° C. and then chased at 37° C. for 2 h in fresh medium. The chased medium was assayed as dissociated and/or recycling polymer. The amount of cell surface bound polymer conjugates was determined by trypsin treatment. Finally, the lysed cell was assayed as cellular uptake. Data were interpreted as percentage of initially binding conjugates (FIG. 4). Each column in FIG. 4 represents the mean of three measurements.

Figure 5:
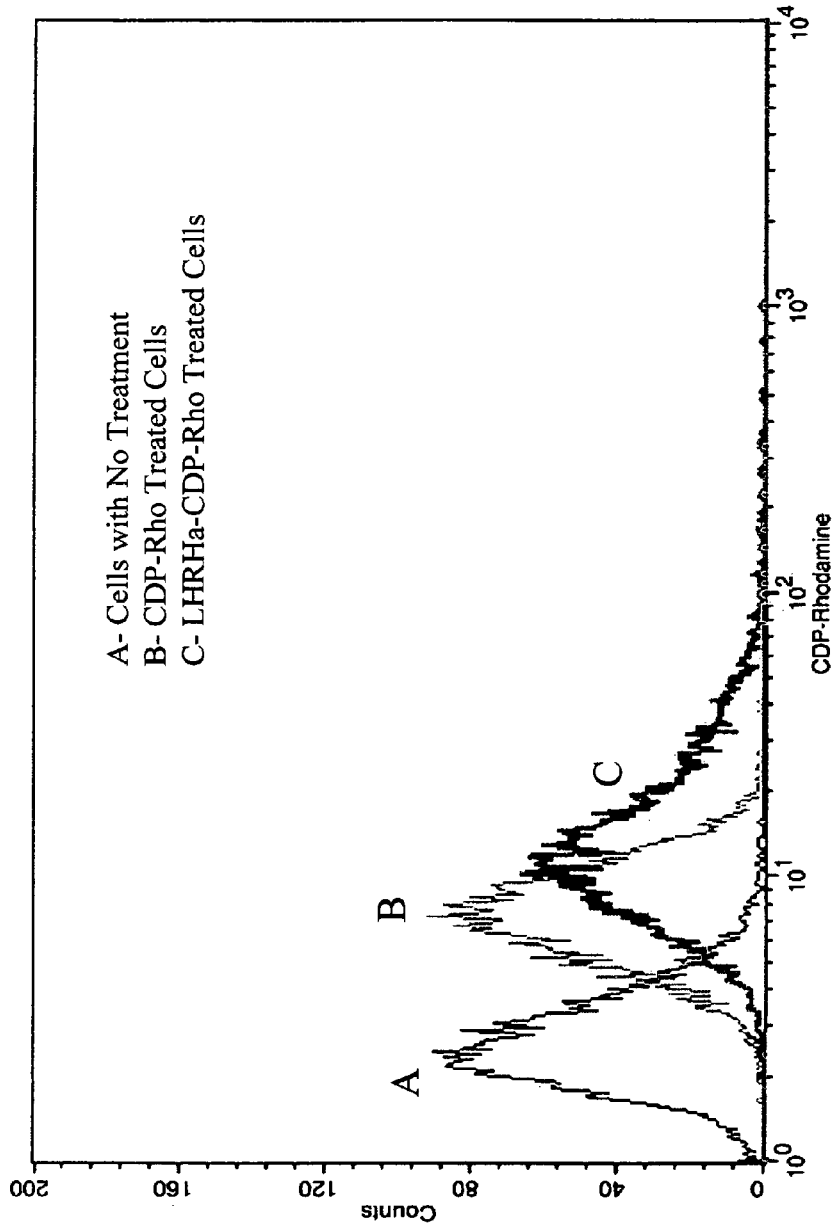
FIG. 5 shows the uptake of CDP-Rho and LHRH-CDP-Rho by flow cytometry.

Comparison of cellular uptake of CDP-Rho vs. LHRH-CDP-Rho was also determined by flow cytometry (FIG. 5). MCF-7 Cells were incubated with polymer conjugates at a concentration of 30 μM (Rhodamine equivalent) for 3 h at 37° C. Cells were then collected, washed and analyzed by flow cytometry.

Pulse chase studies were also conducted (FIG. 6). MCF-7 cells were coincubated with 1 μM Lysotracker Green DND-26 and 2.3 μM LHRHa-CDP-Rho (Rhodamine equivalent) for 1 h at 37° C. In FIG. 6, panel (a) shows localization of LHRHa-CDP-Rho; panel (b) shows localization of lysotracker Green DND-26; panel (c) shows epifluorescence image of MCF cells; and panel (d) shows superposition of (a) and (b), which allows for detection of colocalization of LHRHa-CDP-Rho and Lysotracker Green DND-26.

Results

Cellular uptake of LHRH targeted polymer nanoparticle was 40-60 times higher than that of non-targeted polymer nanoparticle in various cancer cell lines (FIGS. 3-4). A mixture of CDP-Rho with LHRH did not increase the cellular uptake of the CDP-Rho; the cellular uptake of the polymeric nanoparticles was largely decreased when scrambled LHRH was conjugated to polymer compared with LHRH-CDP-Rho;

and the increased cellular uptake of LHRH targeted polymer was inhibited at 4° C. (FIG. 3).

The percentage cellar uptake and cell surface binding was much greater for LHRH-CDP-Rho than for CDP-Rho, while disassociation and/or recycling was reduced (FIG. 4).

Cytometry further showed that cells treated with LHRH targeted CDP nanoparticles showed higher uptake than non-targeted nanoparticles (FIG. 5).

Pulse chase studies demonstrated that the internalization of LHRH-CDP-Rho was temperature dependent. Substantial colocalization of LHRH-CDP-Rho with Lysotracker green was observed by confocal microscopy (FIG. 6).

CONCLUSIONS

The cellular uptake of the examined CDP nanoparticles was greatly enhanced by conjugation with LHRH. In this particular embodiment, the increase in uptake was observed with covalent attachment of LHRH to the polymer nanoparticles and specific binding between LHRH and LHRH-receptor. Also, the internalization process was temperature dependent, and the LHRH targeted polymer nanoparticles localized into the endocytic pathway. These results indicate that hormones, such as LHRH, can be used to increase the intracellular concentration of CDP polymer microparticles or nanoparticles in cells that express the corresponding hormone receptor, such as the LHRH receptor.

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims.

We claim:
1. A polymer conjugate comprising a subunit of the following formula

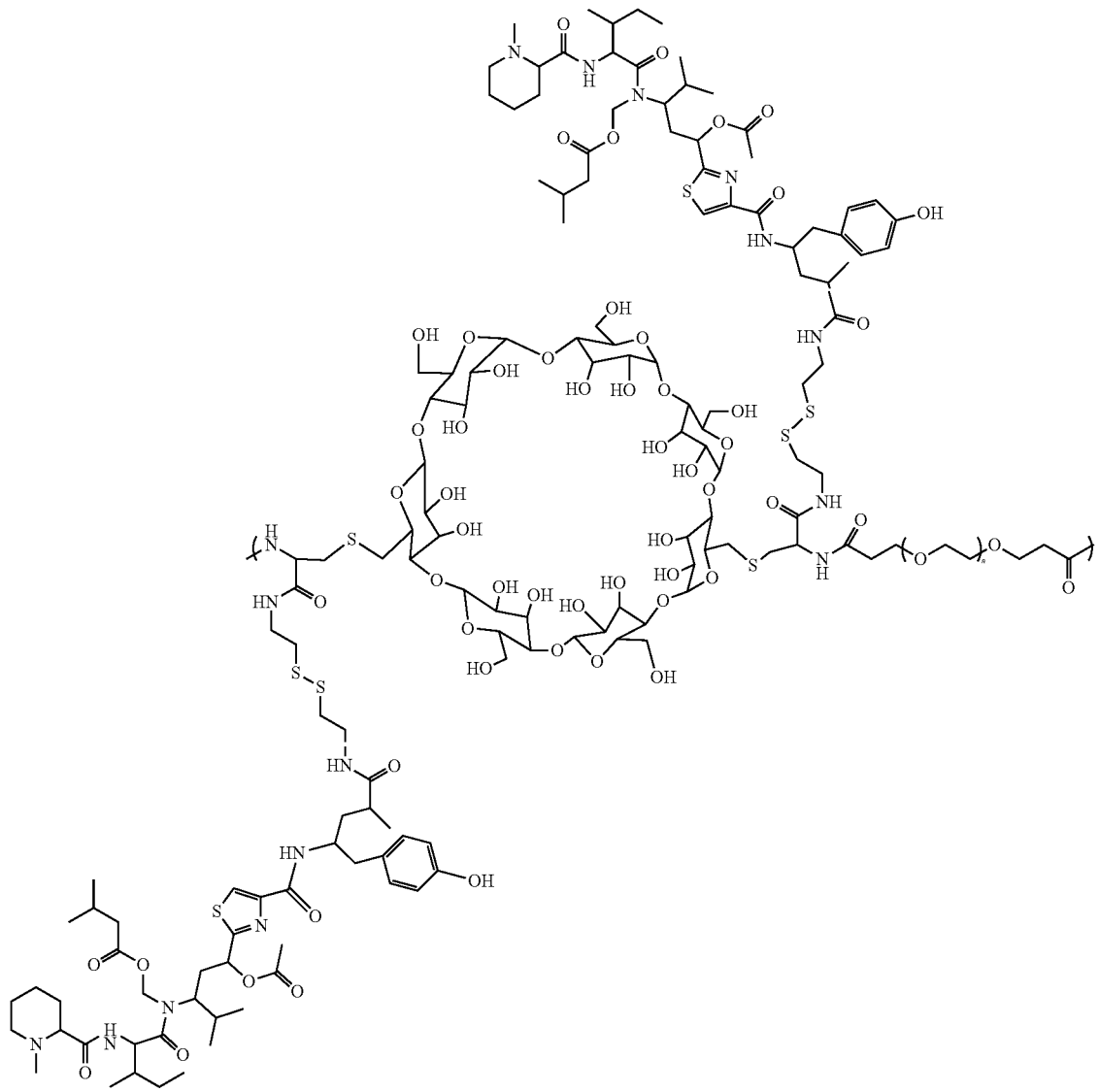

wherein
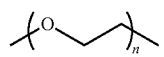
has a molecular weight of 3.4 kDa.
\* \* \* \* \*